US008329429B2

(12) United States Patent
Peel et al.

(10) Patent No.: US 8,329,429 B2
(45) Date of Patent: Dec. 11, 2012

(54) METHOD OF ENHANCING RECOMBINANT PROTEIN PRODUCTION

(75) Inventors: Sean A. F. Peel, Oakville (CA);
Cameron M. L. Clokie, Toronto (CA);
Jeffrey D. Turner, Saint Eugene (CA)

(73) Assignee: Induce Biologics Inc., Toronto (CA)

( * ) Notice: Subject to any disclaimer, the term of this patent is extended or adjusted under 35 U.S.C. 154(b) by 23 days.

(21) Appl. No.: 12/626,441

(22) Filed: Nov. 25, 2009

(65) Prior Publication Data
US 2010/0087625 A1    Apr. 8, 2010

Related U.S. Application Data

(63) Continuation of application No. PCT/CA2008/000998, filed on May 26, 2008.

(60) Provisional application No. 60/940,256, filed on May 25, 2007.

(51) Int. Cl.
*C12N 15/02* (2006.01)
*C12N 5/07* (2010.01)
*C07K 14/51* (2006.01)

(52) U.S. Cl. .... 435/69.1; 435/360; 435/369; 435/365.1; 536/23.5; 530/350

(58) Field of Classification Search ........................ None
See application file for complete search history.

(56) References Cited

U.S. PATENT DOCUMENTS

| | | | |
|---|---|---|---|
| 4,761,471 A | 8/1988 | Urist | |
| 4,789,732 A | 12/1988 | Urist | |
| 4,795,804 A | 1/1989 | Urist | |
| 4,857,456 A | 8/1989 | Urist | |
| 4,877,864 A | 10/1989 | Wang et al. | |
| 5,013,649 A | 5/1991 | Wang et al. | |
| 5,166,058 A | 11/1992 | Wang et al. | |
| 5,318,898 A * | 6/1994 | Israel | 435/69.1 |
| 5,618,924 A | 4/1997 | Wang et al. | |
| 5,631,142 A | 5/1997 | Wang et al. | |
| 5,658,882 A | 8/1997 | Celeste et al. | |
| 5,712,119 A | 1/1998 | Oppermann et al. | |
| 5,830,761 A | 11/1998 | Drapeau et al. | |
| 5,866,364 A | 2/1999 | Israel et al. | |
| 6,150,328 A | 11/2000 | Wang et al. | |
| 6,503,109 B1 | 1/2003 | Duffield et al. | |
| 6,593,109 B1 | 7/2003 | Israel et al. | |
| 7,300,772 B2 | 11/2007 | Wang et al. | |
| 7,354,901 B2 | 4/2008 | Rudolph et al. | |
| 2004/0226053 A1* | 11/2004 | Meade et al. | 800/7 |
| 2006/0235204 A1 | 10/2006 | Desjarlais et al. | |

FOREIGN PATENT DOCUMENTS

| WO | WO 95/33841 | 12/1995 |
|---|---|---|
| WO | WO 96/04390 | 2/1996 |

OTHER PUBLICATIONS

Lopez et al. Dominant negative mutants of transforming growth factor-beta 1 inhibit the secretion of different transforming growth factor-beta isoforms. Mol Cell Biol. Apr. 1992;12(4):1674-9.*
International Search Report issued in PCT/CA2008/00998 filed on May 26, 2008.
Israel, D.I. et al., *Expression and characterization of bone morphogenetic protein-2 in chinese hamster ovary cells*. Growth Factors (1992) vol. 7, pp. 139-150.
Hammonds, R.G. et al., *Bone-inducing activity of mature BMP-2B produced from a hybrid BMP-2a/2b precursor*. Molecular Endocrinology (1991) vol. 5, No. 1, pp. 149-155.
Takahashi, S. et al., *A mutation of furin causes the lack of precursor-processing activity in human colon carcinoma LoVo cells*. Biochemical and Biophysical Research Communications (1993) vol. 195, No. 2, pp. 1019-1026.
Supplementary European Search Report issued in EP 08 75 7135 issued on Nov. 16, 2010.
Kummer J Alain et al: "Expression of human recombinant granzyme A zymogen and its activation by the cysteine proteinase cathepsin C", Journal of Biological Chemistry, American Society for Biochemistry and Molecular Biology, Inc, US, vol. 271, No. 16, Jan. 1, 1996, pp. 9281-9286, XP002158677, ISSN: 0021-9258, DOI: DOI:10.1074/JBC.271.16.9281.
Brattsand M et al: "Purification Molecular Cloning, and Expression of a Human Stratum Corneum Trypsin-like Serine Protease with Possible Function in Desquamation", Journal of Biological Chemistry, American Society for Biochemistry and Molecular Biology, Inc, US, vol. 247, No. 42, Oct. 15, 1999, pp. 30033-30040, XP000862810, ISSN: 0021-9258, DOI: DOI:10.1074/JBC.274.42.30033.
Kowalska Dorota et al: "Synthetic Small-Molecule Prohormone Convertase 2 Inhibitors", Molecular Pharmacology, vol. 75, No. 3, Mar. 2009, pp. 617-625 URL, XP002609663, ISSN: 0026-895X.
Apletalina Ekaterina et al: "Identification of inhibitors of prohormone convertases 1 and 2 using a peptide combinatorial library", Journal of Biological Chemistry. American Society for Biochemistry and Molecular Biology, Inc US. vol. 273. No. 41. Oct. 9, 1998, pp. 26589-26595, XP002355258. ISSN: 0021-9258. 001: DOI:10.1074fJBC.273.41.26589.

* cited by examiner

*Primary Examiner* — David Romeo
(74) *Attorney, Agent, or Firm* — Ainslie Little; Blake, Cassels & Graydon LLP

(57) ABSTRACT

The present invention provides a method of enhanced protein production that comprises the step of expressing a recombinant gene encoding the protein in eukaryotic cells under conditions in which cleavage of the pro-domain of the protein is inhibited or eliminated. Generally the method of the present invention includes the step of inhibiting or altering the cleavage of a pro-domain of a recombinant protein of interest in order to increase the amount of recombinant protein secreted from a eukaryotic cell. Recombinant proteins that can be prepared using the method of this invention include members of the transforming growth factor-β (TGF-β) superfamily, such as bone morphogenetic proteins. Also provided are genetically engineered cells and polynucleotides for performing the method of the invention.

8 Claims, 28 Drawing Sheets

SEQ ID NO:1

```
GGGGACTTCTTGAACTTGCAGGGAGAATAACTTGCGCACCCCACTTTGCGCCGGTGCCTTTGCCCCAGCGGAGCCTG
CTTCGCCATCTCCGAGCCCCACCGCCCCTCCACTCCTCGGCCTTGCCCGACACTGAGACGCTGTTCCCAGCGTGAAA
AGAGAGACTGCGCGGCCGGCACCCGGGAGAAGGAGGAGGCAAAGAAAAGGAACGGACATTCGGTCCTTGCGCCAGGT
CCTTTGACCAGAGTTTTTCCATGTGGACGCTCTTTCAATGGACGTGTCCCCGCGTGCTTCTTAGACGGACTGCGGTC
TCCTAAAGGTCGACCATGGTGGCCGGGACCCGCTGTCTTCTAGCGTTGCTGCTTCCCCAGGTCCTCCTGGGCGGCGC
GGCTGGCCTCGTTCCGGAGCTGGGCCGCAGGAAGTTCGCGGCGGCGTCGTCGGGCCGCCCCTCATCCCAGCCCTCTG
ACGAGGTCCTGAGCGAGTTCGAGTTGCGGCTGCTCAGCATGTTCGGCCTGAAACAGAGACCCACCCCCAGCAGGGAC
GCCGTGGTGCCCCCCTACATGCTAGACCTGTATCGCAGGCACTCAGGTCAGCCGGGCTCACCCGCCCCAGACCACCG
GTTGGAGAGGGCAGCCAGCCGAGCCAACACTGTGCGCAGCTTCCACCATGAAGAATCTTTGGAAGAACTACCAGAAA
CGAGTGGGAAAACAACCCGGAGATTCTTCTTTAATTTAAGTTCTATCCCCACGGAGGAGTTTATCACCTCAGCAGAG
CTTCAGGTTTTCCGAGAACAGATGCAAGATGCTTTAGGAAACAATAGCAGTTTCCATCACCGAATTAATATTTATGA
AATCATAAAACCTGCAACAGCCAACTCGAAATTCCCCGTGACCAGACTTTTGGACACCAGGTTGGTGAATCAGAATG
CAAGCAGGTGGGAAAGTTTTGATGTCACCCCCGCTGTGATGCGGTGGACTGCACAGGGACACGCCAACCATGGATTC
GTGGTGGAAGTGGCCCACTTGGAGGAGAAACAAGGTGTCTCCAAGAGACATGTTAGGATAAGCAGGTCTTTGCACCA
AGATGAACACAGCTGGTCACAGATAAGGCCATTGCTAGTAACTTTTGGCCATGATGGAAAAGGGCATCCTCTCCACA
AAAGAGAAAAACGTCAAGCCAAACACAAACAGCGGAAACGCCTTAAGTCCAGCTGTAAGAGACACCCTTTGTACGTG
GACTTCAGTGACGTGGGGTGGAATGACTGGATTGTGGCTCCCCCGGGGTATCACGCCTTTTACTGCCACGGAGAATG
CCCTTTTCCTCTGGCTGATCATCTGAACTCCACTAATCATGCCATTGTTCAGACGTTGGTCAACTCTGTTAACTCTA
AGATTCCTAAGGCATGCTGTGTCCCGACAGAACTCAGTGCTATCTGATGCTGTACCTTGACGAGAATGAAAAGGTT
GTATTAAAGAACTATCAGGACATGGTTGTGGAGGGTTGTGGGTGTCGCTAGTACAGCAAAATTAAATACATAAATAT
ATATATA
```

FIGURE 1

SEQ ID NO: 2

```
MVAGTRCLLALLLPQVLLGGAAGLVPELGRRKFAAASSGRPSSQPSDEVLSEFELRLLSMFGLKQRPTPS
RDAVVPPYMLDLYRRHSGQPGSPAPDHRLERAASRANTVRSFHHEESLEELPETSGKTTRRFFFNLSSIP
TEEFITSAELQVFREQMQDALGNNSSFHHRINIYEIIKPATANSKFPVTRLLDTRLVNQNASRWESFDVT
PAVMRWTAQGHANHGFVVEVAHLEEKQGVSKRHVRISRSLHQDEHSWSQIRPLLVTFGHDGKGHPLHKRE
KRQAKHQRKRLKSSCKRHPLYVDFSDVGWNDWIVAPPGYHAFYCHGECPFPLADHLNSTNHAIVQTLVN
SVNSKIPKACCVPTELSAISMLYLDENEKVVLKNYQDMVVEGCGCR
```

FIGURE 2

SEQ ID NO: 3

```
GGGCGCAGCGGGGCCCGTCTGCAGCAAGTGACCGACGGCCGGGACGGCCGCCTGCCCCCTCTGCCACCTGGGGCGGT
GCGGGCCCGGAGCCCGGAGCCCGGGTAGCGCGTAGAGCCGGCGCGATGCACGTGCGCTCACTGCGAGCTGCGGCGCC
GCACAGCTTCGTGGCGCTCTGGGCACCCCTGTTCCTGCTGCGCTCCGCCCTGGCCGACTTCAGCCTGGACAACGAGG
TGCACTCGAGCTTCATCCACCGGCGCCTCCGCAGCCAGGAGCGGCGGGAGATGCAGCGCGAGATCCTCTCCATTTTG
GGCTTGCCCCACCGCCCGCGCCCGCACCTCCAGGGCAAGCACAACTCGGCACCCATGTTCATGCTGGACCTGTACAA
CGCCATGGCGGTGGAGGAGGGCGGCGGGCCCGGCGGCCAGGGCTTCTCCTACCCCTACAAGGCCGTCTTCAGTACCC
AGGGCCCCCCTCTGGCCAGCCTGCAAGATAGCCATTTCCTCACCGACGCCGACATGGTCATGAGCTTCGTCAACCTC
GTGGAACATGACAAGGAATTCTTCCACCCACGCTACCACCATCGAGAGTTCCGGTTTGATCTTTCCAAGATCCCAGA
AGGGGAAGCTGTCACGGCAGCCGAATTCCGGATCTACAAGGACTACATCCGGGAACGCTTCGACAATGAGACGTTCC
GGATCAGCGTTTATCAGGTGCTCCAGGAGCACTTGGGCAGGGAATCGGATCTCTTCCTGCTCGACAGCCGTACCCTC
TGGGCCTCGGAGGAGGGCTGGCTGGTGTTTGACATCACAGCCACCAGCAACCACTGGGTGGTCAATCCGCGGCACAA
CCTGGGCCTGCAGCTCTCGGTGGAGACGCTGGATGGGCAGAGCATCAACCCCAAGTTGGCGGGCCTGATTGGGCGGC
ACGGGCCCCAGAACAAGCAGCCCTTCATGGTGGCTTTCTTCAAGGCCACGGAGGTCCACTTCCGCAGCATCCGGTCC
ACGGGGAGCAAACAGCGCAGCCAGAACCGCTCCAAGACGCCCAAGAACCAGGAAGCCCTGCGGATGGCCAACGTGGC
AGAGAACAGCAGCAGCGACCAGAGGCAGGCCTGTAAGAAGCACGAGCTGTATGTCAGCTTCCGAGACCTGGGCTGGC
AGGACTGGATCATCGCGCCTGAAGGCTACGCCGCCTACTACTGTGAGGGGGAGTGTGCCTTCCCTCTGAACTCCTAC
ATGAACGCCACCAACCACGCCATCGTGCAGACGCTGGTCCACTTCATCAACCCGGAAACGGTGCCCAAGCCCTGCTG
TGCGCCCACGCAGCTCAATGCCATCTCCGTCCTCTACTTCGATGACAGCTCCAACGTCATCCTGAAGAAATACAGAA
ACATGGTGGTCCGGCCTGTGGCTGCCACTAGCTCCTCCGAGAATTCAGACCCTTTGGGCCAAGTTTTTCTGGATC
CTCCATTGCTCGCCTTGGCCAGGAACCAGCAGACCAACTGCCTTTTGTGAGACCTTCCCCTCCCTATCCCCAACTTT
AAAGGTGTGAGAGTATTAGGAAACATGAGCAGCATATGGCTTTTGATCAGTTTTTCAGTGGCAGCATCCAATGAACA
AGATCCTACAAGCTGTGCAGGCAAAACCTAGCAGGAAAAAAAAACAACGCATAAAGAAAAATGGCCGGGCCAGGTCA
TTGGCTGGGAAGTCTCAGCCATGCACGGACTCGTTTCCAGAGGTAATTATGAGCGCCTACCAGCCAGGCCACCCAGC
CGTGGGAGGAAGGGGCGTGGCAAGGGGTGGGCACATTGGTGTCTGTGCAAAGGAAAATTGACCCGGAAGTTCCTG
TAATAAATGTCACAATAAAACGAATGAATG
```

FIGURE 3

SEQ ID NO: 4

```
MHVRSLRAAAPHSFVALWAPLFLLRSALADFSLDNEVHSSFIHRRLRSQERREMQREILSILGLPHRPRP
HLQGKHNSAPMFMLDLYNAMAVEEGGGPGGQGFSYPYKAVFSTQGPPLASLQDSHFLTDADMVMSFVNLV
EHDKEFFHPRYHHREFRFDLSKIPEGEAVTAAEFRIYKDYIRERFDNETFRISVYQVLQEHLGRESDLFL
LDSRTLWASEEGWLVFDITATSNHWVVNPRHNLGLQLSVETLDGQSINPKLAGLIGRHGPQNKQPFMVAF
FKATEVHFRSIRSTGSKQRSQNRSKTPKNQEALRMANVAENSSSDQRQACKKHELYVSFRDLGWQDWIIA
PEGYAAYYCEGECAFPLNSYMNATNHAIVQTLVHFINPETVPKPCCAPTQLNAISVLYFDDSSNVILKKY
RNMVVRACGCH
```

FIGURE 4

SEQ ID NO: 5

```
TCGACCCACGCGTCCGGGCAGAGGAGGAGGGAGGGAGGGAAGGAGCGCGGAGCCCGGCCCGGAAGCTAGG
AGCCATTCCGTAGTGCCATCCCGAGCAACGCACTGCTGCAGCTTCCCTGAGCCTTTCCAGCAAGTTTGTT
CAAGATTGGCTGTCAAGAATCATGGACTGTTATTATATGCCTTGTTTTCTGTCAAGACACCATGATTCCT
GGTAACCGAATGCTGATGGTCGTTTTATTATGCCAAGTCCTGCTAGGAGGCGCGAGCCATGCTAGTTTGA
TACCTGAGACGGGGAAGAAAAAAGTCGCCGAGATTCAGGGCCACGCGGGAGGACGCCGCTCAGGGCAGAG
CCATGAGCTCCTGCGGGACTTCGAGGCGACACTTCTGCAGATGTTTGGGCTGCGCCGCCGCCCGCAGCCT
AGCAAGAGTGCCGTCATTCCGGACTACATGCGGGATCTTTACCGGCTTCAGTCTGGGGAGGAGGAGGAAG
AGCAGATCCACAGCACTGGTCTTGAGTATCCTGAGCGCCCGGCCAGCCGGGCCAACACCGTGAGGAGCTT
CCACCACGAAGAACATCTGGAGAACATCCCAGGGACCAGTGAAAACTCTGCTTTTCGTTCCTCTTTAAC
CTCAGCAGCATCCCTGAGAACGAGGCGATCTCCTCTGCAGAGCTTCGGCTCTTCCGGGAGCAGGTGGACC
AGGGCCCTGATTGGGAAAGGGGCTTCCACCGTATAAACATTTATGAGGTTATGAAGCCCCCAGCAGAAGT
GGTGCCTGGGCACCTCATCACACGACTACTGGACACGAGACTGGTCCACCACAATGTGACACGGTGGGAA
ACTTTTGATGTGAGCCCTGCGGTCCTTCGCTGGACCCGGGAGAAGCAGCCAAACTATGGGCTAGCCATTG
AGGTGACTCACCTCCATCAGACTCGGACCCACCAGGGCCAGCATGTCAGGATTAGCCGATCGTTACCTCA
AGGGAGTGGGAATTGGGCCCAGCTCCGGCCCCTCCTGGTCACCTTTGGCCATGATGGCCGGGGCCATGCC
TTGACCCGACGCCGGAGGGCCAAGCGTAGCCCTAAGCATCACTCACAGCGGGCCAGGAAGAAGAATAAGA
ACTGCCGGCGCCACTCGCTCTATGTGGACTTCAGCGATGTGGGCTGGAATGACTGGATTGTGGCCCCACC
AGGCTACCAGGCCTTCTACTGCCATGGGACTGCCCCTTTCCACTGGCTGACCACCTCAACTCAACCAAC
CATGCCATTGTGCAGACCCTGGTCAATTCTGTCAATTCCAGTATCCCCAAAGCCTGTTGTGTGCCCACTG
AACTGAGTGCCATCTCCATGCTGTACCTGGATGAGTATGATAAGGTGGTACTGAAAAATTATCAGGAGAT
GGTAGTAGAGGGATGTGGGTGCCGCTGAGATCAGGCAGTCCTTGAGGATAGACAGATATACACACCACAC
ACACACACCACATACACCACACACACGTTCCCATCCACTCACCCACACACTACACAGACTGCTTCCTT
ATAGCTGGACTTTTATTTAAAAAAAAAAAAAAA
```

FIGURE 5

SEQ ID NO: 6

```
MIPGNRMLMVVLLCQVLLGGASHASLIPETGKKKVAEIQGHAGGRRSGQSHELLRDFEATLLQMFGLRRR
PQPSKSAVIPDYMRDLYRLQSGEEEEEQIHSTGLEYPERPASRANTVRSFHHEEHLENIPGTSENSAFRF
LFNLSSIPENEAISSAELRLFREQVDQGPDWERGFHRINIYEVMKPPAEVVPGHLITRLLDTRLVHHNVT
RWETFDVSPAVLRWTREKQPNYGLAIEVTHLHQTRTHQGQHVRISRSLPQGSGNWAQLRPLLVTFGHDGR
GHALTRRRRAKRSPKHHSQRARKKNKNCRRHSLYVDFSDVGWNDWIVAPPGYQAFYCHGDCPFPLADHLN
STNHAIVQTLVNSVNSSIPKACCVPTELSAISMLYLDEYDKVVLKNYQEMVVEGCGCR
```

FIGURE 6

SEQ ID NO: 7

```
GGGGACTTCTTGAACTTGCAGGGAGAATAACTTGCGCACCCCACTTTGCGCCGGTGCCTTTGCCCCAGCGGAGCCTG
CTTCGCCATCTCCGAGCCCCACCGCCCCTCCACTCCTCGGCCTTGCCCGACACTGAGACGCTGTTCCCAGCGTGAAA
AGAGAGACTGCGCGGCCGGCACCCGGGAGAAGGAGGAGGCAAAGAAAAGGAACGGACATTCGGTCCTTGCGCCAGGT
CCTTTGACCAGAGTTTTTCCATGTGGACGCTCTTTCAATGGACGTGTCCCCGCGTGCTTCTTAGACGGACTGCGGTC
TCCTAAAGGTCGACCATGGTGGCCGGGACCCGCTGTCTTCTAGCGTTGCTGCTTCCCCAGGTCCTCCTGGGCGGCGC
GGCTGGCCTCGTTCCGGAGCTGGGCCGCAGGAAGTTCGCGGCGGCGTCGTCGGGCCGCCCCTCATCCCAGCCCTCTG
ACGAGGTCCTGAGCGAGTTCGAGTTGCGGCTGCTCAGCATGTTCGGCCTGAAACAGAGACCCACCCCCAGCAGGGAC
GCCGTGGTGCCCCCCTACATGCTAGACCTGTATCGCAGGCACTCAGGTCAGCCGGGCTCACCCGCCCCAGACCACCG
GTTGGAGAGGGCAGCCAGCCGAGCCAACACTGTGCGCAGCTTCCACCATGAAGAATCTTTGGAAGAACTACCAGAAA
CGAGTGGGAAAACAACCCGGAGATTCTTCTTTAATTTAAGTTCTATCCCCACGGAGGAGTTTATCACCTCAGCAGAG
CTTCAGGTTTTCCGAGAACAGATGCAAGATGCTTTAGGAAACAATAGCAGTTTCCATCACCGAATTAATATTTATGA
AATCATAAAACCTGCAACAGCCAACTCGAAATTCCCCGTGACCAGACTTTTGGACACCAGGTTGGTGAATCAGAATG
CAAGCAGGTGGGAAAGTTTTGATGTCACCCCCGCTGTGATGCGGTGGACTGCACAGGGACACGCCAACCATGGATTC
GTGGTGGAAGTGGCCCACTTGGAGGAGAAACAAGGTGCTCCAAGAGACATGTTAGGATAAGCAGGTCTTTGCACCA
AGATGAACACAGCTGGTCACAGATAAGGCCATTGCTAGTAACTTTTGGCCATGATGGAAAAGGGCATCCTCTCCACC
TGGAAGTGCTGTTTCAGGGCCCGAAACATAAACAGCGGAAACGCCTTAAGTCCAGCTGTAAGAGACACCCTTGTAC
GTGGACTTCAGTGACGTGGGGTGGAATGACTGGATTGTGGCTCCCCGGGGTATCACGCCTTTTACTGCCACGGAGA
ATGCCCTTTTCCTCTGGCTGATCATCTGAACTCCACTAATCATGCCATTGTTCAGACGTTGGTCAACTCTGTTAACT
CTAAGATTCCTAAGGCATGCTGTGTCCCGACAGAACTCAGTGCTATCTCGATGCTGTACCTTGACGAGAATGAAAAG
GTTGTATTAAAGAACTATCAGGACATGGTTGTGGAGGGTTGTGGGTGTCGCTAGTACAGCAAAATTAAATACATAAA
TATATATATA
```

FIGURE 7

SEQ ID NO: 8

```
MVAGTRCLLALLLPQVLLGGAAGLVPELGRRKFAAASSGRPSSQPSDEVLSEFELRLLSMFGLKQRPTPSRDAVVPP
YMLDLYRRHSGQPGSPAPDHRLERAASRANTVRSFHHEESLEELPETSGKTTRRFFFNLSSIPTEEFITSAELQVFR
EQMQDALGNNSSFHHRINIYEIIKPATANSKFPVTRLLDTRLVNQNASRWESFDVTPAVMRWTAQGHANHGFVVEVA
HLEEKQGVSKRHVRISRSLHQDEHSWSQIRPLLVTFGHDGKGHPLHLEVLFQGPKHKQRKRLKSSCKRHPLYVDFSD
VGWNDWIVAPPGYHAFYCHGECPFPLADHLNSTNHAIVQTLVNSVNSKIPKACCVPTELSAISMLYLDENEKVVLKN
YQDMVVEGCGCR
```

FIGURE 8

SEQ ID NO: 9

```
GGGGACTTCTTGAACTTGCAGGGAGAATAACTTGCGCACCCCACTTTGCGCCGGTGCCTTTGCCCCAGCGGAGCCTG
CTTCGCCATCTCCGAGCCCCACCGCCCCTCCACTCCTCGGCCTTGCCCGACACTGAGACGCTGTTCCCAGCGTGAAA
AGAGAGACTGCGCGGCCGGCACCCGGGAGAAGGAGGAGGCAAAGAAAAGGAACGGACATTCGGTCCTTGCGCCAGGT
CCTTTGACCAGAGTTTTTCCATGTGGACGCTCTTTCAATGGACGTGTCCCCGCGTGCTTCTTAGACGGACTGCGGTC
TCCTAAAGGTCGACCATGGTGGCCGGGACCCGCTGTCTTCTAGCGTTGCTGCTTCCCCAGGTCCTCCTGGGCGGCGC
GGCTGGCCTCGTTCCGGAGCTGGGCCGCAGGAAGTTCGCGGCGGCGTCGTCGGGCCGCCCCTCATCCCAGCCCTCTG
ACGAGGTCCTGAGCGAGTTCGAGTTGCGGCTGCTCAGCATGTTCGGCCTGAAACAGAGACCCACCCCCAGCAGGGAC
GCCGTGGTGCCCCCCTACATGCTAGACCTGTATCGCAGGCACTCAGGTCAGCCGGGCTCACCCGCCCCAGACCACCG
GTTGGAGAGGGCAGCCAGCCGAGCCAACACTGTGCGCAGCTTCCACCATGAAGAATCTTTGGAAGAACTACCAGAAA
CGAGTGGGAAAACAACCCGGAGATTCTTCTTTAATTTAAGTTCTATCCCCACGGAGGAGTTTATCACCTCAGCAGAG
CTTCAGGTTTTCCGAGAACAGATGCAAGATGCTTTAGGAAACAATAGCAGTTTCCATCACCGAATTAATATTTATGA
AATCATAAAACCTGCAACAGCCAACTCGAAATTCCCCGTGACCAGACTTTTGGACACCAGGTTGGTGAATCAGAATG
CAAGCAGGTGGGAAAGTTTTGATGTCACCCCCGCTGTGATGCGGTGGACTGCACAGGGACACGCCAACCATGGATTC
GTGGTGGAAGTGGCCCACTTGGAGGAGAAACAAGGTGTCTCCAAGAGACATGTTGCGATAAGCAGGTCTTTGCACCA
AGATGAACACAGCTGGTCACAGATAAGGCCATTGCTAGTAACTTTTGGCCATGATGGAAAAGGGCATCCTCTCCACA
AAGCAGAAAAACGTCAAGCCAAACACAAACAGCGGAAACGCCTTAAGTCCAGCTGTAAGAGACACCCTTTGTACGTG
GACTTCAGTGACGTGGGGTGGAATGACTGGATTGTGGCTCCCCCGGGGTATCACGCCTTTTACTGCCACGGAGAATG
CCCTTTTCCTCTGGCTGATCATCTGAACTCCACTAATCATGCCATTGTTCAGACGTTGGTCAACTCTGTTAACTCTA
AGATTCCTAAGGCATGCTGTGTCCCGACAGAACTCAGTGCTATCTCGATGCTGTACCTTGACGAGAATGAAAAGGTT
GTATTAAAGAACTATCAGGACATGGTTGTGGAGGGTTGTGGGTGTCGCTAGTACAGCAAAATTAAATACATAAATAT
ATATATA
```

FIGURE 9

SEQ ID NO: 10

```
MVAGTRCLLALLLPQVLLGGAAGLVPELGRRKFAAASSGRPSSQPSDEVLSEFELRLLSMFGLKQRPTPS
RDAVVPPYMLDLYRRHSGQPGSPAPDHRLERAASRANTVRSFHHEESLEELPETSGKTTRRFFFNLSSIP
TEEFITSAELQVFREQMQDALGNNSSFHHRINIYEIIKPATANSKFPVTRLLDTRLVNQNASRWESFDVT
PAVMRWTAQGHANHGFVVEVAHLEEKQGVSKRHVAISRSLHQDEHSWSQIRPLLVTFGHDGKGHPLHKAE
KRQAKHKQRKRLKSSCKRHPLYVDFSDVGWNDWIVAPPGYHAFYCHGECPFPLADHLNSTNHAIVQTLVN
SVNSKIPKACCVPTELSAISMLYLDENEKVVLKNYQDMVVEGCGCR
```

FIGURE 10

SEQ ID NO: 11

```
GGGCGCAGCGGGGCCCGTCTGCAGCAAGTGACCGACGGCCGGGACGGCCGCCTGCCCCCTCTGCCACCTGGGGCGGT
GCGGGCCCGGAGCCCGGAGCCCGGGTAGCGCGTAGAGCCGGCGCGATGCACGTGCGCTCACTGCGAGCTGCGGCGCC
GCACAGCTTCGTGGCGCTCTGGGCACCCCTGTTCCTGCTGCGCTCCGCCCTGGCCGACTTCAGCCTGGACAACGAGG
TGCACTCGAGCTTCATCCACCGGCGCCTCCGCAGCCAGGAGCGGCGGGAGATGCAGCGCGAGATCCTCTCCATTTTG
GGCTTGCCCCACCGCCCGCGCCCGCACCTCCAGGGCAAGCACAACTCGGCACCCATGTTCATGCTGGACCTGTACAA
CGCCATGGCGGTGGAGGAGGGCGGCGGGCCCGGCGGCCAGGGCTTCTCCTACCCCTACAAGGCCGTCTTCAGTACCC
AGGGCCCCCCTCTGGCCAGCCTGCAAGATAGCCATTTCCTCACCGACGCCGACATGGTCATGAGCTTCGTCAACCTC
GTGGAACATGACAAGGAATTCTTCCACCCACGCTACCACCATCGAGAGTTCCGGTTTGATCTTTCCAAGATCCCAGA
AGGGGAAGCTGTCACGGCAGCCGAATTCCGGATCTACAAGGACTACATCCGGGAACGCTTCGACAATGAGACGTTCC
GGATCAGCGTTTATCAGGTGCTCCAGGAGCACTTGGGCAGGGAATCGGATCTCTTCCTGCTCGACAGCCGTACCCTC
TGGGCCTCGGAGGAGGGCTGGCTGGTGTTTGACATCACAGCCACCAGCAACCACTGGGTGGTCAATCCGCGGCACAA
CCTGGGCCTGCAGCTCTCGGTGGAGACGCTGGATGGGCAGAGCATCAACCCCAAGTTGGCGGGCCTGATTGGGCGGC
ACGGGCCCCAGAACAAGCAGCCCTTCATGGTGGCTTTCTTCAAGGCCACGGAGGTCCACTTCCTGGAAGTGCTGTTT
CAGGGCCCCGAAACATCAGCGCAGCCAGAACCGCTCCAAGACGCCCAAGAACCAGGAAGCCCTGCGGATGGCCAACGT
GGCAGAGAACAGCAGCAGCGACCAGAGGCAGGCCTGTAAGAAGCACGAGCTGTATGTCAGCTTCCGAGACCTGGGCT
GGCAGGACTGGATCATCGCGCCTGAAGGCTACGCCGCCTACTACTGTGAGGGGAGTGTGCCTTCCCTCTGAACTCC
TACATGAACGCCACCAACCACGCCATCGTGCAGACGCTGGTCCACTTCATCAACCCGGAAACGGTGCCCAAGCCCTG
CTGTGCGCCCACCCAGCTCAATGCCATCTCCGTCCTCTACTTCGATGACAGCTCCAACGTCATCCTGAAGAAATACA
GAAACATGGTGGTCCGGGCCTGTGGCTGCCACTAGCTCCTCCGAGAATTCAGACCCTTTGGGGCCAAGTTTTTCTGG
ATCCTCCATTGCTCGCCTTGGCCAGGAACCAGCAGACCAACTGCCTTTTGTGAGACCTTCCCCTCCCTATCCCCAAC
TTTAAAGGTGTGAGAGTATTAGGAAACATGAGCAGCATATGGCTTTTGATCAGTTTTTCAGTGGCAGCATCCAATGA
ACAAGATCCTACAAGCTGTGCAGGCAAAACCTAGCAGGAAAAAAAAACAACGCATAAAGAAAAATGGCCGGGCCAGG
TCATTGGCTGGGAAGTCTCAGCCATGCACGGACTCGTTTCCAGAGGTAATTATGAGCGCCTACCAGCCAGGCCACCC
AGCCGTGGGAGGAAGGGGGCGTGGCAAGGGGTGGGCACATTGGTGTCTGTGCGAAAGGAAAATTGACCCGGAAGTTC
CTGTAATAAATGTCACAATAAAACGAATGAATG
```

FIGURE 11

SEQ ID NO: 12

```
MHVRSLRAAAPHSFVALWAPLFLLRSALADFSLDNEVHSSFIHRRLRSQERREMQREILSILGLPHRPRPHLQGKHN
SAPMFMLDLYNAMAVEEGGGPGGQGFSYPYKAVFSTQGPPLASLQDSHFLTDADMVMSFVNLVEHDKEFFHPRYHHR
EFRFDLSKIPEGEAVTAAEFRIYKDYIRERFDNETFRISVYQVLQEHLGRESDLFLLDSRTLWASEEGWLVFDITAT
SNHWVVNPRHNLGLQLSVETLDGQSINPKLAGLIGRHGPQNKQPFMVAFFKATEVHFLEVLFQGPGSKQRSQNRSKT
PKNQEALRMANVAENSSSDQRQACKKHELYVSFRDLGWQDWIIAPEGYAAYYCEGECAFPLNSYMNATNHAIVQTLV
HFINPETVPKPCCAPTQLNAISVLYFDDSSNVILKKYRNMVVRACGCH
```

FIGURE 12

SEQ ID NO: 13

ORIGIN

```
   1 gcggggaagc agcagcggcc aggatgaatc ccaggtgctc tggagctgga tggtgaaggt
  61 cggcactctt caccctcccg agccctgccc gtctcggccc catgccccca ccagtcagcc
 121 ccgggccaca ggcagtgagc aggcacctgg gagccgaggc cctgtgacca ggccaaggag
 181 acgggcgctc cagggtccca gccacctgtc cccccatgg agctgaggcc ctggttgcta
 241 tgggtggtag cagcaacagg aaccttggtc ctgctagcag ctgatgctca gggccagaag
 301 gtcttcacca acacgtgggc tgtgcgcatc cctggaggcc cagcggtggc caacagtgtg
 361 gcacggaagc atgggttcct caacctgggc cagatcttcg gggactatta ccacttctgg
 421 catcgaggag tgacgaagcg gtccctgtcg cctcaccgcc cgcggcacag ccggctgcag
 481 agggagcctc aagtacagtg gctggaacag caggtggcaa agcgacggac taaacgggac
 541 gtgtaccagg agcccacaga ccccaagttt cctcagcagt ggtacctgtc tggtgtcact
 601 cagcgggacc tgaatgtgaa ggcggcctgg gcgcagggct acacagggca cggcattgtg
 661 gtctccattc tggacgatgg catcgagaag aaccacccgg acttggcagg caattatgat
 721 cctgggccca gttttgatgt caatgaccag gaccctgacc ccagcctcg gtacacacag
 781 atgaatgaca acaggcacgg cacacggtgt gcggggaag tggctgcggt ggccaacaac
 841 ggtgtctgtg gtgtaggtgt ggcctacaac gcccgcattg gagggtgcg catgctggat
 901 ggcgaggtga cagatgcagt ggaggcacgc tcgctgggcc tgaacccaa ccacatccac
 961 atctacagtg ccagctgggg ccccgaggat gacggcaaga cagtggatgg gccagcccgc
1021 ctcgccgagg aggccttctt ccgtgggtt agccagggcc gagggggct gggctccatc
1081 tttgtctggg cctcgggaa cggggccgg gaacatgaca gctgcaactg cgacggctac
1141 accaacagta tctacacgct gtccatcagc agcgccacgc agtttggcaa cgtgccgtgg
1201 tacagcgagg cctgctcgtc cacactggcc acgacctaca gcagtggcaa ccagaatgag
1261 aagcagatcg tgacgactga cttgcggcag aagtgcacgg agtctcacac gggcacctca
1321 gcctctgccc ccttagcagc cggcatcatt gctctcaccc tggaggccaa taagaacctc
1381 acatggcggg acatgcaaca cctggtggta cagacctcga agccagccca cctcaatgcc
1441 aacgactggg ccaccaatgg tgtgggccgg aaagtgagcc actcatatgg ctacgggctt
1501 ttggacgcag gcgccatggt ggcctggcc cagaattgga cacagtggcc ccccagcgg
1561 aagtgcatca tcgacatcct caccgagccc aaagacatcg ggaaacggct cgaggtgcgg
1621 aagaccgtga ccgcgtgcct gggcgagccc aaccacatca ctcggctgga gcacgctcag
1681 gcgcggctca ccctgtccta aatcgccgt ggcgacctgg ccatccacct ggtcagcccc
1741 atgggcaccc gctccaccct gctggcagcc aggccacatg actactccgc agatgggttt
1801 aatgactggg ccttcatgac aactcattcc tgggatgagg atccctctgg cgagtgggtc
1861 ctagagattg aaaacaccag cgaagccaac aactatggga cgctgaccaa gttcacccctc
1921 gtactctatg gcaccgcccc tgaggggctg cccgtacctc cagaaagcag tggctgcaag
1981 accctcacgt ccagtcaggc ctgtgtggtg tgcgaggaag gcttctccct gcaccagaag
2041 agctgtgtcc agcactgccc tccagggttc gcccccaag tcctcgatac gcactatagc
2101 accgagaatg acgtggagac catccgggcc agcgtctgcg cccctgcca cgcctcatgt
2161 gccacatgcc aggggccggc cctgacagac tgcctcagct gccccagcca cgcctccttg
2221 gaccctgtgg agcagacttg ctcccggcaa agccagagca gccgagagtc ccgccacag
2281 cagcagccac ctcggctgcc cccggagggtg gaggcggggc aacggctgcg ggcagggctg
2341 ctgccctcac acctgcctga ggtggtggcc ggcctcagct gcgccttcat cgtgctggtc
2401 ttcgtcactg tcttcctggt cctgcagctg cgctctggct ttagttttcg ggggggtgaag
2461 gtgtacacca tggaccgtgg cctcatctcc tacaagggggc tgcccctga agcctggcag
2521 gaggagtgcc cgtctgactc agaagaggac gagggccggg gcgagaggac cgcctttatc
2581 aaagaccaga gcgccctctg atgagcccac tgcccacccc ctcaagccaa tcccctcctt
2641 gggcactttt taattcacca aagtattttt ttatcttggg actgggtttg gaccccagct
2701 gggaggcaag agggtggag actgcttccc atcctaccct cgggcccacc tggccacctg
```

FIGURE 13

```
2761 aggtgggccc aggaccagct ggggcgtggg gagggccgta ccccaccctc agcaccccctt
2821 ccatgtggag aaaggagtga aacctttagg gcagcttgcc ccggccccgg ccccagccag
2881 agttcctgcg gagtgaagag gggcagccct tgcttgttgg gattcctgac ccaggccgca
2941 gctcttgccc ttccctgtcc ctctaaagca ataatggtcc catccaggca gtcggggct
3001 ggcctaggag atatctgagg gaggaggcca cctctccaag ggcttctgca ccctccaccc
3061 tgtcccccag ctctggtgag tcttggcggc agcagccatc ataggaaggg accaaggcaa
3121 ggcaggtgcc tccaggtgtg cacgtggcat gtggcctgtg gcctgtgtcc catgacccac
3181 ccctgtgctc cgtgcctcca ccaccactgg ccaccaggct ggcgcagcca aggccgaagc
3241 tctggctgaa ccctgtgctg gtgtcctgac caccctcccc tctcttgcac ccgcctctcc
3301 cgtcagggcc caagtccctg ttttctgagc ccgggctgcc tgggctgttg gcactcacag
3361 acctggagcc cctgggtggg tggtggggag gggcgctggc ccagccgcc tctctggcct
3421 cccacccgat gctgcttcc cctgtgggga tctcagggc tgtttgagga tatattttca
3481 ctttgtgatt atttcacttt agatgctgat gatttgtttt tgtattttta atggggtag
3541 cagctggact acccacgttc tcacacccac cgtccgccct gctcctccct ggctgccctg
3601 gccctgaggt gtgggggctg cagcatgttg ctgaggagtg aggaatagtt gagcccaag
3661 tcctgaagag gcgggccagc caggcgggct caaggaaagg gggtcccagt gggaggggca
3721 ggctgacatc tgtgtttcaa gtggggctcg ccatgccggg ggttcatagg tcactggctc
3781 tccaagtgcc agaggtgggc aggtggtggc actgagcccc cccaacactg tgccctggtg
3841 gagaaagcac tgacctgtca tgccccctc aaacctcctc ttctgacgtg cctttgcac
3901 ccctcccatt aggacaatca gtccctccc atctgggagt ccccttttct tttctaccct
3961 agccattcct ggtacccagc catctgccca ggggtgccc ctcctctccc atcccctgc
4021 cctcgtggcc agcccggctg gttttgtaag atgctgggtt ggtgcacagt gattttttc
4081 ttgtaattta aacaggccca gcattgctgg ttctatttaa tggacatgag ataatgttag
4141 aggttttaaa gtgattaaac gtgcagacta tgcaaaccag
``` proprotein    289..2598
    /gene="FURIN"
    /product="furin proprotein"
mat_peptide    538..2598
    /gene="FURIN"
    /product="furin"

FIGURE 13 cont.

SEQ ID NO: 14

```
ORIGIN
        1 melrpwllwv vaatgtlvll aadaqgqkvf tntwavripg gpavansvar khgflnlgqi
       61 fgdyyhfwhr gvtkrslsph rprhsrlqre pqvqwleqqv akrrtkrdvy qeptdpkfpq
      121 qwylsgvtqr dlnvkaawaq gytghgivvs ilddgieknh pdlagnydpg asfdvndqdp
      181 dpqprytqmn dnrhgtrcag evaavanngv cgvgvaynar iggvrmldge vtdavearsl
      241 glnpnhihiy saswgpeddg ktvdgparla eeaffrgvsq grgglgsifv wasgnggreh
      301 dscncdgytn siytlsissa tqfgnvpwys eacsstlatt yssgnqnekq ivttdlrqkc
      361 teshtgtsas aplaagiial tleanknltw rdmqhlvvqt skpahlnand watngvgrkv
      421 shsygyglld agamvalaqn wttvapqrkc iidiltepkd igkrlevrkt vtaclgepnh
      481 itrlehaqar ltlsynrrgd laihlvspmg trstllaarp hdysadgfnd wafmtthswd
      541 edpsgewvle ientseanny gtltkftlvl ygtapeglpv ppessgcktl tssqacvvce
      601 egfslhqksc vqhcppgfap qvldthyste ndvetirasv capchascat cqgpaltdcl
      661 scpshasldp veqtcsrqsq ssresppqqq pprlppevea gqrlragllp shlpevvagl
      721 scafivlvfv tvflvlqlrs gfsfrgvkvy tmdrglisyk glppeawqee cpsdseedeg
      781 rgertafikd qsal
```

FIGURE 14

SEQ ID NO: 15

```
   1 gcggggaagc agcagcggcc aggatgaatc ccaggtgctc tggagctgga tggtgaaggt
  61 cggcactctt caccctcccg agccctgccc gtctcggccc catgccccca ccagtcagcc
 121 ccgggccaca ggcagtgagc aggcacctgg gagccgaggc cctgtgacca ggccaaggag
 181 acgggcgctc cagggtccca gccacctgtc cccccatgg agctgaggcc ctggttgcta
 241 tgggtggtag cagcaacagg aaccttggtc ctgctagcag ctgatgctca gggccagaag
 301 gtcttcacca acacgtgggc tgtgcgcatc cctggaggcc cagcggtggc caacagtgtg
 361 gcacggaagc atgggttcct caacctgggc cagatcttcg gggactatta ccacttctgg
 421 catcgaggag tgacgaagcg gtccctgtcg cctcaccgcc cgcggcacag ccggctgcag
 481 agggagcctc aagtacagtg gctggaacag caggtggcaa agcgacggac taaacgggac
 541 gtgtaccagg agcccacaga ccccaagttt cctcagcagt ggtacctgtc tggtgtcact
 601 cagcgggacc tgaatgtgaa ggcggcctgg gcgcagggct acacagggca cggcattgtg
 661 gtctccattc tggacgatgg catcgagaag aaccacccgg acttggcagg caattatgat
 721 cctggggcca gttttgatgt caatgaccag gaccctgacc ccagcctcg gtacacacag
 781 atgaatgaca acaggcacgg cacacggtgt gcggggaag tggctgcggt ggccaacaac
 841 ggtgtctgtg tgtaggtgt ggcctacaac gcccgcattg gagggtgcg catgctggat
 901 ggcgaggtga cagatgcagt ggaggcacgc tcgctgggcc tgaaccccaa ccacatccac
 961 atctacagtg ccagctgggg ccccgaggat gacggcaaga cagtggatgg ccagcccgc
1021 ctcgccgagg aggccttctt ccgtggggtt agccagggcc gagggggct gggctccatc
1081 tttgtctggg cctcggggaa cggggccgg gaacatgaca gctgcaactg cgacggctac
1141 accaacagta tctacacgct gtccatcagc agcgccacgc agtttggcaa cgtgccgtgg
1201 tacagcgagg cctgctcgtc cacactggcc acgacctaca gcagtggcaa ccagaatgag
1261 aagcagatcg tgacgactga cttgcggcag aagtgcacgg agtctcacac gggcacctca
1321 gcctctgccc cttagcagc cggcatcatt gctctcaccc tggaggccaa taagaacctc
1381 acatgcgggg acatgcaaca cctggtggta cagacctcga agccagccca cctcaatgcc
1441 aacgactggg ccaccaatgg tgtgggccgg aaagtgagcc actcatatgg ctacgggctt
1501 t-ggacgcag cgccatggt ggccctggcc cagaattgga ccacagtggc ccccagcgg
1560 aagtgcatca tcgacatcct caccgagccc aaagacatcg gaaacggct cgaggtgcgg
1620 aagaccgtga ccgcgtgcct gggcgagccc aaccacatca ctcggctgga gcacgctcag
1680 gcgcggctca ccctgtccta aatcgccgt ggcgacctgg ccatccacct ggtcagcccc
1740 atgggcaccc gctccaccct gctggcagcc aggccacatg actaccgc agatgggttt
1800 aatgactggg ccttcatgac aactcattcc tgggatgagg atccctctgg cgagtgggtc
1860 ctagagattg aaaacaccag cgaagccaac aactatggga cgctgaccaa gttcacctc
1920 gtactctatg gcaccgcccc tgaggggctg cccgtacctc cagaaagcag tggctgcaag
1980 accctcacgt ccagtcaggc ctgtgtggtg tgcgaggaag cttctccct gcaccagaag
2040 agctgtgtcc agcactgccc tccagggttc gcccccaag tcctcgatac gcactatagc
2100 accgagaatg acgtggagac catccgggcc agcgtctgcg cccctgcca cgcctcatgt
2160 gccacatgcc aggggccggc cctgacagac tgcctcagct gccccagcca cgcctccttg
2220 gaccctgtgg agcagacttg ctcccggcaa agccagagca gccgagagtc cccgccacag
2280 cagcagccac ctcggctgcc cccggaggtg gaggcgggc aacggctgcg ggcagggctg
2340 ctgccctcac acctgcctga ggtggtggcc ggcctcagct gcgccttcat cgtgctggtc
2400 ttcgtcactg tcttcctggt cctgcagctg cgctctggct ttagtttcg gggggtgaag
2460 gtgtacacca tggaccgtgg cctcatctcc tacaagggc tgcccctga agcctggcag
2520 gaggagtgcc cgtctgactc agaagaggac gagggccggg gcgagaggac cgcctttatc
2580 aaagaccaga gcgccctctg atgagcccac tgcccacccc ctcaagccaa tccctcctt
2640 gggcactttt taattcacca aagtatttt ttatcttggg actgggttg gacccagct
```

FIGURE 15

```
2700 gggaggcaag aggggtggag actgcttccc atcctaccct cgggcccacc tggccacctg
2760 aggtgggccc aggaccagct ggggcgtggg gagggccgta ccccaccctc agcacccctt
2820 ccatgtggag aaaggagtga aacctttagg gcagcttgcc ccggcccgg ccccagccag
2880 agttcctgcg gagtgaagag gggcagccct tgcttgttgg gattcctgac ccaggccgca
2940 gctcttgccc ttccctgtcc ctctaaagca ataatggtcc catccaggca gtcgggggct
3000 ggcctaggag atatctgagg gaggaggcca cctctccaag ggcttctgca ccctccaccc
3060 tgtcccccag ctctggtgag tcttggcggc agcagccatc ataggaaggg accaaggcaa
3120 ggcaggtgcc tccaggtgtg cacgtggcat gtggcctgtg gcctgtgtcc catgacccac
3180 ccctgtgctc cgtgcctcca ccaccactgg ccaccaggct ggcgcagcca aggccgaagc
3240 tctggctgaa ccctgtgctg gtgtcctgac caccctcccc tctcttgcac ccgcctctcc
3300 cgtcagggcc caagtccctg ttttctgagc ccgggctgcc tgggctgttg gcactcacag
3360 acctggagcc cctgggtggg tggtggggag gggcgctggc ccagccggcc tctctggcct
3420 cccacccgat gctgctttcc cctgtgggga tctcaggggc tgtttgagga tatattttca
3480 ctttgtgatt atttcacttt agatgctgat gatttgtttt tgtattttta atggggtag
3540 cagctggact acccacgttc tcacaccccac cgtccgccct gctcctccct ggctgccctg
3600 gccctgaggt gtggggctg cagcatgttg ctgaggagtg aggaatagtt gagccccaag
3660 tcctgaagag gcgggccagc caggcgggct caaggaaagg gggtcccagt gggaggggca
3720 ggctgacatc tgtgtttcaa gtgggctcg ccatgccggg ggttcatagg tcactggctc
3780 tccaagtgcc agaggtgggc aggtggtggc actgagcccc cccaacactg tgccctggtg
3840 gagaaagcac tgacctgtca tgcccccctc aaacctcctc ttctgacgtg ccttttgcac
3900 ccctcccatt aggacaatca gtccctccc atctgggagt cccttttct tttctaccct
3960 agccattcct ggtacccagc catctgccca ggggtgcccc ctcctctccc atcccctgc
4020 cctcgtggcc agcccggctg gttttgtaag atgctgggtt ggtgcacagt gattttttc
4080 ttgtaattta aacaggccca gcattgctgg ttctatttaa tggacatgag ataatgttag
4140 aggttttaaa gtgattaaac gtgcagacta tgcaaaccag
```

A deletion of a single nucleotide (T) at position 1502 (marked by a hyphen in sequence 15) results in the synthesis of a mutant furin that lacks any proteolytic activity. (see Takahashi et al. *Biochem. Biophys. Res. Commun.* 1993; 195:1019-1026).

**FIGURE

METHOD OF ENHANCING RECOMBINANT PROTEIN PRODUCTION

CROSS REFERENCE TO PRIOR APPLICATIONS

This application is a Continuation of PCT application number PCT/CA2008/000998, filed May 26, 2008, which claims priority from U.S. provisional patent application No. 60/940,256, filed May 25, 2007. The disclosures of such prior applications are incorporated herein in their entirety.

FIELD OF THE INVENTION

This invention relates to a method of enhancing the production of recombinant proteins by inhibiting the activity of proprotein convertases on the recombinant protein produced. In particular, the invention provides materials and methods for the increased production of recombinant BMPs in mammalian cell systems through the inhibition of proprotein convertase activity or by altering the expressed transgene so that the recombinant protein resists convertase cleavage which is optionally followed by the post secretion conversion of the recombinant proproteins to mature recombinant proteins.

BACKGROUND OF THE INVENTION

Recombinant Protein Production

To date, more than 130 proteins with human therapeutic use have entered the market. Only a small number of proteins are expressed in their native cell type under physiological conditions in amounts that permit convenient purification of the relatively large quantities required for research and clinical use. For instance, bone contains very low amounts of native bone morphogenetic proteins (BMPs), a family of proteins members of which are used clinically to promote bone repair. There are methods that exist to extract and purify biologically active BMPs from bone, but these methods are time-consuming, labor intensive, and most importantly, result in a very low yield: starting from 15 kg raw bone, final yield is around 0.5 g of partially purified BMPs (see Urist et al. *Methods Enzymol* 1987; 146:294-312 and Hu et al. *Growth Factors* 2004; 22:29-33). Therefore, various expression systems have been developed to produce recombinant proteins. Single cell expression systems have used a variety of hosts including bacteria, baculovirus-infected insect cells, yeast, and mammalian cells.

In bacteria based expression systems most proteins are produced at a relatively large volume compared to other single cell expression systems. However, the bacterial expression system lacks the ability to modify proteins, and hence fails to generate dimerized, correctly folded, and glycosylated functional forms of the mature proteins. Extensive dimerization and renaturation processes are thus often required before the recombinant proteins can be used. (Cleland, 1993, In Protein Folding In Vivo and In Vitro: pp. 1-21). Further, the recovered recombinant protein is usually contaminated with endotoxin/pyrogen that makes proteins for pharmaceutical/diagnostic use extremely difficult to validate (Walsh and Headon, 1994, In "Protein Biotechnology", pp. 118-162).

Recombinant DNA technology allows mammalian cells that usually grow well in culture to produce heterologous proteins, or proteins not normally synthesized by these cells. Genetic engineering allows high expression of the gene coding the protein of interest using vectors that are designed to replicate foreign DNA, and control transcription and translation of the introduced gene. Cultivated mammalian cells have become the dominant system for the production of recombinant proteins for clinical applications because of their proper protein folding, assembly, and post-translational modification (Wurm *Nat Biotechnol* 2004; 22:1393-1398) The quality and activity of a protein can be superior when expressed in mammalian cells versus other hosts such as bacteria and insect cells.

Mammalian expression systems are relatively costly to maintain in comparison to other expression systems and in general the amounts of protein produced are lower than in bacterial systems (for review see Wurm *Nat Biotechnol* 2004; 22:1393-1398). The productivity of recombinant cell lines has increased dramatically in the past 20 years. In the 1980s, mammalian cells typically reached a density of about $2 \times 10^6$ cells/ml with a batch process production phase of about 7 days and a specific productivity slightly below 10 pg/cell/day. In a process reported in 2004, the culture was started at a low cell density of about 100,000 cells/ml and rapidly grew into a density of more than $10 \times 10^6$ cells/ml. A high level of cell viability was maintained for almost 3 weeks with a specific productivity up to approximately 90 pg/cell/day (Wurm *Nat Biotechnol* 2004; 22: 1393-1398). The high yield obtained in today's processes are the result of years of research that led to a better understanding of gene expression, metabolism, growth and apoptosis in mammalian cells. Overall efforts have led to improvements in vectors, host cell engineering, medium development, screening methods, and process engineering and development.

Other single cell expression systems such as insect and fungal expression systems have also been used for recombinant protein production. However, these expression systems are considered to suffer from similar problems as does the bacterial expression system (misfolding, improper processing) (Martegani et al., Appl. Microbiol. Biotechnol. 1992; 37:604-608). Recombinant proteins expressed by insect cells are often glycosylated incompletely or have different glycosylation patterns from those produced by mammalian cells. Some strains of yeast cells cannot perform N-linked or O-linked glycosylation or both (for a review of insect cell culture, see Goosen, et al., Insect Cell Culture Engineering. New York: M. Dekker, 1993, and for yeast expression system, see Chiba and Jigami Curr Opin Chem Biol. 200; 11:670-676).

Besides single cell systems, multi-cellular organisms such as transgenic plants or animal have been used for transgenic protein production.

Disadvantages of transgenic plants include low accumulation level of recombinant protein, insufficient information on post-translational events (e.g., unknown glycosylation pattern), and the lack of data on downstream processing (for reviews see Boehm, *Ann. N.Y. Acad. Sci.* 2007: 1102; 121-134, Horn et al. Plant Cell Rep. 2004: 22; 711 and Kusnadi et al. *Biotechnol. Bioeng.* 1997: 56; 473-484).

One major concern with transgenic animals is the possibility of disease transmission from animal to human. Other challenges such as inefficient introduction of foreign DNA into host animal and gaps in our knowledge of embryo genomics and epigenetic changes need to be overcome in order to optimize the transgenic animal systems for recombinant protein production (for reviews see Niemann and Kues Reprod. Fertil. Dev. 2007: 19; 762-770; Velander et al. *Scientific American* 1997: 276; 70-74, Pollock et al. *J. Immunol. Methods* 1999: 231; 147-157).

Bone Morphogenetic Proteins

The bone morphogenetic proteins (also called bone morphogenic proteins or BMPs) are members of the transforming growth factor beta (TGFβ) superfamily of secreted growth and differentiation factors. The BMP subfamily of the TGFβ superfamily comprises at least fifteen proteins, including BMP-2, BMP-3 (also known as osteogenin), BMP-3b (also known as growth and differentiation factor 10, GDF-10), BMP-4, BMP-5, BMP-6, BMP-7 (also known as osteogenic protein-1, OP-1), BMP-8 (also known as osteogenic protein-2, OP-2), BMP-9, BMP-10, BMP-11 (also known as growth and differentiation factor 8, GDF-8, or myostatin), BMP-12 (also known as growth and differentiation factor 7, GDF-7), BMP-13 (also known as growth and differentiation factor 6, GDF-6), BMP-14 (also known as growth and differentiation factor 5, GDF-5), and BMP-15 (for a review, see e.g., Azari et al. Expert Opin Invest Drugs 2001; 10:1677-1686).

BMPs are synthesized as large precursor molecules consisting of an amino terminal signal peptide, a pro-domain, and a carboxy terminal domain harboring the mature protein. The amino-terminal signal peptide and pro-domain regions of the various BMPs vary in size and amino acid sequence, whereas the mature domain shows a greater degree of sequence identity among BMP subfamily members. The mature domain is ordinarily cleaved from the pro-domain by one or more of the basic proprotein convertases, such as furin, to yield an active mature polypeptide of between 110-140 amino acids in length. The pro-domain appears to be required for normal synthesis and secretion of BMP polypeptides (for a review, see e.g., Azari et al. Expert Opin Invest Drugs 2001; 10:1677-1686; and Hoffman et al. Appl Microbiol Biotech 2001; 57:294-308, Israel et al. Growth Factors 1992; 7:139-150).

The individual members of the BMP family can be divided into several subfamilies within which the sequence of their mature carboxy terminal protein domain is well conserved. BMP-2 and -4 have greater than 90% sequence identity and BMP-5, 6, 7 and 8 have 70 to 90% sequence identity within these subfamilies. Between these 2 groups there is a 55 to 65% sequence identity of the mature proteins. In contrast the mature forms of the TGF-β, the activin and the inhibin families share less that 50% sequence identity with these BMPs (Ozkaynak et al. J Biol Chem. 1992; 267:25220-25227).

The highly conserved mature region of BMPs contain seven highly conserved cysteine residues. Six of these cysteine residues are implicated in the formation of intrachain disulfide bonds that form a rigid "cysteine knot" structure. The seventh cysteine is involved in the formation of homodimers and heterodimers via an interchain disulphide bond (for a review, see e.g., Azari et al. Expert Opin Invest Drugs 2001; 10:1677-1686 and Hoffman et al. Appl Microbiol Biotech 2001; 57:294-308).

During intracellular processing, the mature domain of BMPs are cleaved from the pro-domain. The mature BMP polypeptides form either homodimers (made up of monomers of a single BMP subfamily member) or heterodimers (made up of monomers of two different BMP subfamily members) connected by one disulfide bond in a head-to-tail arrangement (for a review, see e.g., Azari et al. Expert Opin Invest Drugs 2001; 10:1677-1686 and Hoffman et al. Appl Microbiol Biotech 2001; 57:294-308). Both BMP homodimers (e.g., BMP-2/-2 homodimers) and heterodimers (e.g., BMP-4/-7 heterodimers) are active in vivo (see, e.g., Aono et al. Biochem Biophys Res Comm. 1995; 210:670-677; Kusumoto et al. Biochem Biophys Res Comm 1997; 239:575-579; and Suzuki et al. Biochem Biophys Res Comm 1997; 232:153-156). Under certain conditions, heterodimers of BMP-2, BMP-4, and BMP-7 (e.g., BMP-4/-7 heterodimers and BMP-2/-7 heterodimers) are more active oseoinductive agents than the corresponding homodimers (see, e.g., U.S. Pat. No. 6,593,109 and Aono et al. Biochem Biophys Res Comm. 1995; 210:670-677).

BMPs are glycosylated proteins, with the mature protein having between 1 and 3 potential glycosylation sites (Celeste et al. PNAS 1990; 87:9843-9847). A glycosylation site in the center of the mature protein domain is shared by BMPs 2, 4, 5, 6, 7, and 8 but is absent in BMP-3 (Ozkayanak et al. J. Biol. Chem. 1992; 267:25220-25227). Chemical deglycosylation of BMP-2 and BMP-7 results in reduced activity of these proteins (Sampath et al. J. Biol. Chem. 1990; 265:13198-13205), indicating that proper glycosylation is required for full BMP activity.

Active, mature BMP polypeptides bind to, and initiate a cell signal through, a transmembrane receptor complex formed by types I and II serine/threonine kinase receptor proteins. Type I (BMP receptor-1A or BMP receptor-1B) and Type II (BMP receptor II) receptor proteins are distinguished based upon molecular weight, the presence of a glycine/serine-rich repeat, and the ability to bind to specific ligands. Individual receptors have low affinity binding for BMPs, while heteromeric receptor complexes bind to BMPs with high affinity (for a review, see e.g., Azari et al. Expert Opin Invest Drugs 2001; 10:1677-1686 and Hoffman et al. Appl Microbiol Biotech 2001; 57:294-308).

BMPs have been shown to regulate the growth and differentiation of several cell types. They stimulate matrix synthesis in chondroblasts; stimulate alkaline phosphatase activity and collagen synthesis in osteoblasts, induce the differentiation of early mesenchymal progenitors into osteogenic cells (osteoinductive), regulate chemotaxis of monocytes, and regulate the differentiation of neural cells (for a review, see e.g., Azari et al. Expert Opin Invest Drugs 2001; 10:1677-1686 and Hoffman et al. Appl Microbiol Biotech 2001; 57:294-308).

One of the many functions of BMP proteins is to induce cartilage, bone, and connective tissue formation in vertebrates. The most osteoinductive members of the BMP subfamily are BMP-2, BMP-4, BMP-6, BMP-7, BMP-9, and BMP-14 (see, e.g., Hoffman et al. Appl Microbiol Biotech 2001; 57:294-308, Yeh et al. J Cellular Biochem. 2005; 95-173-188 and Boden. Orthopaedic Nursing 2005; 24:49-52). This osteoinductive capacity of BMPs has long been considered very promising for a variety of therapeutic and clinical applications, including fracture repair; spine fusion; treatment of skeletal diseases, regeneration of skull, mandibullar, and bone defects; and in oral and dental applications such as dentogenesis and cementogenesis during regeneration of periodontal wounds, bone graft, and sinus augmentation. Currently, recombinant human BMP-2 sold as InFUSE™ by Medtronic and recombinant human BMP-7 sold as OP-1® by Stryker are FDA approved for use in spinal fusion surgery, for repair of fracture non-unions and for use in oral surgery.

Other therapeutic and clinical applications for which BMPs are being developed include; Parkinson's and other neurodegenerative diseases, stroke, head injury, cerebral ischemia, liver regeneration, acute and chronic renal injury (see, e.g., Azari et al. Expert Opin Invest Drugs 2001; 10:1677-1686; Hoffman et al. Appl Microbiol Biotech 2001; 57:294-308; Kopp Kidney Int 2002; 61:351-352; and Boden. Orthopaedic Nursing 2005; 24:49-52). BMPs also have potential as veterinary therapeutics and as research or diagnostic reagents (Urist et al. Prog Clin Biol Res. 1985; 187: 77-96).

Production of Recombinant BMPs

The widespread therapeutic use of BMPs has been hindered by difficulties in obtaining large quantities of pure, biologically active BMP polypeptide, either from endogenous or recombinant sources at a cost-effective price. As noted above bone and other tissues contain very low concentrations of mature BMPs and BMP precursor molecules. While methods exist to extract biologically active BMPs from bone, these are time consuming methods with non-economical yields (Hu et al. *Growth Factors* 2004; 22: 29-33).

Recombinant BMPs have been produced using bacterial expression systems such as *E. coli*. However, active BMPs are obtained only following an extensive renaturation and dimerization process in vitro. In this process, monomeric BMP must first be purified, then renatured in the presence of chaotropic agents, and finally purified to remove unfolded BMP monomers and other contaminating *E. coli* proteins. This process is complex, time consuming, and costly, and often has a low yield of active dimer compared to total monomer produced (for a review, see e.g., Hoffman et al. *Appl Microbiol Biotech* 2001; 57:294-308). Furthermore, BMPs produced by such methods are not glycosylated, and therefore would not be expected to be fully potent.

Attempts at recombinant production of BMP in insect cell culture have resulted in predominantly intracellular BMP accumulation with minimal recovery of active BMP from the culture media (Maruoka et al. Biochem Mol Biol Int 1995; 35:957-963 and Hazama et al. *Biochem Biophys Res Comm* 1995; 209:859-866).

Commercially available BMP preparations are based upon mammalian cell expression systems. Human BMP-2 has been expressed in CHO (Chinese hamster ovary) cells; human BMP-4 has been expressed in a mouse myeloma cell line (NS0) and in a human embryonic kidney cell lines (HEK 292); and human BMP-7 has been expressed in a primate cell line (BS) and in CHO cells (for a review, see e.g., Hoffman et al. *Appl Microbiol Biotech* 2001; 57:294-308). However, such eukaryotic expression systems generally have lower productivity and yield compared to prokaryotic systems. Further, BMPs appear to be produced inefficiently in eukaryotic systems resulting in much lower levels of production compared to that achieved for other proteins in the same systems (Israel et al. *Growth Factors* 1992; 7:139-50). Due to these low yields, recombinant BMPs are currently very expensive.

Thus, a need exists in the art for materials and methods for the production of recombinant, active BMPs on a large scale. In particular, a need exists for materials and methods for efficient, lost-cost production of biologically potent BMPs.

Current Methods to Enhance Recombinant Protein Production

Efforts to improve productivity in mammalian cell systems can be divided into 2 areas. The first involves increasing or maintaining transcription of the transgenes by methods such as improving vector design, plasmid integration and optimizing the chromosomal environment. The second is maximizing the translational or secretory capacity of the host cells through methods such as host cell engineering, media optimization, and improved bioreactor design and feeding methods (for review see Wurm *Nature Biotechnol.* 2004; 22:1393-1398, Barnes & Dickson *Curr. Opin. Biotechnol.* 2006; 17:381-386).

Many stimulating chemicals have been added to the culture systems to improve productivity. Examples include butyrate (Lamotte et al. *Cytotechnology,* 1999; 29: 55-64), which enhances gene expression by inhibiting histone deacetylases, pentanoic acid (Liu et al. *J. Biosci. Bioeng.* 2001; 91: 71-75) and cysteamine (Yoon et al. *Biotechnol. Lett.* 1999; 20: 101-104).

Role of Pro-Domains in Protein Processing and Secretion

Many proteins including those with therapeutic applications are produced in nature as pro-proteins. Pro-proteins are larger precursors of the mature protein. The pro-protein consists of the pro-domain and the mature domain. The pro-domain of a protein plays an important role in the processing and secretion of the mature protein. The best understood role for a pro-protein is that derived from studies of pro-hormones and pro-enzymes, where cleavage is associated with the mature protein activation. Pro-forms of growth factors have received intensive scientific attention recently because pro-domain is found to play essential roles in the maturation of the precursor proteins.

Studies on the role of the prodomain of many diverse proteins have demonstrated that they play a role in the processing and secretion of these proteins. The prodomain of brain derived neurotrophic factor (BDNF) interacts with sortillin an intracellular chaperone which controls the sorting of BDNF to the regulated secretory pathway. A single amino acid mutation in the prodomain results in defective regulated secretion of BDNF by altering its interaction with sortillin (Chen et al. *J. Neuroscience* 2005; 25:6156-66). The prodomain of Conotoxin-TxVI shields the hydrophobic surfaces of the mature protein, which would otherwise target it for intracellular degradation, permitting its secretion (Conticello et al. *J. Biol. Chem.* 2003; 278:26311-26314). The matrix metalloproteinase BMP-1 was shown to more rapidly become secreted when the furin cleavage site RSRR in its prodomain was mutated to RSAA (Leighton and Kadler *J. Biol. Chem.* 2003: 278:18478-18484). When the furin cleavage site for nerve growth factor (NGF) was mutated cleavage occurred at an alternate site but the alternate NGF did not undergo regulated secretion (Lim et al. *BBRC* 2007; 361:599-604).

The pro-domain of the TGF-β family members, including all BMPs, is believed to have several functions. It appears to be required for the folding, dimerization and secretion of mature active TGF-β and activin (Gray & Mason. *Science* 1990; 247:1328-1330). Further, in the case of TGF-β, continued association of the N-terminal and C-terminal domain after proteolytic cleavage renders the complex inactive or latent (Gentry et al. *Biochemistry* 1990; 29:6851-6857). ProBMP-4 has been reported to be biologically inactive (Cui et al. *EMBO J.* 1998; 17:4735-4743), although *E. coli* produced proBMP-2 has been reported to posses biological activity (Hillger et al. *J. Biol. Chem.* 2005; 280:14974-14980) and CHO cell produced rh-proBMP-9 has similar activity as mature rhBMP-9 in various in vitro assays (Brown et al. *J. Biol. Chem.* 2005; 280:25111-25118).

Comparison of the production, processing and secretion of mouse and human BMP-15 produced by transfected HEK293 cells indicated that human BMP-15 (hBMP-15) was secreted into the conditioned medium; however mouse BMP-15 (mBMP-15) was not secreted. Unlike hBMP-15, mBMP-15 pro-protein is not cleaved into a mature protein after proteolytic processing, but is targeted for intracellular degradation. When the hBMP-15 pro-domain was fused with the mature region of mBMP-15, there was secretion of mBMP-15 mature protein into the conditioned cell culture media (Hashimoto, et al. *Proc. Natl. Acad. Sci.* 2005; 102: 5426-543). Thus, in the case of BMP-15 at least, it appears that the proper processing of the pro-protein is significant for the secretion of the mature proteins.

When a Val residue is exchanged to a Gly at AA position 130 in the pro-domain of BMP-7 normal levels of the precursors and mature protein were found in the *Xenopus* oocyte lysates, indicating that stability and processing of the precursor are not affected by the mutation. However, there was a dramatically reduced amount of both the pro-domain peptide and the mature protein in the conditioned medium (Dick, et al. *Development,* 2000; 127: 343-354). In-frame deletion of the pro-peptide of BMP-2 yielded a polypeptide that was not secreted from the cell, suggesting that the pro-peptide may therefore be involved in processing and secretion of mature BMP-2 protein (Israel et al. *Growth Factors* 1992; 7: 139-150). A hybrid of the pro-domain of BMP-2 fused to the mature region of BMP-4 has been constructed and shown to secrete mature biologically active BMP-4 at an enhanced level (Hammonds et al. *Mol Endocrinol* 1991; 5: 149-155). These results indicate that the prodomain plays an important role in the folding and secretion of proteins.

Limited endoproteolysis of the prodomain of a protein is a general mechanism generating a diversity of biologically active peptides and proteins in all eukaryotic phyla. This is performed by a small number of Ca(2+)-dependent serine proteases collectively called proprotein convertases (PCs) (for reviews see Seidah & Chretien *Curr Opin Biotechnol* 1997; 8:602-607, Taylor et al. *FASEB J* 2003; 17:1215-1227). These PC possess homology to the endoproteases subtilisin (bacteria) and kexin (yeast). This family of mammalians PCs is currently comprised of furin (also called paired basic amino-acid-cleaving enzyme (PACE)), PC1/PC3, PC2, PC4, PACE4, PC5/PC5A/PC6, PC5B/PC6B (a spice variant of PC5A) and PC7/PC8/lymphoma proprotein convertase. They share a high degree of amino-acid identity of 50-75% within their catalytic domains. Furin and PC7 are expressed ubiquitously, PACE-4, PC5A and PC5B are expressed at varying levels in many tissues while PC1, PC2, and PC4 are restricted to specific tissues (Dubois et al. *Am. J. Path.* 2001; 158:305-616).

One of the major recognition motifs for these enzymes involves cleavage at either specific single or pairs of basic residues of the general formula $(R/K)-X_n-(R/K)$, where $n=0$, 2, 4 or 6. Such sites are found in a variety of protein precursors in all eukaryotes, including those of endocrine and neural polypeptide hormones (including PTH, Insulin), enzymes (including furin, MMP-1, MMP-13), growth factors (including TGF-β1, BMP-2, BMP-4, BMP-7, PDGF, IGF-1, IGF-2, VEGF, FGF-23, EGF, PTHrP), receptors, adhesion molecules (including many integrins), viral glycoproteins, coagulation factors and even cell signaling molecules (see Seidah & Chretien *Curr Opin Biotechnol* 1997; 8:602-607, Khatib et al. *Am J Pathol* 2002; 160: 1921-1935, Taylor et al. *FASEB J* 2003; 17:1215-1227).

Both BMP-2 and BMP-4 posses 2 PC recognition sites, called the S1 (AA 278) and S2 (AA 245) sites, while BMP-7 possess only one recognition site, the S2 site (Sopory et al. *J Biol. Chem.* 2006; 281:34021-34031). ProBMP-4 is cleaved first at the S1 site to produce the mature BMP-4 molecule and the pro-domain. The prodomain associates with the mature protein non-covalently until it is cleaved at the S2 site. While the prodomain remains associated with the mature protein the complex is targeted for intracellular degradation (Degnin et al. *Mo Biol. Cell* 2004; 15:5012-5020.). Further it has been shown that mutation of the S2 site results in tissue specific loss of BMP-4 activity (Goldman et al. *Development* 2006; 133:1933-1942). Both the prodomain and mature BMP-2 are secreted into conditioned medium of CHO cells expressing proBMP-2, however approximately 5 times more prodomain than mature protein was detected in the medium (Israel et al. *Growth Factors* 1992; 7:130-150).

ProBMP-4 can be cleaved by furin, PC6, PC7 and PACE 4 in vitro while in vivo studies suggest that either furin, PC6, and or PACE 4 is the PC responsible for cleavage intracellularly (Cui et al. *EMBO J.* 1998; 17: 4735-4743, Tsuji et al. *J. Biochem* 1999; 126:591-603). Studies on the efficiency of the different PC to cleave proTGF-β1 in cell systems identified the order of activity from most to least as furin>PC5B=PACE-4>PC7>PC-1 while PC2 and PC5A had little effect on the proTGF-β1 protein (Dubois et al. *Am. J. Path.* 2001; 158:305-616).

The human colon carcinoma LoVo cell line possesses a point mutation in the furin gene (fur) which results in LoVo cells completely lacking furin enzymatic activity (Takahashi et al. *Biochem. Biophys. Res. Comm.* 1993; 195:1019-1026). When these cells are transfected with TGF-β1 they secrete only proTGF-β1 which is inactive (Dubois et al. *J. Biol. Chem.* 1995; 270:10618-10624). When these cells are co-transfected with various proprotein convertases, the degree of cleavage of proTGF-β1 varied depending on the PC co-transfected with the TGF-β1 (Dubois et al. *Am. J. Path.* 2001; 158:305-616).

A CHO-derived cell line that over-expresses furin when transfected with cDNA coding for full length TGF-β1 or von Willebrand Factor (vWF) demonstrated increased production of active TGF-β1 or vWF (Ayoubi et al. *Mol. Biol. Rep.* 1996; 23:87-95), however no effort was made to determine whether the total amount of recombinant protein produced (active+inactive) was more or less than in CHO cells not over-expressing furin. When α1-antitrypsin Portland (α1-PDX), an inhibitor of furin was ectopically expressed in *Xenopus* embryos it blocked BMP-4 activity upstream of the receptor.

Israel and co-workers attempted to enhance the amount of mature BMP produced in CHO cells by using protease inhibitors, however they stated that they "were unable to increase the amount of BMP-2 mature protein by including a large number of different protease inhibitors in the culture medium." They did not report which inhibitors they tested (Israel et al. *Growth Factors* 1992; 7: 139-150).

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide a method of enhanced protein production. In particular, an object of the present invention is to provide a method of enhanced production of a protein that is a member of the transforming growth factor-β (TGF-β) superfamily, such as a bone morphogenetic protein (BMP).

In accordance with one aspect of the present invention, there is provided an in vitro method of producing a recombinant protein that comprises the step of expressing a gene encoding the protein in eukaryotic cells under conditions in which cleavage of the pro-domain of the protein is inhibited, altered or eliminated. The present invention is directed to a method in which secretion of recombinant proteins by eukaryotic cells is enhanced through the inhibition or alteration of proprotein convertase activity or susceptibility of the recombinant protein to cleavage by proprotein convertases at one or more sites in the protein sequence. This is based on the surprising and unexpected findings that hBMP synthesis and secretion from CHO cells was enhanced when furin-like protease activity was inhibited.

The term "altered" is used herein to refer to a change that results in reduced cleavage of the pro-domain of a protein in comparison to naturally occurring cleavage of the pro-domain or in a reduction in the number of cleavage sites within the prodomain.

In accordance with one embodiment of the present invention, the recombinant protein is a member of the TGF-β superfamily, such as a recombinant bone morphogenetic protein. In accordance with a specific embodiment the recombinant BMP is a recombinant human BMP. Further, in accordance with a preferred embodiment, the recombinant BMP is a recombinant BMP-2 or a recombinant BMP-7, such as a recombinant human BMP-2 or a recombinant human BMP-7.

Eukaryotic cells useful in the present invention include mammalian cells, such as, but not limited to CHO, COS, HEK, NS0, BHK, HELA, 3T3 or other cells commonly used by those skilled in the art to produce recombinant proteins.

In certain embodiments the proprotein convertase is a mammalian proprotein convertase, such as, but not limited to furin, PC5/6, PC7 or PACE4.

In accordance with an embodiment of the invention the proprotein convertase (PC) activity is inhibited by reducing the amount of proprotein convertase protein expressed in the cells. This is achieved, for example, by mutating the promoter for the proprotein convertase gene or by using one or more inhibitors of PC gene expression. In accordance with a specific embodiment the PC gene expression is inhibited through the use of antisense nucleic acids or interfering RNAs (RNAi).

In an alternative embodiment, the PC activity is inhibited through the mutation of the PC gene to produce a PC protease having reduced activity. In this embodiment the enzymatic activity of the mutated PC is reduced by at least 50%, or preferably by at least 80%.

In another alternative embodiment the PC activity is inhibited through the use of enzyme inhibitors. Such enzyme inhibitors can be, for example, small molecule inhibitors, PC enzyme analogs or fragments, anti-PC enzyme antibodies, or combinations thereof. In the specific example in which the enzyme inhibitor is a small molecule, it can be a peptide inhibitor, such as, for example, a poly-D-arginine (e.g., nona-D-arginine amide, 9DR).

In another alternative embodiment PC activity is inhibited by co-transfecting the cells with a PC inhibitor, such as, but not limited to, α1-PDX.

In another alternative embodiment the PC activity is inhibited through the use of a mutated gene that expresses the recombinant protein of interest such that the protein is resistant to PC cleavage of its prodomain at one or more cleavage sites. The mutated gene can include an in frame insertion or substitution that results in a protein that includes a cleavage site for a non-PC proteolytic enzyme (e.g., Factor Xa or PreScission).

In accordance with another aspect of the present invention there is provided an in vitro method of producing a recombinant protein that comprises the steps of: (a) expressing a gene encoding the protein in eukaryotic cells under conditions in which cleavage of the proprotein portion of the protein is altered, inhibited or eliminated; and (b) converting the secreted pro-protein or PC-resistant pro-proteins into mature proteins by the treatment with an appropriate protease during or following purification of the recombinant protein.

In accordance with another aspect of the present invention there is provided a genetically engineered cell, or cell line, that exhibits reduced expression of the PC gene in comparison to the wild-type cell or cell line. This cell or cell line is optionally engineered to express a recombinant proprotein of interest, such as a TGF-β proprotein (e.g., a proBMP).

In accordance with another aspect of the present invention there is provided a genetically engineered cell, or cell line, that expresses a modified proprotein convertase with altered activity in comparison to wild-type proprotein convertase. This cell or cell line is optionally engineered to express a recombinant proprotein of interest, such as a TGF-β proprotein (e.g., a proBMP).

In accordance with another aspect of the present invention there is provided a genetically engineered cell, or cell line, comprising a recombinant nucleic acid sequence that encodes a modified proprotein with altered susceptibility to proprotein convertase activity in comparison to the wild-type proprotein.

In accordance with another aspect of the present invention there is provided a genetically-engineered polynucleotide comprising: (i) a nucleic acid sequence encoding a recombinant BMP; (ii) an upstream promoter regulatory element that directs expression of the recombinant BMP; and (iii) a signal sequence that directs secretion of the recombinant BMP. The recombinant BMP can be a recombinant human BMP. The recombinant BMP can be a recombinant BMP-2 or a recombinant BMP-7, such as, for example, a recombinant human BMP-2 or a recombinant human BMP-7. The present invention also provides a mammalian cell, or cell line, that comprises this genetically-engineered polynucleotide. Also provided herein are methods for making this genetically-engineered nucleic acid sequence by joining a nucleic acid sequence encoding a recombinant BMP with a promoter sequence that directs expression of the recombinant BMP and with at least one signal sequence that provides secretion of the recombinant BMP.

BRIEF DESCRIPTION OF THE DRAWINGS

FIG. 1 depicts an exemplary nucleotide sequence for a human BMP-2 (SEQ ID NO: 1) derived from GenBank Accession number M22489.1.

FIG. 2 depicts an exemplary amino acid sequence for a human BMP-2 (SEQ ID NO: 2) derived from GenBank Accession number AAA51834.1.

FIG. 3 depicts an exemplary nucleotide sequence for a human BMP-7 (SEQ ID NO: 3) derived from GenBank Accession number NM_001719.1.

FIG. 4 depicts an exemplary amino acid sequence for a human BMP-7 (SEQ ID NO: 4) derived from GenBank Accession number NP_001719.1.

FIG. 5 depicts an exemplary nucleotide sequence for a human BMP-4 (SEQ ID NO: 5) derived from GenBank Accession number BC020546.2.

FIG. 6 depicts an exemplary amino acid sequence for a human BMP-4 (SEQ ID NO: 6) derived from GenBank Accession number AAH20546.1.

FIG. 7 depicts an exemplary nucleotide sequence encoding a human BMP-2 with a mutated S1 protease cleavage site which is resistant to furin but can be cleaved by the PreScission enzyme (SEQ ID NO: 7) derived originally from GenBank Accession number NM_001200.1.

FIG. 8 depicts an exemplary amino acid sequence for a human BMP-2 with a mutated S1 protease cleavage site which is resistant to furin but can be cleaved by the PreScission enzyme (SEQ ID NO: 8) derived originally from GenBank Accession number NP_001191.1.

FIG. 9 depicts an exemplary nucleotide sequence for a human BMP-2 with mutated S1 and S2 protease cleavage sites (SEQ ID NO: 9) derived originally from GenBank Accession number M22489.1.

FIG. 10 depicts an exemplary amino acid sequence for a human BMP-2 with mutated S1 and S2 protease cleavage sites (SEQ ID NO: 10) derived originally from GenBank Accession number AAA51834.1.

FIG. 11 depicts an exemplary nucleotide sequence for a human BMP-7 with a mutated protease cleavage site which is resistant to furin but can be cleaved by the PreScission enzyme (SEQ ID NO: 11) derived originally from GenBank Accession number NM_001719.1.

FIG. 12 depicts an exemplary amino acid sequence for a human BMP-7 with a mutated protease cleavage site which is resistant to furin but can be cleaved by the PreScission enzyme (SEQ ID NO: 12) derived originally from GenBank Accession number NP_001710.1.

FIG. 13 depicts an exemplary nucleotide sequence for human furin (SEQ ID NO: 13) derived originally from GenBank Accession number NM_002569.2.

FIG. 14 depicts an exemplary amino acid sequence for human furin (SEQ ID NO: 13) derived originally from GenBank Accession number NP_002560.1.

FIG. 15 depicts an exemplary nucleotide sequence for mutated furin cDNA that lacks enzymatic activity.

DETAILED DESCRIPTION OF THE INVENTION

Figure 16:
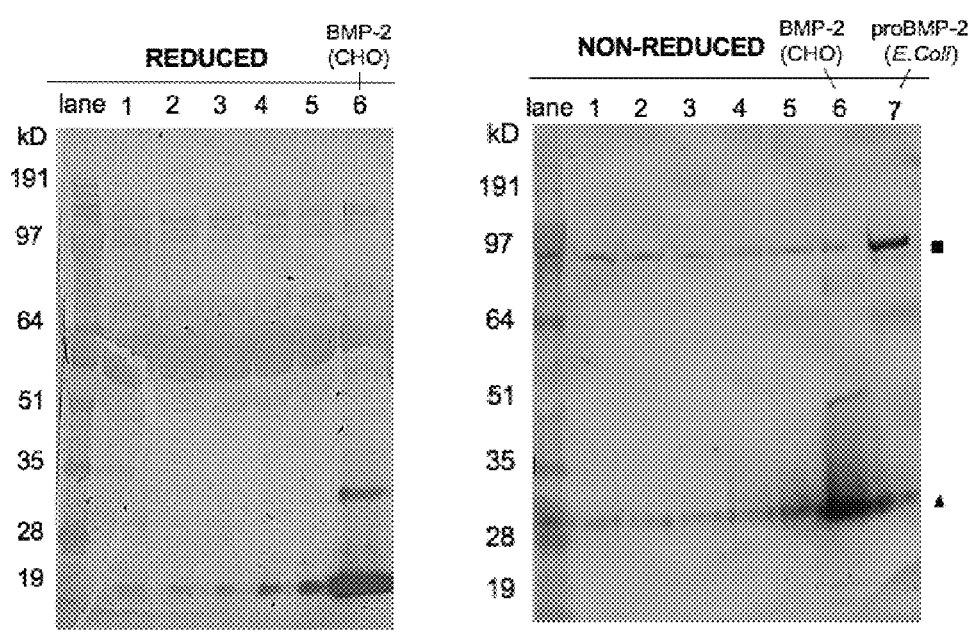
FIG. 16 depicts a BMP-2 Western blot of CHO-BMP-2 cell conditioned medium.

The present inventors have surprisingly found that large quantities of recombinant protein can be produced using eukaryotic cell systems by inhibiting or altering the cleavage of the pro-domain of the recombinant protein. Cleavage of the pro-domain can be reduced or eliminated, for example, by inhibition of proprotein convertase (PC) activity, by reduction of the amount PC enzyme present, or by mutation of the recombinant gene/protein such that the protein is resistant to PC cleavage. The methods of the present invention can be useful for rapid, cost-effective production of large quantities of recombinant proteins, such as recombinant BMPs. Such recombinant proteins can be used for a variety of therapeutic and clinical applications. For example recombinant BMPs can be useful in various therapeutic and clinical applications including, but not limited to, fracture repair; bone grafts; spine fusion; treatment of skeletal diseases, regeneration of skull, mandibular, and bone defects; oral and dental applications such as dentogenesis and cementogenesis during regeneration of periodontal wounds, bone graft, and sinus augmentation; Parkinson's and other neurodegenerative diseases; stroke; head injury; cerebral ischemia; liver regeneration; and acute and chronic renal injury.

In describing the present invention, specific reference is made to the application of the method to producing BMPs. However, the invention is not limited to methods for the production of BMPs. Rather, as would be readily appreciated to a worker skilled in the art, the method of the present invention is applicable to the production of any protein having a pro-domain that, under naturally occurring conditions, is cleaved via PC activity.

Definitions:

Unless defined otherwise, all technical and scientific terms used herein have the same meaning as commonly understood by one of ordinary skill in the art to which this invention belongs.

As used herein, the terms "bone morphogenetic protein" or "bone morphogenic protein" or "BMP" are used interchangeably and refer to any member of the bone morphogenetic protein (BMP) subfamily of the transforming growth factor beta (TGFβ) superfamily of growth and differentiation factors, including BMP-2, BMP-3 (also known as osteogenin), BMP-3b (also known as growth and differentiation factor 10, GDF-10), BMP-4, BMP-5, BMP-6, BMP-7 (also known as osteogenic protein-1, OP-1), BMP-8 (also known as osteogenic protein-2, OP-2), BMP-9, BMP-10, BMP-11 (also known as growth and differentiation factor 8, GDF-8, or myostatin), BMP-12 (also known as growth and differentiation factor 7, GDF-7), BMP-13 (also known as growth and differentiation factor 6, GDF-6), BMP-14 (also known as growth and differentiation factor 5, GDF-5), and BMP-15.

BMP subfamily members contain an amino terminal signal peptide of variable size, a pro-domain of variable size, and a carboxy terminal mature protein domain of approximately 110 to 140 amino acids in length that contains seven conserved cysteine residues.

Generally speaking, the individual members of the BMP family are highly conserved proteins having at least 50% sequence identity, preferably at least 70% sequence identity, and more preferably at least 80% sequence identity to each other. In particular, the individual members of the BMP family have a highly conserved carboxy terminal mature protein domain having at least 50% sequence identity, preferably at least 70% sequence identity, and more preferably at least 80% sequence identity, between the different family members.

The terms "bone morphogenetic protein" and "BMP" also encompass allelic variants of BMPs, function conservative variants of BMPs, and mutant BMPs that retain BMP activity. The BMP activity of such variants and mutants can be confirmed by any of the methods well known in the art (see the section Assays to characterize BMP, below) or as described in Example 1.

The nucleotide and amino acid sequences for BMP orthologs from a variety of species (including human, mouse, rat, cow, rabbit, dog, chicken, turtle, tilapia, zebrafish and *Xenopus*) are known in the art. For example, nucleotide and amino acid sequences for a human BMP-2 (see, for example, Wozney et al. *Science* 1988; 242:1528-1534), BMP-3 (see, e.g., Wozney et al. *Science* 1988; 242:1528-1534), BMP-3b (see, e.g., Hino et al. *Biochem. Biophys. Res. Commun.* 1996; 223:304-310), BMP-4 (see, e.g., Oida et al. *DNA Seq.* 1995; 5:273-275), BMP-5 (see, e.g., Celeste et al. *Proc Natl Acad Sci USA* 1990; 87:9843-9847), BMP-6 (see, e.g., Celeste et al. *Proc Natl Acad Sci USA* 1990; 87:9843-9847), BMP-7 (see, e.g., Celeste et al. *Proc Natl Acad Sci USA* 1990; 87:9843-9847), BMP-8 (see, e.g., Ozkaynak *J. Biol. Chem.* 1992; 267:25220-25227), BMP-9 (see, e.g., Strausberg et al. *Proc Natl Acad Sci USA* 2002; 99:16899-16903), BMP-10 (see, e.g., Neuhaus et al. *Mech. Dev.* 1999; 80:181-184); BMP-11 (see, e.g., Gonzalez-Cadavid et al. *Proc Natl Acad Sci USA* 1998; 95:14938-14943); BMP-12 (see, e.g., U.S. Pat. No. 5,658,882), BMP-13 (see, e.g., U.S. Pat. No. 5,658,882), BMP-14 (see, e.g., Chang et al. *J. Biol. Chem.* 1994; 269:28227-28234), and BMP-15 (see, e.g., Dube et al *Mol. Endocrinol.* 1998; 12:1809-1817) have been reported.

In preferred embodiments, the BMP is BMP-2, BMP-4, BMP-6, BMP-7, or BMP-9. In particularly preferred embodiments the BMP is BMP-2, BMP-4 or BMP-7.

In preferred embodiments the BMP is a mammalian BMP (e.g., mammalian BMP-2 or mammalian BMP-7). In particularly preferred embodiments, the BMP is a human BMP (hBMP) (e.g. hBMP-2 or hBMP-7).

Amino acid and nucleotide sequences for BMP-2 have been reported for a variety of species, including human, mouse, rat, rabbit, dog, chicken, turtle, zebrafish and *Xenopus*. In preferred embodiments, BMP-2 is a mammalian BMP-2. In particularly preferred embodiments, BMP-2 is a human BMP-2 (hBMP-2). Exemplary nucleotide and amino acid sequences for human BMP-2 are set forth in SEQ ID NOs: 1 and 2, respectively (see FIG. 1 and FIG. 2).

Amino acid and nucleotide sequences for BMP-7 (also known as or OP-1) have been reported for a variety of species, including human, mouse, rat, pig, chicken, *Xenopus*, and zebrafish. In preferred embodiments, BMP-7 is a mammalian BMP-7. In particularly preferred embodiments, BMP-7 is a human BMP-7 (hBMP-7). Exemplary nucleotide and amino acid sequences for human BMP-7 are set forth in SEQ ID NOs: 3 and 4, respectively (see FIG. 3 and FIG. 4).

Amino acid and nucleotide sequences for BMP-4 have been reported for a variety of species, including human, cow, sheep, dog, rat, rabbit, mouse, chicken, *Xenopus*, and zebrafish. In preferred embodiments, BMP-4 is a mammalian BMP-4. In particularly preferred embodiments, BMP-4 is a human BMP-4 (hBMP-4). Exemplary nucleotide and amino acid sequences for human BMP-4 are set forth in SEQ ID NOs: 5 and 6, respectively (see FIG. 5 and FIG. 6).

By "recombinant bone morphogenetic protein" or "recombinant BMP" is meant a BMP produced by a transiently transfected, stably transfected, or transgenic host cell or animal as directed by one of the expression constructs of the invention. The term "recombinant BMP" encompasses BMP proteins in monomeric, homodimeric, and heterodimeric forms. In preferred embodiments, the recombinant BMP is a homodimer or a heterodimer. In preferred embodiments, the recombinant BMP has a glycosylation profile that is substantially similar to that of the corresponding native BMP. The term "recombinant BMP" also encompasses pharmaceutically acceptable salts of such a polypeptide. In other preferred embodiments, the recombinant BMP is based on a human BMP and may be referred to herein as a "rhBMP".

By "prodomain" or "prodomain sequence" or "'pro' sequence" is meant the protein sequence comprising the regulatory N-terminal sequence of the TGF-β family members, including all BMPs.

By "proBMP" is meant a BMP that is covalently and operably linked to its prodomain.

By "recombinant proBMP" is meant a proBMP that is produced by a transiently transfected, stably transfected, or transgenic host cell or animal as directed by one of the expression constructs of the invention.

By "protease-mutant BMP" is meant a proBMP protein with an altered pro-domain amino acid sequence such that the native PC protease cleavage site (R-Xn-R↓) (where X is any amino acid except cysteine and n is 0, 2, 4 or 6) is mutated in order to prevent protease cleavage of the resulting protein by furin, or furin-like proteases, and facilitate protease cleavage by a different protease enzyme, including those described in Table 1.

The nucleic acid sequences encoding representative protease-mutant BMPs and their corresponding amino acid sequences are shown in FIGS. 7-12.

By "recombinant protease-mutant BMP" is meant a protease-mutant BMP produced by a transiently transfected, stably transfected, or transgenic host cell or animal as directed by one of the expression constructs of the invention. The term "recombinant protease-mutant BMP" encompasses protease-mutant BMP proteins in monomeric, homodimeric, and heterodimeric forms. In preferred embodiments, the recombinant protease-mutant BMP has a glycosylation profile that is substantially similar to that of the corresponding native BMP.

By "genetically-engineered nucleic acid sequence" is meant a nucleic acid sequence wherein the component sequence elements of the nucleic acid sequence are organized within the nucleic acid sequence in a manner not found in nature. Such a genetically-engineered nucleic acid sequence can be found, for example, ex vivo as isolated DNA, in vivo as extra-chromosomal DNA, or in vivo as part of the genomic DNA.

By "expression construct" or "construct" is meant a nucleic acid sequence comprising a target nucleic acid sequence or sequences whose expression is desired, operably linked to sequence elements which provide for the proper transcription and translation of the target nucleic acid sequence(s) within the chosen host cells. Such sequence elements can include a promoter, a signal sequence for secretion, a polyadenylation signal, intronic sequences, insulator sequences, and other elements described in the invention. The "expression construct" or "construct" can further comprise "vector sequences." By "vector sequences" is meant any of several nucleic acid sequences established in the art which have utility in the recombinant DNA technologies of the invention to facilitate the cloning and propagation of the expression constructs including (but not limited to) plasmids, cosmids, phage vectors, viral vectors, and yeast artificial chromosomes.

By "operably linked" is meant that a target nucleic acid sequence and one or more regulatory sequences (e.g., promoters) are physically linked so as to permit expression of the polypeptide encoded by the target nucleic acid sequence within a host cell.

By "signal sequence" is meant a nucleic acid sequence which, when incorporated into a nucleic acid sequence encoding a polypeptide, directs secretion of the translated polypeptide (e.g., a BMP protein) from cells which express said polypeptide. The signal sequence is preferably located at the 5' end of the nucleic acid sequence encoding the polypeptide, such that the polypeptide sequence encoded by the signal sequence is located at the N-terminus of the translated polypeptide. By "signal peptide" is meant the peptide sequence resulting from translation of a signal sequence.

As used herein, the term "polypeptide" or "protein" refers to a polymer of amino acid monomers that are alpha amino acids joined together through amide bonds. Polypeptides are therefore at least two amino acid residues in length, and are usually longer. Generally, the term "peptide" refers to a polypeptide that is only a few amino acid residues in length. A polypeptide, in contrast with a peptide, can comprise any number of amino acid residues. Hence, the term polypeptide includes peptides as well as longer sequences of amino acids.

By "host cell" is meant a cell which has been transfected with one or more expression constructs of the invention. Such host cells include mammalian cells in in vitro culture and cells found in vivo in an animal. Preferred in vitro cultured mammalian host cells include primary the mammalian cells are CHO, COS, HEK, NS0, BHK, HELA, 3T3, PERC.6 or other cells commonly used by those skilled in the art to produce recombinant proteins.

By "transfection" is meant the process of introducing one or more of the expression constructs of the invention into a host cell by any of the methods well established in the art, including (but not limited to) microinjection, electroporation, liposome-mediated transfection, calcium phosphate-mediated transfection, or virus-mediated transfection. A host cell into which an expression construct of the invention has been introduced by transfection is "transfected".

By "transiently transfected cell" is meant a host cell wherein the introduced expression construct is not permanently integrated into the genome of the host cell or its progeny, and therefore may be eliminated from the host cell or its progeny over time. By "stably transfected cell" is meant a host cell wherein the introduced expression construct has integrated into the genome of the host cell and its progeny.

By "proprotein convertase" is meant an intracellular serine protease which is responsible for cleavage of proproteins. The cleavage recognition motifs for these enzymes involve cleavage at either specific single or pairs of basic residues of the general formula $(R/K)-X_n-(R/K)$, where X is any amino acid except cysteine and n=0, 2, 4 or 6. Generally the term relates to furin (also called paired basic amino-acid-cleaving enzyme (PACE)), PC1/PC3, PC2, PC4, PACE4, PC5/PC5A/PC6, PC5B/PC6B (a spice variant of PC5A) and PC7/PC8/lymphoma proprotein convertase.

In accordance with one aspect of the present invention, there is provided an in vitro method of producing a recombinant protein that comprises the step of expressing a recombinant gene encoding the protein of interest in eukaryotic cells under conditions in which cleavage of the prodomain of the protein is inhibited, altered or eliminated.

Pro-Domain Cleavage Inhibition/Alteration

Generally the method of the present invention includes the step of inhibiting or altering the cleavage of a pro-domain of a recombinant protein of interest in order to increase the amount of recombinant protein secreted from a eukaryotic cell. The inhibition or alteration of the cleavage of the pro-domain can be achieved by various means, for example, as described herein.

1. Creation of Cell Lines with Altered Proprotein Convertase Expression or Activity In accordance with a specific embodiment, the method of the present invention employs eukaryotic cells that have been genetically engineered by mutating one or more genes encoding PCs to reduce, eliminate or facilitate regulation of overall expression of the PC genes or to reduce or eliminate the PC-activity of the enzymes expressed by the genes. For example, mutation of a PC gene can be performed in order to put expression of the gene under the control of a promoter of choice, such as a controlled expression, or inducible promoter (e.g., Tet-on/tet-off).

Alternatively, the PC gene can be mutated (see Takahashi et al., Biochem Biophys Res Commun. 1993; 195:1019-26.) to reduce or eliminate PC activity of the expressed protein.

2. Inhibition of Proprotein Convertase Using a Gene Expression Inhibitor

In accordance with a specific embodiment, the method of the present invention includes the step of inhibiting expression of PC in the cells used to produce the recombinant protein of interest.

Methods to inhibit gene expression in a cell are well known to those of skill in the art. Methods include, but are not limited to, antisense, gene "knock-out," ribozyme, interfering RNA (RNAi) and/or triple helix methods. In a particular example, proprotein convertase activity has been inhibited by to co-transfection of a gene expressing a PC inhibitor such as α1-PDX (see for example Dubois et al. *Am. J. Path.* 2001; 158:305-316, Cui et al. *EMBO J.* 1998; 7:4735-4743).

In a specific embodiment cells can be transfected with a plasmid expressing the shRNA interfering RNAi for furin, (see for example SureSilencing shRNA Plasmid for Human FURIN, Superarray Bioscience corporation cat #KH09618N) in order to reduce or abolish expression of furin.

3. Inhibition of Proprotein Convertase Using an Enzyme Inhibitor

In accordance with a specific embodiment, the method of the present invention includes the step of inhibiting PC activity using a specific enzyme inhibitor or combination of inhibitors. Methods to inhibit proprotein convertase activity using an inhibitor are well known in the art (for review see Basak *J. Mol. Med.* 2005; 83:844-855). These inhibitors generally fall into 3 classes, proteins, peptides or non-peptides, any of which can be used, alone or in combination, in the method of the present invention.

The PC inhibition step involves the addition of the inhibitor(s) to the culture medium of the cells that are producing the recombinant protein of interest. Selection of the amount of inhibitor(s) to be added to the culture medium would be a matter of routine to a worker of skill in the art. For example, to determine the optimal concentration of the inhibitor(s), the cell lines can be cultured with increasing doses of the inhibitor and the amount of recombinant protein and recombinant proprotein produced optimized by measuring mature and proforms (or PC-resistant) by any of the methods described below.

4. Production of a Proprotein Convertase-Resistant "Proform" of BMP

In accordance with a specific embodiment, the method of the present invention includes the step of engineering the cells to generate proprotein convertase-resistant protein of interest, by altering the PC recognition motif between the pro and mature domains of the protein to partially or completely inhibit the rate of cleavage of the prodomain from the mature protein.

The recognition motif for protein cleavage between the pro and mature domain of proteins by protein convertases are well known (see reviews by Denault and Leduc *FEBS Lett* 1996; 379: 113-116 and Khatib et al. *Am J Pathol* 2002; 160: 1921-1935). The general recognition sequence is R/K-$X_n$-R/K where $X_n$=0, 2, 4, 6). For example IGF-1 has the recognition sequence P-A-K-S-A-R, PDGF-A has the recognition sequence P-I-R-R-K-R and PTH has the recognition sequence K-S-V-K-K-R (see Khatib et al. *Am J Pathol* 2002; 160: 1921-1935).

The recognition motif for proprotein cleavage between the pro and mature domain of BMPs is well known to comprise the sequence R-X-X-R↓, with a higher proteolytic activity when the sequence is R-X-K/R-R. (Constam et al. *J. Cell Biol.* 1999; 144:139-149).

In a specific example of this embodiment, the wild-type PC recognition site is modified or substituted such that the secreted protein includes a new, non-PC, cleavage site. Such cleavage sites and the corresponding enzymes are well known to workers of skill in the art. For example, the expression of recombinant proteins as fusions to proteins that serve as an affinity tag are well known in the art. Removal of the affinity tag requires the presence of a short enzymatically cleavable peptide sequence inserted between the recombinant protein and the affinity tag. Once purification has occurred, the mature recombinant protein is released from the tag by the use of specific enzymes (Waugh et al. *Trends Biotechnol.* 2005; 6:316-320 and Jenny et al. *Protein Expr. Purif.* 2003; 31:1-11) that recognize the cleavage site.

In one embodiment of the present invention the RXnR proprotein convertase cleavage site is mutated to one that is resistant to proprotein convertases, but sensitive to other protease enzymes. A number of specific cleavage enzymes can be used (Table 1). In this manner, the recombinant protein of interest (e.g., BMP) is expressed in its pro-form, which would be processed to the mature form once it was purified from the expression milieu.

TABLE 1

Examples of enzymes used to cleave affinity tags from recombinant proteins.

| Enzyme | Cleavage Site | Comment |
|---|---|---|
| Factor Xa | IEGR↓-X | Generate proteins with native N-termini, |
| Enterokinase | DDDDK↓-X | but are promiscuous so must determine whether degrade protein internally. |
| acTEV | ENLYFQ↓-G | Highly specific engineered enzymes. |
| PreScission | LEVLFQ↓-GP | However they both require presence of a C-terminal residue, which is thus left behind on the protein. TEV is somewhat amenable to the G being replaced by other amino acids. |

In the example of BMP production, the selection of an optimal proteolytic enzyme and cleavage conditions can be assessed through expression of the mutated rhBMP protein in vitro followed by the evaluation of various standard conditions for different enzymes. The choice of enzyme and conditions are guided by results that a) produce biologically active rhBMP via cleavage of the linker, and b) do not degrade the rhBMP via cleavage of internal sites within the rhBMP.

Assembly of Expression Constructs

The recombinant DNA methods employed in practicing the present invention are standard procedures, well-known to those skilled in the art (as described, for example, Glover and Hames, eds. DNA Cloning: A Practical Approach Vol I. Oxford University Press, 1995; Glover and Hames, eds. DNA Cloning: A Practical Approach Vol II. Oxford University Press, 1995; Glover and Hames, eds. DNA Cloning: A Practical Approach Vol III. Oxford University Press, 1996; Glover and Hames, eds. DNA Cloning: A Practical Approach, Vol IV. Oxford University Press, 1996; Gait, ed. Oligonucleotide Synthesis. 1984; Hames and Higgens, eds. Nucleic Acid Hybridization. 1985; Hames and Higgens, eds. Transcription and Translation. 1984; Perbal, A Practical Guide to Molecular Cloning. 1984; Ausubel et al., eds. Current Protocols in Molecular Biology. John Wiley & Sons, Inc. 1994; Sambrook et al. Molecular Cloning: A Laboratory Manual, Third Edition. Cold Spring Harbor Laboratory Press. 2001; Dieffenbach and Dveksler, eds. PCR Primer: A Laboratory Manual, Second Edition. Cold Spring Harbor Laboratory Press. 2003; and Ashley, ed. PCR 2: A Practical Approach. Oxford University Press. 1996). These standard molecular biology techniques can be used to prepare the expression constructs of the invention.

The expression constructs of the invention comprise elements necessary for proper transcription and translation of a target protein-encoding nucleic acid sequence (e.g., a target BMP-encoding nucleic acid sequence) within the chosen host cells, including a promoter, a signal sequence to direct secretion of the translated product, and a polyadenylation signal. Such expression constructs can also contain intronic sequences or untranslated cDNA sequences intended to improve transcription efficiency, translation efficiency, and/or mRNA stability. The BMP-encoding nucleic acid sequence intended for expression can possess its endogenous 3' untranslated sequence and/or polyadenylation signal or contain an exogenous 3' untranslated sequence and/or polyadenylation signal. Codon selection, where the target nucleic acid sequence of the construct is engineered or chosen so as to contain codons preferentially used within the desired host cell, can be used to minimize premature translation termination and thereby maximize expression.

The expression constructs of the invention which provide expression of a BMP protein in the desired host cells can include one or more of the following basic components.

A) Promoter

These sequences can be endogenous or heterologous to the host cell to be modified, and can provide ubiquitous (i.e., expression occurs in the absence of an apparent external stimulus and is not cell-type specific) or tissue-specific (also known as cell-type specific) expression. Promoter sequences for ubiquitous expression can include synthetic and natural viral sequences [e.g., human cytomegalovirus immediate early promoter (CMV); simian virus 40 early promoter (SV40); Rous sarcoma virus (RSV); or adenovirus major late promoter] which confer a strong level of transcription of the nucleic acid molecule to which they are operably linked. The promoter can also be modified by the deletion and/or addition of sequences, such as enhancers (e.g., a CMV, SV40, or RSV enhancer), or tandem repeats of such sequences. The addition of strong enhancer elements can increase transcription by 10-100 fold.

B) Recombinant Protein-Encoding Nucleic Acid Sequence

The selection of the appropriate recombinant protein-encoding polynucleotide will depend on a number of factors, including, but not limited to, the ultimate application of the active protein, the cell line used in production, availability, ease of mutation and/or expression, etc. It is, however, necessary that the protein encoded by the recombinant polynucleotide be one which includes a pro-domain, the cleavage of which results in the production of the active protein.

In specific embodiments suitable recombinant protein-encoding sequences include any nucleic acid sequences that encode TGF-β protein, such as a BMP, including nucleic acid sequences encoding BMP-2, BMP-3, BMP-3b, BMP-4, BMP-5, BMP-6, BMP-7, BMP-8, BMP-9, BMP-10, BMP-11, BMP-12, BMP-13, BMP-14, and BMP-15, as well as nucleic acid sequences encoding allelic variants of BMPs, function conservative variants of BMPs, and mutant BMPs that retain BMP activity.

Nucleic acid sequences that encode BMP orthologs from a variety of species (including human, mouse, rat, cow, rabbit, dog, chicken, turtle, tilapia, zebrafish and *Xenopus*) are known in the art. For example nucleic acid sequences that encode a human BMP-2 (see, e.g., Wozney et al. *Science* 1988; 242:1528-1534), BMP-3 (see, e.g., Wozney et al. *Science* 1988; 242:1528-1534), BMP-3b (see, e.g., Hino et al. *Biochem. Biophys. Res. Commun.* 1996; 223:304-310), BMP-4 (see, e.g., Oida et al. *DNA Seq.* 1995; 5:273-275), BMP-5 (see, e.g., Celeste et al. *Proc Natl Acad Sci USA* 1990; 87:9843-9847), BMP-6 (see, e.g., Celeste et al. *Proc Natl Acad Sci USA* 1990; 87:9843-9847), BMP-7 (see, e.g., Celeste et al. *Proc Natl Acad Sci USA* 1990; 87:9843-9847), BMP-8 (see, e.g., Ozkaynak *J. Biol. Chem.* 1992; 267:25220-25227), BMP-9 (see, e.g., Strausberg et al. *Proc Natl Acad Sci USA* 2002; 99:16899-16903), BMP-10 (see, e.g., Neuhaus et al. *Mech. Dev.* 1999; 80:181-184); BMP-11 (see, e.g., Gonzalez-Cadavid et al. *Proc Natl Acad Sci USA* 1998; 95:14938-14943); BMP-12 (see, e.g., U.S. Pat. No. 5,658,882), BMP-13 (see, e.g., U.S. Pat. No. 5,658,882), BMP-14 (see, e.g., Chang et al. *J. Biol. Chem.* 1994; 269:28227-28234), or BMP-15 (see, e.g., Dube et al *Mol. Endocrinol.* 1998; 12:1809-1817) have been reported.

In preferred embodiments, the nucleic acid sequence encodes BMP-2, BMP-4, BMP-6, BMP-7, or BMP-9. In particularly preferred embodiments the nucleic acid sequence encodes BMP-2, BMP-4 or BMP-7.

In preferred embodiments the nucleic acid sequence encodes a mammalian BMP (e.g., mammalian BMP-2 or mammalian BMP-7). In particularly preferred embodiments, the nucleic acid sequence encodes a human BMP (hBMP) (e.g. hBMP-2 or hBMP-7).

Nucleic acids sequences that encode a BMP-2 have been reported for a variety of species, including human, mouse, rat, rabbit, dog, chicken, turtle, zebrafish and *Xenopus*. In preferred embodiments, the nucleic acid sequence encodes a mammalian BMP-2. In particularly preferred embodiments, the nucleic acid sequence encodes a human BMP-2 (hBMP-2). An exemplary nucleic acid sequence that encodes a human BMP-2 is set forth in SEQ ID NO: 1. Nucleic acid sequences encoding a human BMP-2 are publicly available, for example, from the ATCC (ATCC Number 40345). Nucleic acid sequences encoding a bovine BMP-2 are publicly available, for example, from the ATCC (ATCC Number 40310).

Nucleic acids sequences that encode a BMP-7 have been reported for a variety of species, including human, mouse, rat, pig, chicken, *Xenopus*, and zebrafish. In preferred embodiments, the nucleic acid sequence encodes a mammalian BMP-7. In particularly preferred embodiments, the nucleic acid sequence encodes a human BMP-7 (hBMP-7). An exemplary nucleic acid sequence that encodes a human BMP-7 is set forth in SEQ ID NO: 3. Nucleic acid sequences encoding a human BMP-7 are publicly available, for example, from the ATCC (ATCC Number 68182 and ATCC Number 68020).

Nucleic acid sequences that encode a BMP-4 have been reported for a variety of species, including human, cow, sheep, dog, rat, rabbit, mouse, chicken, *Xenopus*, and zebrafish. In preferred embodiments, the nucleic acid sequence encodes a mammalian BMP-4. In particularly preferred embodiments, the nucleic acid sequence encodes a human BMP-4 (hBMP-4). An exemplary nucleic acid sequence that encodes human BMP-4 is set forth in SEQ ID NO: 5. Nucleic acid sequences encoding a human BMP-4 are publicly available, for example, from the ATCC (ATCC Number MGC-21303 and ATCC Number 40342).

Nucleic acid sequences encoding a human BMP-3 are publicly available from the ATCC (ATCC Number 558527). For example, nucleic acid sequences encoding a human BMP-6 are publicly available from the ATCC (ATCC Number 68245 and ATCC Number 68021). For example, nucleic acid sequences encoding a human BMP-8 are publicly available from the ATCC (ATCC Number 3384435).

In certain embodiments, the BMP-encoding nucleic acid sequence contains sequences that code for the signal peptide, the pro-domain, and the mature polypeptide domain of the BMP. In preferred embodiments, the BMP-encoding nucleic acid sequence contains sequences that code for the pro-domain and the mature polypeptide domain of the BMP.

In certain embodiments the BMP-encoding sequence can comprise the prodomain from one BMP and the mature domain from another. For example combining the pro-domain of hBMP-2 with the mature domain of hBMP-4 (Hammonds et al. *Mol Endocrinol* 1991; 5: 149-155).

The BMP-encoding nucleic acid sequence can also encode an epitope tag for easy identification and purification of the encoded polypeptide. Preferred epitope tags include myc, His, and FLAG epitope tags. The encoded epitope tag can include recognition sites for site-specific proteolysis or chemical agent cleavage to facilitate removal of the epitope tag following protein purification. For example a thrombin cleavage site could be incorporated between a recombinant BMP and its epitope tag. Epitope tags can be fused to the N-terminal end or the C-terminal end of a recombinant BMP.

C) Intron Inclusion

Nucleic acid sequences containing intronic sequences (e.g., genomic sequences) can be expressed at higher levels than intron-less sequences. Hence, inclusion of intronic sequences between the transcription initiation site and the translational start codon, 3' to the translational stop codon, or inside the coding region of the BMP-encoding nucleic acid sequence can result in a higher level of expression.

Such intronic sequences include a 5' splice site (donor site) and a 3' splice site (acceptor site), separated by at least 100 base pairs of non-coding sequence. These intronic sequences can be derived from the genomic sequence of the gene whose promoter is being used to drive BMP expression, from a BMP gene, or another suitable gene. Such intronic sequences should be chosen so as to minimize the presence of repetitive sequences within the expression construct, as such repetitive sequences may encourage recombination and thereby promote instability of the construct. Preferably, these introns can be positioned within the BMP-encoding nucleic acid sequence so as to approximate the intron/exon structure of an endogenous human BMP gene.

D) Signal Sequences

Each expression construct will optionally comprise a signal sequence to provide secretion of the translated recombinant protein from the host cells of interest. Such signal sequences are naturally present in genes whose protein products are normally secreted. The signal sequences to be employed in the invention may be derived from a BMP-encoding nucleic acid sequence (e.g., a BMP gene), from a gene specifically expressed in the host cell of interest, or from another gene whose protein product is known to be secreted (e.g., from human alkaline phosphatase, mellitin, the immunoglobulin light chain protein IgK, or CD33); or may be synthetically derived.

E) Termination Region

Each expression construct will comprise a nucleic acid sequence which contains a transcription termination and polyadenylation sequence. Such sequences will be linked to the 3' end of the protein-encoding nucleic acid sequence. For example, these sequences can be derived from a BMP-encoding nucleic acid sequence (e.g., a BMP gene); can comprise the 3' end and polyadenylation signal from the gene whose 5'-promoter region is driving BMP expression (e.g., the 3' end of the goat β-casein gene); or can be derived from genes in which the sequences have been shown to regulate post-transcriptional mRNA stability (e.g., those derived from the bovine growth hormone gene, the β-globin genes, or the SV40 early region).

F) Other Features of the Expression Constructs

The protein-encoding nucleic acid sequences of interest can be modified in their 5' or 3' untranslated regions (UTRs) and/or in regions coding for the N-terminus of the BMP enzyme so as to preferentially improve expression. Sequences within the BMP-encoding nucleic acid sequence can be deleted or mutated so as to increase secretion and/or avoid retention of the recombinant BMP within the cell, as regulated, for example, by the presence of endoplasmic reticulum retention signals or other sorting inhibitory signals.

In addition, the expression constructs can contain appropriate sequences located 5' and/or 3' of the BMP-encoding nucleic acid sequences that will provide enhanced integration rates in transduced host cells (e.g., ITR sequences as per Lebkowski et al. Mol. Cell. Biol. 1988; 8:3988-3996). Furthermore, the expression construct can contain nucleic acid sequences that possess chromatin opening or insulator activity and thereby confer reproducible activation of tissue-specific expression of a linked transgene. Such sequences include Matrix Attachment Regions (MARs) (McKnight et al. Mol Reprod Dev 1996; 44:179-184 and McKnight et al. Proc Natl Acad Sci USA 1992; 89:6943-6947). See also Ellis et al., PCT publication No. WO95/33841 and Chung and Felsenfield, PCT Publication No. WO96/04390.

The expression constructs further comprise vector sequences which facilitate the cloning and propagation of the expression constructs. Standard vectors useful in the current invention are well known in the art and include (but are not limited to) plasmids, cosmids, phage vectors, viral vectors, and yeast artificial chromosomes. The vector sequences can contain a replication origin for propagation in E. coli; the SV40 origin of replication; an ampicillin, neomycin, or puromycin resistance gene for selection in host cells; and/or genes (e.g., dihydrofolate reductase gene) that amplify the dominant selectable marker plus the gene of interest.

In another variation of this method, the restriction digested expression construct fragment used to transfect a host cell will include a BMP-encoding sequence, 5' and 3' regulatory sequences, and any flanking insulators or MARs, linked to a nucleic acid sequence encoding a protein capable of conferring resistance to a antibiotic useful for selection of transfected eukaryotic cells (e.g., neomycin or puromycin).

Generation of Transfected Cell Lines In Vitro

The expression constructs of the invention can be transfected into host cells in vitro using standard techniques well known to those of skill in the art. Preferred in vitro host cells are mammalian cell lines including CHO, COS, HEK-293, BHK, NS0, HeLa 3T3 and PERC.6 cell lines and their derivatives.

Protocols for in vitro culture of mammalian cells are well established in the art (see for example, Masters, ed. Animal Cell Culture: A Practical Approach 3rd Edition. Oxford University Press, 2000 and Davis, ed. Basic Cell Culture, 2nd Edition. Oxford University Press, 2002).

Techniques for transfection are also well established in the art and can include electroporation, microinjection, liposome-mediated transfection, calcium phosphate-mediated transfection, or virus-mediated transfection (see, for example, Feigner, ed. Artificial self-assembling systems for gene delivery. Oxford University Press, 1996; Lebkowski et al. Mol. Cell Biol. 1988; 8:3988-3996; Ausubel et al., eds. Current Protocols in Molecular Biology. John Wiley & Sons, Inc., 1994; and Sambrook et al. Molecular Cloning: A Laboratory Manual, Third Edition. Cold Spring Harbor Laboratory Press, 2001). Where stable transfection of the host cell lines is desired, the introduced DNA preferably comprises linear expression construct DNA, free of vector sequences, as prepared from the expression constructs of the invention. Transfected in vitro cell lines can be screened for integration and copy number of the expression construct. For such screening, the genomic DNA of a cell line is prepared and analyzed by PCR and/or Southern blot.

Transiently and stably transfected cell lines can be used to evaluate the expression constructs of the invention as detailed below, and to isolate recombinant BMP protein.

Conversion of Proproteins and PC-Resistant Proproteins to Mature Proteins

The method of the present invention also includes the optional step of converting the secreted recombinant proprotein into mature protein. Proproteins secreted by the cells can be converted to the mature proteins by treatment with the appropriate proteases. Proproteins which are susceptible to PC can be cleaved by treatment with proprotein convertases, such as furin (see, e.g., Komada et al. FEBS Lett. 1993; 328(1-2):25-9, Dubois et al. J Biol Chem. 1995; 270(18): 10618-24) or by other proteases that cleave at that site (see, e.g., Mondino et al. Mol Cell Biol. 1991 December; 11(12): 6084-92, Hillger et al. J. Biol. Chem. 2005; 280:14974-14980).

PC resistant proproteins can be converted to mature proteins by cleavage using proteases to which the mutated cleavage site is susceptible (see for example Table 1). Methods for protein cleavage using these enzymes are well known in the art (for review see Jenny et al. Protein Expression and Purification 31 (2003) 1-11, Waugh, Trends in Biotechnology 2005; 6:316-320).

Evaluation of Expression Constructs

The functionality of the expression constructs of the invention can be evaluated using transfected in vitro cell culture systems. Genetic stability of the expression constructs, degree of secretion of the recombinant protein(s), and physical and functional attributes of the recombinant protein(s) can be evaluated. Where the expression construct comprises a ubiquitous promoter any of a number of established mammalian cell culture lines can be transfected.

To confirm that cell lines transfected with the BMP-encoding expression constructs of the invention are producing recombinant BMP, the media from transfected cell cultures can be tested directly for the presence of a secreted BMP protein (see the section Assays to characterize BMP, below). The characteristics and activity of the recombinant BMP can be assessed by any of the methods well established in the art (see the section Assays to characterize BMP, below).

The presence of the transgene in the genomic DNA of a cell of interest, as well as transgene copy number, can be confirmed by techniques well known in the art, including hybridization and PCR techniques.

Purification of Secreted Recombinant Protein

In accordance with a specific embodiment of the present invention, the method includes the additional step of purifying the secreted recombinant protein.

Recombinant proteins, such as BMP, can be purified from cell culture media according to any of the techniques well established in the art, including affinity separation, chromatography, and immunoprecipitation. Such techniques are well described in the art (see, for example, Ausubel et al., eds. Current Protocols in Molecular Biology. John Wiley & Sons, Inc. 1994; Coligan et al., eds. Current Protocols in Immunology. John Wiley & Sons, Inc. 1991; Sambrook et al. Molecular Cloning: A Laboratory Manual, Third Edition. Cold Spring Harbor Laboratory Press. 2001; Harlow and Lane. Using Antibodies: A Laboratory Manual. Cold Spring Harbor Laboratory Press. 1999; Gosling, ed. Immunoassays: A Practical Approach. Oxford University Press. 2000; Matejtschuk, ed. Affinity Separations: A Practical Approach. Oxford University Press, 1997; Oliver, ed. HPLC of Macromolecules: A Practical Approach. Oxford University Press, 1998; Millner, ed. High Resolution Chromatography: A Practical Approach. Oxford University Press, 1999; and Roe, ed. Protein Purification Techniques: A Practical Approach. Oxford University Press, 2001).

In particular, protocols for the purification of BMPs have been described (see, e.g., U.S. Pat. Nos 4,761,471; 4,789,732; 4,795,804; 4,877,864; 5,013,649; 5,618,924; 5,631,142; 6,593,109; Wang et al. *Proc Natl Acad Sci USA* 1990; 87:2220-2224; Vallejo et al. *J Biotech* 2002; 94:185-194; Hu et al. *Growth Factors* 2004; 22:29-33; and Vallejo et al. *Biotech Bioeng* 2004; 85:601-609). In particular, protocols for the purification of BMP heterodimers, including BMP-2/-7 heterodimers and BMP-2/-6 heterodimers have been described (see, e.g., U.S. Pat. No. 6,593,109 and Aono et al. *Biochem Biophys Res Comm.* 1995; 210:670-677).

In preferred embodiments, recombinant BMP is purified by heparin affinity chromatography. BMP dimers have greater affinity for heparin than do BMP homodimers, thus by using heparin affinity chromatography for purification of recombinant BMP, the active dimer is selectively purified. Techniques for the purification of BMP by heparin affinity chromatography are well known in the art (see, e.g., U.S. Pat. Nos. 5,013,649; 5,166,058; 5,631,142; Wang et al. *Proc Natl Acad Sci USA* 1990; 87:2220-2224; and Vallejo et al. *J Biotech* 2002; 94:185-194).

Assays to Characterize Recombinant Protein Expressed

Various assays can be used to characterize the recombinant protein expressed by transiently or stably transfected host cells. Suitable assays include, for example, assays to characterize protein levels, protein purity, activity, stability, structural characteristics, and in vitro and in vivo function.

For example, the amount of recombinant protein produced can be quantitated by any of the techniques well known in the art, including denaturing or non-denaturing gel electrophoresis, Western blotting, immunoassay (e.g., enzyme linked immunosorbent assays, ELISA), immunohistochemistry, electrometry, spectrophotometry, chromatography (e.g., high pressure liquid chromatography, HPLC and ion-exchange chromatography) and radiometric methodologies. In addition, various physical characteristics of the recombinant protein can be characterized, including primary amino acid sequence, protein purity, molecular weight, isoelectric point, subunit composition (e.g., monomeric, homodimeric, heterodimeric), glycosylation profile, by any of the techniques well known in the art, including denaturing or non-denaturing gel electrophoresis, Western blotting, immunoassay (e.g., enzyme linked immunosorbent assays, ELISA), immunohistochemistry, electrometry, spectrophotometry, chromatography (e.g., high pressure liquid chromatography, HPLC and ion-exchange chromatography) and radiometric methodologies.

Such methods are well known in the art (see, for example, such methods are well known in the art (See for example, Ausubel et al., eds. Current Protocols in Molecular Biology. John Wiley & Sons, Inc. 1994; Coligan et al., eds. Current Protocols in Immunology. John Wiley & Sons, Inc. 1991; Sambrook et al. Molecular Cloning: A Laboratory Manual, Third Edition. Cold Spring Harbor Laboratory Press. 2001; Harlow and Lane. Using Antibodies: A Laboratory Manual. Cold Spring Harbor Laboratory Press. 1999; Gosling, ed. Immunoassays: A Practical Approach. Oxford University Press. 2000; Matejtschuk, ed. Affinity Separations: A Practical Approach. Oxford University Press, 1997; Oliver, ed. HPLC of Macromolecules: A Practical Approach. Oxford University Press, 1998; Millner, ed. High Resolution Chromatography: A Practical Approach. Oxford University Press, 1999; Roe, ed. Protein Purification Techniques: A Practical Approach. Oxford University Press, 2001; Hockfield et al. Selected Methods for Antibody and Nucleic Acid Probes. Cold Spring Harbor Laboratory Press. 1993; Gore, ed. Spectrophotometry and Spectrofluorimetry: A Practical Approach. Oxford University Press, 2000'; and Higgins and Hames, eds. Post-Translational Processing: A Practical Approach. Oxford University Press, 1999).

In particular, protocols for the characterization of BMP proteins by protein concentration determination, tryptic peptide mapping, amino acid content analysis, amino acid sequence determination, molecular weight determination, isoelectric point determination, N-terminal sequence analysis, and characterization of subunit composition (e.g., monomer versus dimer) have been described (see, for example, U.S. Pat. Nos. 4,761,471; 4,789,732; 4,795,804; 4,877,864; 5,013,649; 5,166,058; 5,618,924; 5,631,142; Wang et al. Proc Natl Acad Sci USA 1990; 87:2220-2224; and Vallejo et al. J Biotech 2002; 94:185-194).

For example, recombinant BMP can be separated on Sephacryl S-300 to distinguish the monomeric, homodimeric, and heterodimeric forms of the protein. For example, the primary amino acid sequence, and in particular the sequence of the amino terminus, of recombinant BMP can be determined by protein sequencing.

For example, protocols for radioimmunoassay analysis of BMP proteins have been described (see, for example, U.S. Pat. No. 4,857,456). For example, protocols for immunoblot analysis of BMP proteins have been described (see, for example, Wang et al. Proc Natl Acad Sci USA 1990; 87:2220-2224). For example, ELISA kits for the quantitation of protein levels of human, rat, or mouse BMP-2 are commercially available, for example, from R&D Systems (catalog #DBP200, PDBP200, or SBP200). For example, ELISA kits for the quantitation of protein levels of human BMP-7 are commercially available, for example, from R&D Systems (catalog #DY354 or DY354E). For example, a panel of monoclonal antibodies can be used to characterize the functional domains of the recombinant BMP. A variety of polyclonal and monoclonal antibodies for the various BMPs are available from a variety of commercial sources, including Chemicon, Alpha Diagnostics International, Novus Biologicals, Abcam, Abgent, and Calbiochem.

Assays to characterize in vitro and in vivo function of recombinant BMPs are well known in the art, (see, e.g., U.S. Pat. Nos. 4,761,471; 4,789,732; 4,795,804; 4,877,864; 5,013,649; 5,166,058; 5,618,924; 5,631,142; 6,150,328; 6,593,109; Clokie and Urist *Plast. Reconstr. Surg.* 2000; 105:628-637; Kirsch et al. *EMBO J.* 2000; 19:3314-3324; Vallejo et al. *J Biotech* 2002; 94:185-194; Peel et al. *J Craniofacial Surg.* 2003; 14:284-291; and Hu et al. *Growth Factors* 2004; 22:29-33.

Such assays include: in vivo assays to quantitate osteoinductive activity of a BMP following implantation (e.g., into hindquarter muscle or thoracic area) into a rodent (e.g., a rat or a mouse) (see, e.g., U.S. Pat. Nos 4,761,471; 4,789,732; 4,795,804; 4,877,864; 5,013,649; 5,166,058; 5,618,924; 5,631,142; 6,150,328; 6,503,109; Kawai and Urist. *Clin Orthop Relat Res* 1988; 222:262-267; Clokie and Urist *Plast. Reconstr. Surg.* 2000; 105:628-637; and Hu et al. *Growth Factors* 2004; 22:29-33); in vivo assays to quantitate activity of a BMP to regenerate skull trephine defects in mammals (e.g., rats, dogs, or monkeys) (see, e.g., U.S. Pat. Nos. 4,761,471 and 4,789,732); in vitro assays to quantitate activity of a BMP to induce proliferation of in vitro cultured cartilage cells (see, e.g., U.S. Pat. No. 4,795,804); in vitro assays to quantitate activity of a BMP to induce alkaline phosphatase activity in in vitro cultured muscle cells [e.g., C2C12 cells (ATCC Number CRL-1772)] or bone marrow stromal cells [e.g., murine W-20 cells (ATCC Number CRL-2623)] (see, e.g., U.S. Pat. No. 6,593,109; Ruppert et al. *Eur J Biochem* 1996; 237:295-302; Kirsch et al. *EMBO J* 2000; 19:3314-3324; Vallejo et al. *J Biotech* 2002; 94:185-194; Peel et al. *J Craniofacial Surg.* 2003; 14:284-291; and Hu et al. *Growth Factors* 2004; 22:29-33); in vitro assays to quantitate activity of a BMP to induce FGF-receptor 2 (FGFR3) expression in in vitro cultured mesenchymal progenitor cell lines (e.g., murine C3H10T1-2 cells) (see, e.g., Vallejo et al. *J Biotech* 2002; 94:185-194); in vitro assays to quantitate activity of a BMP to induce proteoglycan synthesis in chicken limb bud cells (see, e.g., Ruppert et al. *Eur J Biochem* 1996; 237:295-302); and in vitro assays to quantitate activity of a BMP to induce osteocalcin treatment in bone marrow stromal cells [e.g., murine W-20 cells (ATCC Number CRL-2623)] (see, e.g., U.S. Pat. No. 6,593,109).

EXAMPLES

The present invention is next described by means of the following examples. However, the use of these and other examples anywhere in the specification is illustrative only, and in no way limits the scope and meaning of the invention or of any exemplified form. Likewise, the invention is not limited to any particular preferred embodiments described herein. Indeed, many modifications and variations of the invention may be apparent to those skilled in the art upon reading this specification, and can be made without departing from its spirit and scope. The invention is therefore to be limited only by the terms of the appended claims, along with the full scope of equivalents to which the claims are entitled.

In accordance with the present invention there may be employed conventional molecular biology, microbiology, protein expression and purification, antibody, and recombinant DNA techniques within the skill of the art. Such techniques are explained fully in the literature. See, e.g., Glover and Hames, eds. DNA Cloning: A Practical Approach Vol I. Oxford University Press, 1995; Glover and Hames, eds. DNA Cloning: A Practical Approach Vol II. Oxford University Press, 1995; Glover and Hames, eds. DNA Cloning: A Practical Approach Vol III. Oxford University Press, 1996; Glover and Hames, eds. DNA Cloning: A Practical Approach, Vol IV. Oxford University Press, 1996; Gait, ed. Oligonucleotide Synthesis. 1984; Hames and Higgens, eds. Nucleic Acid Hybridization. 1985; Hames and Higgens, eds. Transcription And Translation. 1984; Perbal, A Practical Guide To Molecular Cloning. 1984; Ausubel et al., eds. Current Protocols in Molecular Biology. John Wiley & Sons, Inc. 1994; Sambrook et al. Molecular Cloning: A Laboratory Manual, Third Edition. Cold Spring Harbor Laboratory Press. 2001; Harlow and Lane. Using Antibodies: A Laboratory Manual. Cold Spring Harbor Laboratory Press. 1999; Dieffenbach and Dveksler, eds. PCR Primer: A Laboratory Manual, Second Edition. Cold Spring Harbor Laboratory Press. 2003; Hockfield et al. Selected Methods for Antibody and Nucleic Acid Probes. Cold Spring Harbor Laboratory Press. 1993; Gosling, ed. Immunoassays: A Practical Approach. Oxford University Press. 2000; Wilkinson, ed. In Situ Hybridization: A Practical Approach. Oxford University Press. 1999; Ashley, ed. PCR 2: A Practical Approach. Oxford University Press. 1996; Herrington and O'Leary, eds. PCR 3: PCR In Situ Hybridization: A Practical Approach. Oxford University Press. 1998; and Allan, ed. Protein Localization by Fluorescence Microscopy: A Practical Approach. Oxford University Press. 2000.

Example 1

Creation of a Cell Line Expressing Recombinant Human BMP-2

Recombinant human BMP-2 was expressed in mammalian cells according to standard protocols as described below.

Materials & Methods

Lambda Bacteriophage containing hBMP-2 cDNA (Cat #40345) and *E. coli* C600 (Cat #23724) were purchased from ATCC. Phi 29 DNA polymerase (cat #EP0092), EcoR1 and (Cat #ER0271) related reagents were from Fermentas (Burlington ON). The yeast pyrophosphatase (Cat #P1006) was purchased from Sigma (Oakville, ON). pBluescript® vector (Cat #212240) was purchased from Stratagene (La Jolla Calif.). The Flp-In™ Vectors (Cat #V6010-20), Flp-In™ CHO cell line (Cat #R758-07), pUC16 (cat# Cat. No. 15363-013) and Lipofectamine Transfection™ reagents (Cat #18324-020) were purchased from Invitrogen (Burlington, ON, CANADA). The Quantikine hBMP-2 ELISA (Cat #DBP 200) was purchased from RnD Systems Inc, (Minneapolis Minn.).

Generation of CHO Cells Expressing hBMP-2

First, the lambda bacteriophage containing the full length cDNA for hBMP-2 was amplified in *E. coli* and isolated as follows:

*E. coli* were grown in liquid LB medium overnight at 37° C. with shaking. Bacteriophage was mixed with the *E. coli* and incubated at room temperature for 20 minutes. The *E. coli-phage* mixture was then warmed to 37° C. and incubated for 10 minutes.

Melted LB top agar was put into sterile tubes and equilibrated at 48° C. The *E. coli-phage* preparation was added to the agar in the tubes and mixed together. This was then poured onto a pre-warmed agar plate and gently rocked to cover the entire plate. The agar is allowed to gel and then is incubated overnight at 37° C.

The following day suspension medium (SM; 50 mM Tris-HCL, pH 7.5, 100 mM Sodium Chloride, 8 mM Magnesium Sulfate, 0.01% gelatin) was added to each plate and incubated for 3 hours at room temperature with shaking. The SM was removed and the plates rinsed once more with SM and the rinse was pooled with the first SM wash. Chloroform (1:50 v:v) was added to the tube and the tube was vortexed vigorously for 15 seconds and then held at room temperature for 15 minutes. The tubes were then centrifuged at 12,000 g and the clear supernatant collected, a few drops of chloroform added, the supernatant vortexed then and stored at 4° C.

DNA Isolation

To 20 mls of supernatant was added 20 μl DNAase (1 μg/μl) and 10 μl of RNAase (10 μg/μl). This was incubated at 37° C. for 1 hour with mixing. The sample was then centrifuged at 48,000 g for 2 hrs 15 minutes at 4° C. The supernatant was discarded and the phage DNA appeared as an opaque small pellet. The pellet was resuspended in 200 μl of 50 mM Tris pH 8.0 and transferred to a microfuge tube. Buffered phenol (200 μl; 100 mM Tris pH 8.0) is added to the resuspended pellet and the mixture was vortexed for 15 minutes. The microfuge tube was then centrifuged and the aqueous (top) layer was transferred a new tube. This was repeated 3 times.

Chloroform (200 μl) was added to the aqueous solution and the tubes shaken well, centrifuged and the top, aqueous layer retained. This was repeated twice. 3M sodium acetate (20 μl pH 4.8) is added to the aqueous solution and the DNA is precipitated with 2 volumes 100% ethanol. The microfuge tube was centrifuged 10 minutes and the supernatant discarded. The pellet was then washed with 1.0 ml 70% ethanol and centrifuged for 5 minutes. The supernatant was removed, the pellet was dried under vacuum and then resuspended in 50 μl TE buffer (10 mM Tris-HCl, 0.1 mM EDTA pH 7.4), mixed well and stored at −20° C.

The amount of DNA was quantitated by measuring absorbance at 260 nm.

Amplification of the hBMP-2 Phage DNA Using Phi 29 Multiple Displacement Amplification The bacterophage DNA was amplified using Phi 29 multiple displacement amplification following the method of Dean et al. *Genome Research* 2001; 11:1095-1099.

Two tubes were prepared as follows:

| Tube 1 | |
|---|---|
| 50-100 ng | Bacteriophage DNA |
| 1.0 μl | 10 × Phi 29 reaction buffer |
| 10 μl | 10 mM Random primer |

Mixed tube 1 thoroughly
Heated to 94° C. for 3 minutes
Cooled on ice for 30 minutes without mixing/vortexing

| Tube 2 | |
|---|---|
| 1.0 μl | 10 × Phi 29 reaction buffer |
| 1.0 μl | 100 mM dNTP (25 mM Each) |
| 1.0 μl | Phi 29 Polymerase (10 Units) |
| 0.5 μl | Yeast Pyrophosphatase (0.5 Units) |
| 5.0 μl | ddH2O |

Tubes 1 and 2 were mixed together with no vortexing and samples were incubated at 30° C. for 18 hours. The reaction was stopped by heating at 65° C. for 10 minutes and DNA was stored at −20° C.

EcoR1 digestion was performed as follows:

Amplified Phage DNA (8 μl) was mixed with 10× EcoR1 Reaction buffer (2 μl), dd H2O (7 μl) and ECoR1 (3.0 μl). The tube was mixed well and incubated at 37° C. for 3 hours. The reaction was stopped by adding 6× Sample buffer. ECoR1 digests were run on 1% Agarose gels. The 1.5 kb fragments containing the BMP-2 gene were cut from the various gels and stored at −20° C. for DNA purification.

Agarose gel pieces (18) were thawed and purified using a Qiagen DNA purification kit. After the agarose was melted at 50° C. the DNA was pooled together by binding the DNA to a single spin column using repeated centrifugation steps prior to washing and elution of the DNA with 40 μl elution buffer.

pUC18 EcoR1 Digestion, and Dephosphorylation

EcoR1 digestion of pUC18 was conducted as follows:

pUC18 plasmid DNA (8 μl) was combined with 10× EcoR1 Reaction buffer (2 μl), dd H2O (8 μl) and EcoR1 (2 μl). The tube was mixed well and incubated at 37° C. for 3 hours. The reaction was stopped by adding 6× Sample buffer. Samples were run on 1.0 Agarose gels. The linearized plasmid was cut from the gel and purified using a Qiagen kit (cat #28704; Qiagen Mississauga ON).

pUC18 plasmid dephosphorylation was done to reduce recirculization of the plasmid without the insert as follows:

pUC18 plasmid DNA (40 μl) 10×ALP reaction buffer (5 μl) and alkaline phosphatase (5 μl) were added together and incubated at 37° C. for 50 minutes. The alkaline phosphatase was then deactivated at 75° C. for 20 minutes. The pUC18 plasmid DNA was purified by extracting twice with and equal volume of phenol:chloroform:isopropanol in the cold followed by centrifugation.

The DNA in the aqueous phase was precipitated by the addition of 2 volumes 100% ethanol as described previously and resulted in a DNA pellet which was resuspended in 50 mM Tris pH 8.0.

Ligation, Transformation and Glycerol Stock Formation

Ligation reactions were done using T4 ligase at 1:1 and 1:5 (vector:insert) ratio as described below. Four tubes were prepared with contents as follows (volumes in μl):

| | Control 1 Vector only | Control 2 Vector + Ligase | Vect:Ins 1:1 | Vect:Ins 1:2 |
|---|---|---|---|---|
| Vector (pUC 18) | 1.0 | 1.0 | 1.0 | 1.0 |
| Insert | 0.0 | 0.0 | 2.5 | 12.0 |
| 10 × T4 ligase reaction Buffer | 2.0 | 2.0 | 2.0 | 2.0 |
| T4 Ligase | 0.0 | 1.0 | 1.0 | 1.0 |
| Water | 17.0 | 16.0 | 13.5 | 4.0 |

The reactions were left for 5 hours at 16 C before being frozen and stored at −20° C.

Transformation was carried out as follows:

The ligation mixtures (4.0 μl) were gently mixed with 40 μl of DH5α *E. coli* cells and left to mix for 30 minutes. Samples were then heat shocked at 42° C. for 90 seconds and placed on ice. LB medium (100 μl) was added to the cells and allowed to recover at 37° C. for 60 minutes.

Glycerol stocks were prepared as follows:

The transformed DH5α cells (150 μl) were plated onto LB ampicillin agarose plates and incubated overnight at 37° C. Single colonies were used to inoculate 10 ml LB ampicillin.

Cultures were grown overnight. The overnight cultures were diluted to $OD_{600}=0.1$ and allowed to grow up to $OD_{600}=0.6$. The transformed cells (800 μl) were mixed with glycerol (200 μl) and stored at −80° C.

Small Scale Plasmid Prep, Hind III Digestion and DNA Sequencing

Small scale plasmid preparation was done as follows:

Single colonies from LB ampicillin agarose plates were used to inoculate 10 ml of LB ampicillin and left to grow overnight at 37° C. Overnight cultures were used to isolate and purify plasmid DNA using the QIAGEN plasmid purification kit (Cat #27104) following the manufacturer's instructions.

Hind III digestion was performed as follows:

DNA (8 μl) isolated as described above was mixed with 10× Hind III Reaction buffer (2 μl), $ddH_2O$ (8 μl) and HindIII enzyme (2 μl). The tube was mixed well and incubated at 37° C. for 3 hours. The reaction was stopped by adding 6× Sample buffer.

DNA Sequencing

Glycerol stock was cultured overnight as described above and the DNA prepared using a Midi-plasmid prep kit (Qiagen Cat #12243) following the manufactures instructions. The DNA was then sent to the Hospital for Sick Children (Toronto, ON) for DNA sequencing.

Transfection of a Mammalian Cell Line with a Vector Containing rhBMP-2 DNA

Once the sequence of rhBMP-2 was confirmed, the cDNA was transfected into a mammalian cell line as follows:

The hBMP-2 cDNA was inserted into the Bluescript® vector (Stratagene) following the manufacturer's instructions. The cDNA for hBMP-2 was inserted into the Flp-In pcDNA5/FRT vector following the manufacturer's protocols. The Flp-In CHO cells were then transfected with the hBMP-2 Flp-In vector using lipofectamine following the manufactures protocols.

Clones containing the hBMP-2 containing vector were selected Zeocin/hygromycin according to the manufacturer's protocols.

Amplification and subcloning of stable transformants: The usage of the Flp-In system in the appropriate Flp-In cell line (Flp-In-CHO cells) eliminates the need to screen multiple recombinant clones, since the integration of the BMP-2 expression plasmid is designed to occur at the same transcriptionally active locus. Three stable cell lines were chosen to confirm consistency of expression levels and amplified using standard techniques.

Screening of Subclones for the Secretion of rhBMP-2

Initial screening of the subclones is done by measuring the amount of hBMP-2 in the conditioned medium using the commercially available Quantikine hBMP-2 ELISA following the manufacturer's instructions (Cat #DBP 200; R&D Systems Inc., Minneapolis Minn.).

Characterization of BMP-2 by Western Blot

Conditioned cell culture medium was centrifuged at 300×g for 5 minutes to pellet away cells and collect the supernatant. Samples were fractionated by polyacrylamide gel electrophoresis using the NuPAGE® SDS-PAGE gel system on the XCell SureLock™ Mini-Cell apparatus (Invitrogen) following the manufacturer's instructions.

Once the samples had been run on the gels they were transferred onto a nitrocellulose membrane using the XCell II™ Blot Module Kit (Invitrogen) following the manufacturer's instructions.

The presence of BMP-2 and proBMP-2 were detected by Western blot as follows. Firstly, the membrane was blocked by incubating it with a solution containing casein, a predominant protein in milk, for 30 min (or overnight) on a rotary shaker. After blocking, the membrane was incubated with anti-BMP-2 (Cell Sciences Cat #PA0025) or anti-proBMP-2 antibodies (RnD SystemsCat #MAB2260) under gentle agitation. After washing off the primary antibody, the membrane was incubated with an appropriate anti-rabbit or anti-mouse secondary antibody conjugated with alkaline phosphatase provided in the Western Breeze® chromogenic immunodetection kit (Invitrogen) and the presence of the secondary antibody was detected following manufacturer's instructions.

Testing of Transfected Clones for In Vitro BMP-2 Activity Assay

Alkaline phosphatase induction in C2C12 cells: The activity of recombinant hBMP-2 protein is quantitated based upon induction of alkaline phosphatase in in vitro cultured C2C12 cells, as has been described (see, e.g., Peel et al. *J Craniofacial Surg.* 2003; 14:284-291 and Hu et al. *Growth Factors* 2004; 22:29033).

C2C12 cells (ATCC accession number CRL-1772, Manassas, Va.) are passaged before confluent and resuspended at $0.5 \times 10^5$ cells/ml in MEM supplemented with 15% heat-inactivated fetal bovine serum, antibiotics and 50 μg/ml ascorbic acid. One ml of cell suspension is seeded per well of a 24 well tissue culture plate (BD Falcon, Fisher Scientific Cat #08-772-1). An aliquot of test BMP-2 sample is added and the cultures maintained at 37° C. and 5% CO2. Test BMP-2 samples included conditioned media, purified recombinant hBMP-2 isolated from conditioned media by heparin affinity chromatography, and as a positive control a commercially available purified recombinant hBMP-2 (R&D Systems, Minneapolis, USA). Control cultures (cultured in media without added BMP-2 sample) are cultured for 2 to 7 days. Medium is changed every two days.

At harvest cultures are rinsed with Tris buffered saline (20 mM Tris, 137 mM NaCl, pH 7.4) and M-Per lysis buffer (Pierce Biotechnology Inc., Rockford, Ill., catalogue #78501) is added. The cell layer is scraped into Eppendorf tubes and sonicated. The lysate is centrifuged at 5000×g at 5° C. for 10 minutes, and the supernatant assayed for alkaline phosphatase (ALP) by monitoring the hydrolysis of nitrophenol phosphate in alkaline buffer (Sigma-Aldrich, St. Louis Mo., catalog P5899) as described in Peel et al. J Craniofacial Surg. 2003; 14:284-291 or by using the Alkaline Phosphatase detection kit, Fluorescence (Sigma-Aldrich, catalogue #APF) according to manufacturer's instructions. To normalize the ALP activity the cellular protein content in each well is also assayed using the Coomasie (Bradford) Protein Assay (Pierce Biotechnology Inc., catalogue #23200). The normalized ALP activity for each sample is calculated by dividing the ALP activity per well by the protein content per well. An activity score is calculated by dividing the ALP activity for each sample by the mean ALP activity of the control and is compared to the score achieved by the positive BMP control.

Results

Screening of the hBMP-2 CHO Stable Transfectants Using a hBMP-2 ELISA

Medium was collected from the various cell lines and assayed for mature hBMP-2. The amount of hBMP-2 in the medium depended on the seeding density, time of incubation and volume of medium, but was normally within the range of 20-100 ng/ml.

Western Blot characterization of the rhBMP-2 produced by the CHO-BMP-2 cells

Incubation of the non-reduced blot with anti-BMP-2 antibodies (Cell Sciences Cat #PA0025) showed two immunoreactive bands in all five samples collected from static cell culture flasks (i.e. T75 flasks) (FIG. 16). The higher molecular weight band co-migrated with the proBMP-2 standard at 97 KDa while the lower immunoreactive band co-migrated with the rhBMP-2 standard at around 30 kDa. When the reduced blot was probed with the same anti-BMP-2 antibody only a single strong immunoreactive band was observed co-migrating with the rhBMP-2 standard at 18 KDa (FIG. 16). We observed background staining at higher molecular weights (possibly BSA, and only in reduced gels), but this was considered to be non-specific. In purified media samples without BSA, this background staining was not observed.

Testing the conditioned medium for BMP biological activity in vitro

Conditioned medium samples were diluted 1:1 with fresh medium and incubated with C2C12 cells for 48 hours. The cells were then assayed for alkaline phosphatase activity as an indicator of the cells undergoing BMP induced osteoinduction. The amount of activity was found to be dose and BMP type dependant and the activity was similar to that expected based on the amount of BMP-2 present based on the ELISA.

Example 2

Effect of Furin Inhibitor 9DR on rhBMP-2 Secretion

Materials & Methods
BMP-2 ELISA Assay
This was performed using the Quantikine hBMP-2 ELISA kit as described in Example 1.
proBMP-2 ELISA Assay The amount of proBMP-2 in the cultures was measured using an ELISA developed by the inventors as follows. Monoclonal anti-human proBMP-2 was purchased from RnD Systems (cat #MAB 2260). Recombinant human proBMP-2 made in E. coli was purchased from Scil Proteins (cat #ALX-20-205). The other reagents for the assay were taken from a Quantikine® hBMP-2 ELISA (cat #DBP 200, RnD Systems). ProBMP-2 standards were made by re-suspending proBMP-2 in the calibrator diluent. High binding 96 well plates (Costar EIA plates, Cat #25952) were coated with 100 µl the proBMP-2 antibody (1 µg/ml PBS) over night at 4° C. The following day the solution was removed and the wells washed 3 times with 400 µl reagent diluent. The wells were then blocked with 300 µl reagent diluent (1% BSA in PBS) for 1 hour at room temperature with shaking. The plates were then used immediately for performance of the assay. The rest of the assay was performed as per manufacturer's instructions for the Quantikine hBMP-2 assay, with standards ranging from 20 ng/ml to 0.625 ng/ml.

In Vitro BMP-2 Activity Assay
This was performed using the C2C12 cell based assay as described in Example 1.
Short Term Experiments Stable CHO cell lines expressing wild type BMP-2 cDNA (CHO-BMP2) generated in Example 1 were seeded into single wells of 6 (2 ml) or 24 (1 ml) well plates at a density of 125,000 cells/ml alpha MEM+15% FBS (Invitrogen). After 24 hours the cells were attached to the dishes and the medium was replaced with fresh medium containing increasing concentrations of the inhibitor 9DR (nona-D-arginine amide; synthesized by Advanced Syntec, Markham ON) from 10 nM to 180 µM, or the nutrient control (D arginine) or medium alone.

The conditioned medium was collected and aliquots were assayed for the presence of hBMP-2 and proBMP-2 by ELISA (as described above). Other aliquots of conditioned media were diluted with fresh medium and added to C2C12 cells to test for in vitro osteoinductive biological activity (as described above).

Long Term Experiments

The long-term effect of 9DR on BMP-2 production was tested in CL350 CELLine flasks (Mandel Scientific Guelph ON). CHO-BMP-2 cells were expanded in T-75 flasks and seeded into the CL350 flasks per the manufacturer's instructions. After 7 days the flasks were randomly assigned to receive culture medium or medium+20 nmol/ml 9DR. This culture medium was added to both the cell and the medium compartments. Conditioned medium was collected every 3 or 4 days from the cell compartment. Reservoir medium in the medium compartment was changed every 7 days. The duration of the experiment was two months.

A crossover experiment was then performed where the treatment for the bioreactors was switched. The control bioreactor was treated with medium containing 9DR while the 9DR-treated bioreactor was treated with fresh medium (no 9DR). Four medium collections were made from each group.

Following the completion of the crossover experiment, the concentration of 9DR was increased 9DR concentration of 60 nmol/ml (instead of 20 nmol/ml 9DR) with the other bioreactor continuing to have control medium. Four medium collections were made from each group. All the media collected were quantified for BMP-2 and proBMP-2 content using ELISA (as described above).

Results

In the 9DR dosage study, CHO cells were cultured with media containing 0 nmol/ml to 80 nmol/ml of 9DR. After a 24 hr incubation, secreted BMP-2 in the media was quantified by BMP-2 ELISA.

Figure 17:
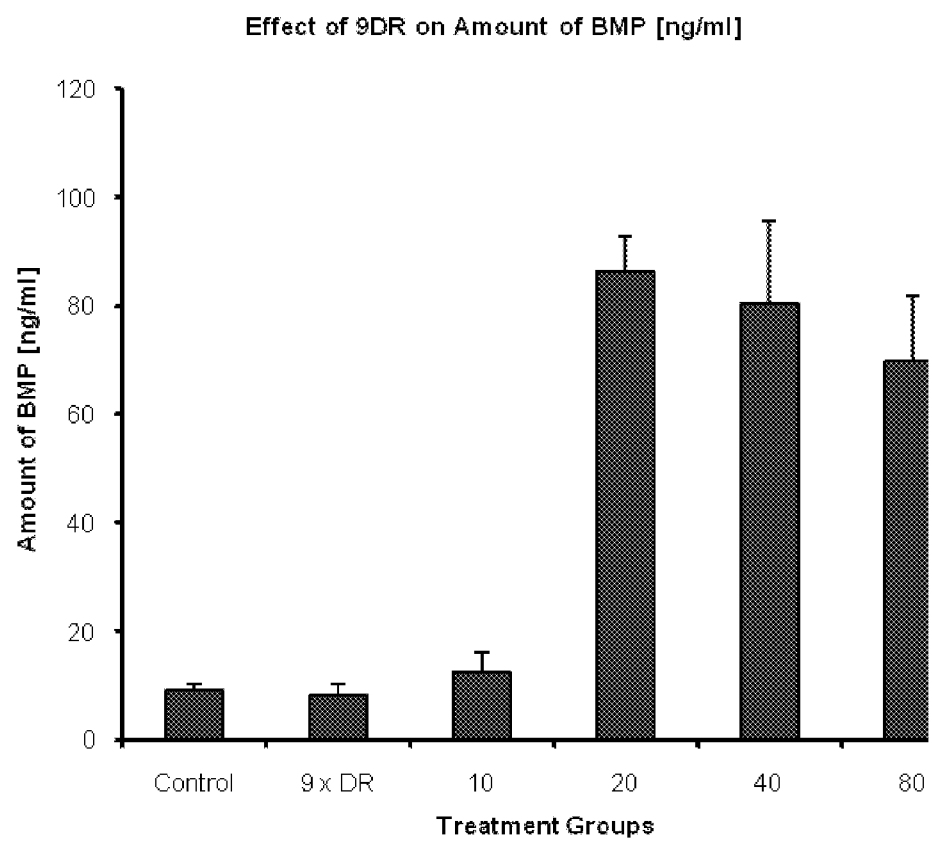
FIG. 17 depicts the results of an ELISA for hBMP-2 in conditioned medium from CHO-BMP-2 cells incubated with the furin inhibitor 9DR at various doses.

BMP-2 ELISA results demonstrated that all the 9DR-treated groups demonstrated equivalent or higher amounts of BMP-2 than the control group (not treated with 9DR). Cells treated with 20 nmol/ml 9DR demonstrated the highest concentration of BMP-2 (FIG. 17). Comparing that to the control group, the 20 nmol/ml 9DR treated group yielded 6-fold more BMP-2—a significant increase in BMP-2 yield tested by ANOVA ($P<0.01$). As 9DR concentration increased over 20 nmol/ml, there was a slight decrease in the overall amount of BMP-2.

Figure 18:
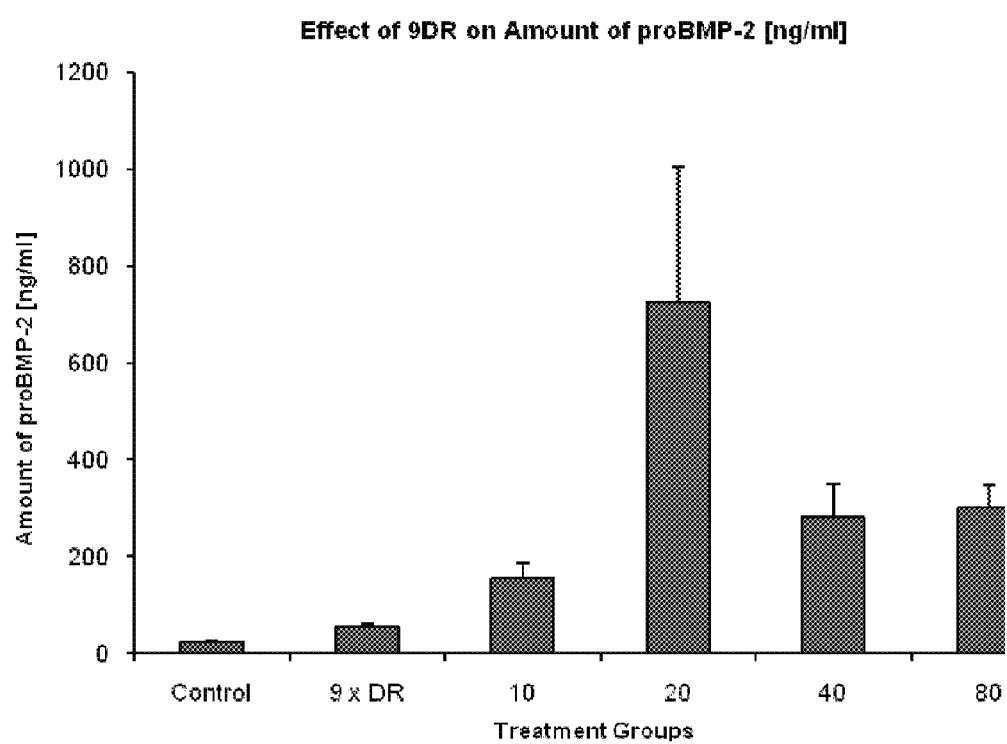
FIG. 18 depicts the results of an ELISA for hpro-BMP-2 in conditioned medium from CHO-BMP-2 cells incubated with the furin inhibitor 9DR at various doses.

Similarly to BMP-2 quantification, the amount proBMP-2 produced was measured by proBMP-2 ELISA. The effect of 9DR inhibition on proBMP-2 secretion was similar to that on BMP-2 (FIG. 18). All the 9DR-treated groups demonstrated higher amounts of proBMP-2 than the control group. The group treated with 20 nmol/ml 9DR had the highest amount of proBMP-2 at 848 ng/ml; a significant increase ($P<0.01$)—approximately 40-fold, compared to the control. As the concentration of 9DR increased further over 20 nmol/ml, proBMP-2 concentration did not further increase but rather slightly decreased.

Biological activity of CHO-produced rhBMP-2 was determined using a C2C12 cell based assay. In this assay, the C2C12 cells increase their alkaline phosphatase activity proportionally to the amount of BMP to which they are exposed. Since this response is specific to the treatment by osteoinductive BMPs, biological activity of BMP-2 can be determined by measuring the cellular ALP activity.

Figure 19:
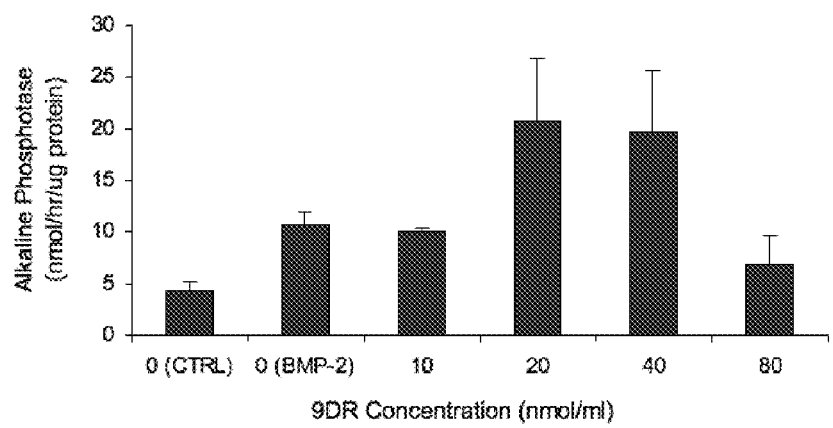
FIG. 19 depicts the results of an in vitro assay for BMP activity in conditioned medium from CHO-BMP-2 cells incubated with the furin inhibitor 9DR at various doses.

Results of the ALP assay showed that all the 9DR treated groups demonstrated equivalent or elevated levels of ALP over the control group (with 0 nmol/ml 9DR). Both the 20 and 40 nmol/ml 9DR-treated groups had the highest ALP activity—a significant increase compared to the control group ($P<0.01$) (FIG. 19).

Long Term Culture

Initial 9DR Concentration: 20 nmol/ml

Figure 20:
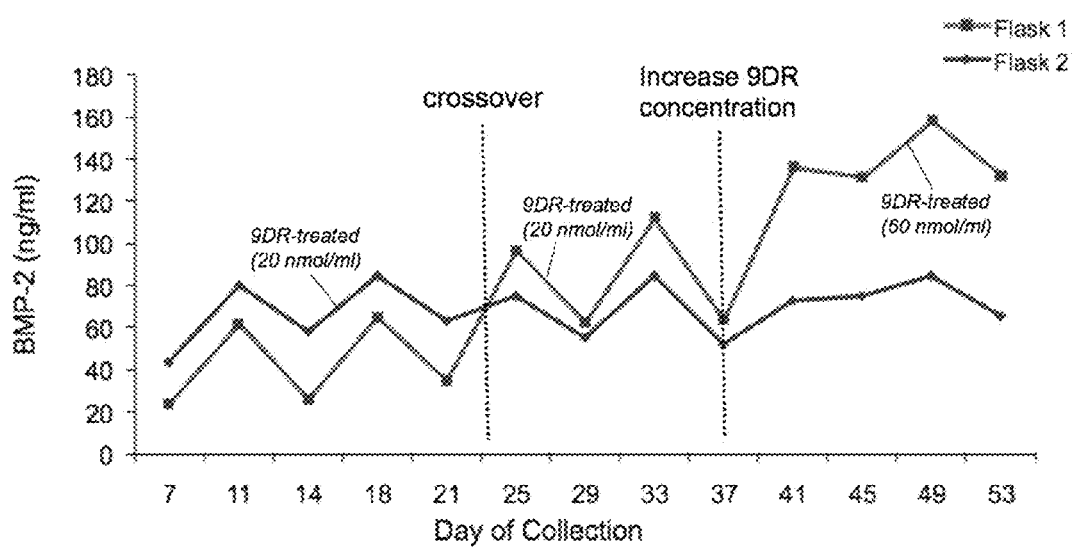
FIG. 20 depicts the results of an ELISA for hBMP-2 in conditioned medium from long-term CHO-BMP-2 cultures in the presence and absence of a furin inhibitor.
Figure 21:
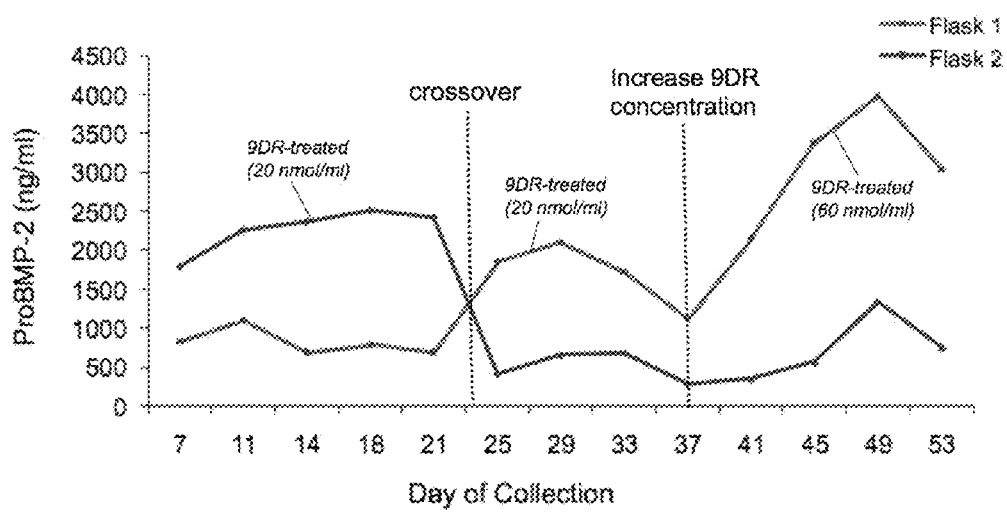
FIG. 21 depicts the results of an ELISA for hpro-BMP-2 in conditioned medium from long-term CHO-BMP-2 cultures in the presence and absence of a furin inhibitor.

Two flasks of cells (with or without 9DR) were cultured for the long-term 9DR study. Initially, 20 nmol/ml of 9DR was added to the medium. ELISA results on the cell culture media harvested CELLine flasks demonstrated that the amount of BMP-2 was higher in the 9DR-treated flask than the control flask (FIG. 20). In addition, 9DR-treated flasks also demonstrated higher proBMP-2 concentration in comparison to the control (FIG. 21). These observed increases were consistent in all media collections.

A crossover experiment was performed in which the treatments were interchanged between the flasks for four media collections. The results from the crossover experiment showed that flask treated with 9DR resulted in elevated concentrations of BMP-2 and proBMP-2 (FIGS. 20 and 21).

Increased 9DR Concentration: 60 nmol/ml

The 9DR concentration was increased to 60 nmol/ml in an attempt to further increase the amounts of BMP-2 and proBMP-2 secreted.

Figure 22:
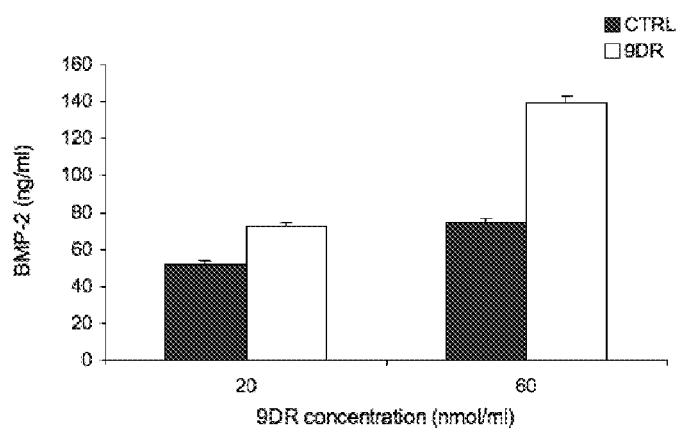
FIG. 22 depicts the results of an ELISA for hBMP-2 in conditioned medium from long-term CHO-BMP-2 cultures in the presence and absence of a furin inhibitor at increasing concentrations.
Figure 23:
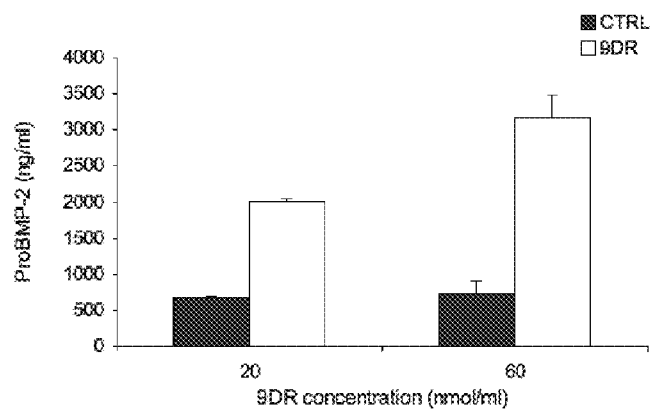
FIG. 23 depicts the results of an ELISA for hpro-BMP-2 in conditioned medium from long-term CHO-BMP-2 cultures in the presence and absence of a furin inhibitor at increasing concentrations.

Four sets of conditioned media were collected from cells treated with 60 nmol/ml 9DR. BMP-2 and ProBMP-2 content from all these collections was measured. ELISA results showed that the BMP-2 and proBMP-2 levels in the conditioned medium were further increased when the 9DR concentration was increased (FIGS. 22 and 23).

Effect of 9DR on Cell Viability

Figure 24:
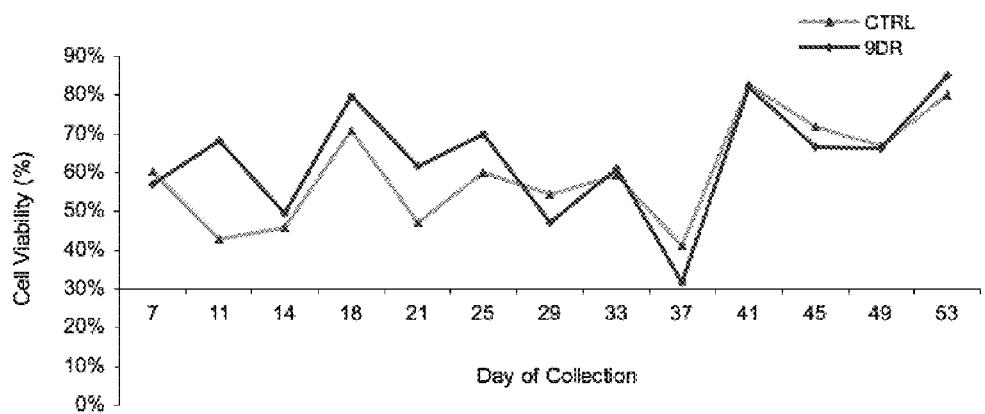
FIG. 24 depicts cell viability results for long-term CHO-BMP-2 cultures in the presence and absence of a furin inhibitor.

Cell viability was assessed at each media collection using a ViCell cell viability analyzer (Beckman) following manufacturer's instructions. Comparison of cell viability indicated that 9DR did not affect cell viability in these long term cultures (FIG. 24).

Effect on Intracellular BMP-2 and ProBMP-2

Figure 25:
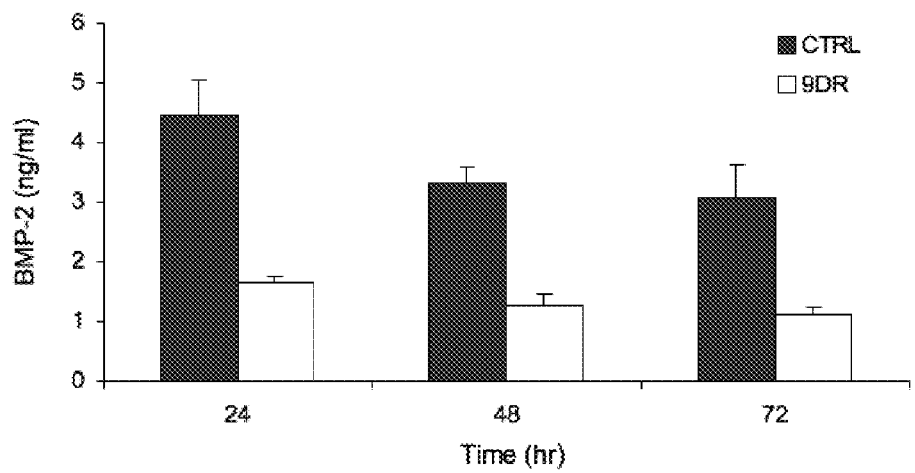
FIG. 25 depicts the results of an ELISA for hBMP-2 from cell lysates of CHO-BMP-2 cells in the presence and absence of a furin inhibitor.
Figure 26:
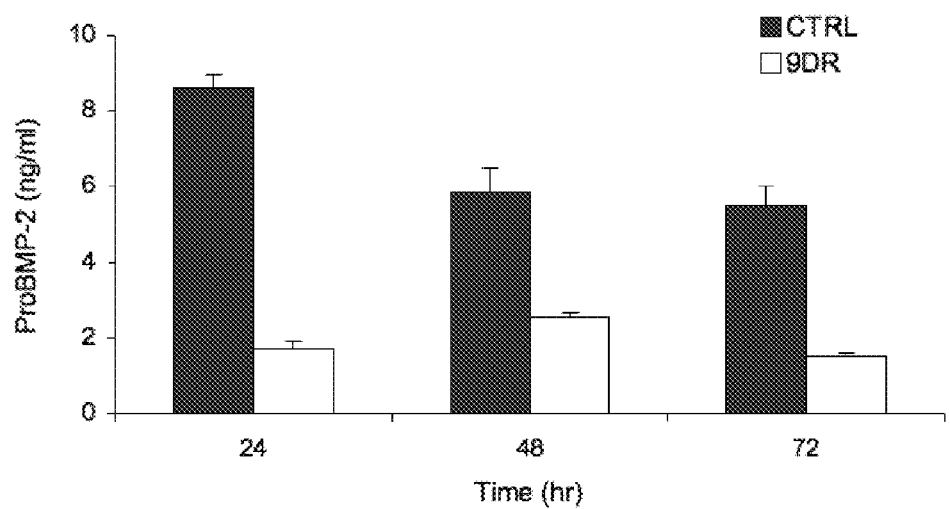
FIG. 26 depicts the results of an ELISA for hpro-BMP-2 from cell lysates of CHO-BMP-2 cells in the presence and absence of a furin inhibitor.

CHO cells growing in 6-well plates were treated with 20 nmol/ml 9DR for 24, 48, and 72 hr. At each time point, conditioned media were collected to measure secreted BMP-2 and proBMP-2. In addition, CHO cells were lysed to measure their intracellular BMP-2 and proBMP-2 contents. ELISA results revealed that 9DR-treated groups had significantly lower amounts of intracellular BMP-2 ($p<0.05$) and proBMP-2 ($p<0.05$) than the control group at all the time points (FIGS. 25 & 26).

Example 3

Improvement of BMP-7 Production Via Furin Inhibition with 9DR

Methods

Generation of CHO Cells Expressing hBMP-7

Cell lines expressing the hBMP-7 transgene were prepared as per the methods described in Example 1.

Treatment of CHO-BMP-7 Cells with 9DR Peptide

Stable CHO cell lines expressing wild type BMP-7 cDNA were seeded into single wells of 24 well plates and cultured in the presence of increasing concentrations of the furin inhibitor 9DR. The conditioned medium was collected and aliquots were assayed for the presence of hBMP-2 by ELISA. The amount of proBMP-7 present in the samples was estimated by western blot. Other aliquots of conditioned media were diluted with fresh medium and added to C2C12 cells to test for in vitro osteoinductive biological activity.

Results

Measurement of Mature hBMP-7 in Conditioned Medium

Figure 27:
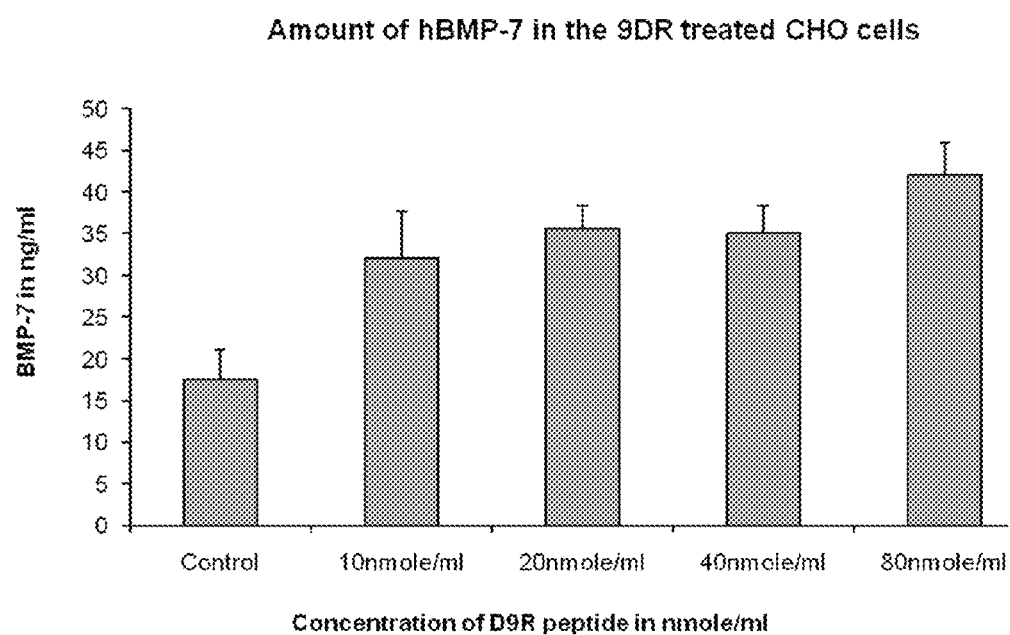
FIG. 27 depicts the results of an ELISA for hBMP-7 in conditioned medium from CHO-hBMP-7 cells incubated with the furin inhibitor 9DR at various doses.

Medium collected 24 hours after exposure of cells to 9DR repeatedly demonstrated an increase in the amount of mature hBMP-7 in the medium, while no difference was seen between the medium only and the DR controls. This increase was routinely between 2 and 10 fold of the medium only control (see FIG. 27).

Example 4

Improvement of BMP-2 Production Via Mutation of the S1 or S1 and S2 Furin Cleavage Site Precursors of BMP are cleaved by proteases that belong to the proprotein convertase family (reviewed above). Their can be multiple cleavage sites in a single BMP molecule. For example, both BMP-2 and BMP-4 have two cleavage consensus sites (named S1 and S2 sites) (Israel et al. *Growth Factors* 1992; 7: 139-150, Cui et al. *Genes Dev* 2001; 15: 2797-2802), while BMP-7 possesses only one consensus site (Gregory et al. *J Biol Chem* 2005; 280: 27970-27980).

Materials & Methods

The plasmid containing human BMP-2 cDNA prepared as described in example 1 was designated as IND2334.

Construction of proBMP-2 Mutated at the S1 Site (S1proBMP-2)

The replacement of the S1 furin cleavage site REKR was accomplished as follows.

First, two pairs of mutagenesis oligo nucleotides were used to separately amplify the 5' half and the 3' half of the rhBMP-2 DNA by PCR. The PCR products were separately cloned into TopoTA vector (Invitrogen). The candidate clones were sequenced, and the correct 5' and the 3' clones were then combined into expression vector pcDNA5 to reconstruct proBMP-2. The resulting plasmid has the REKR sequence (which correspond to amino acid residues 279 to 282 of SEQ ID NO: 2) replaced by sequence TNGIEGRALDP (SEQ ID NO: 16), which encompasses recognition sites of 4 cleavage agents: hydroxylamine, GIuC, factor Xa, and acid. In the PCR step, the very high GC content of the 5' portion of the BMP-2 sequences caused a deletion of 266 base pair GC knot in the 5' segment of the BMP-2 immediately after the signal sequence. This proBMP-2 construct, designated as IND2344, carries a deletion of 88 amino acids in the pro region.

The full-length proBMP-2 with S1 site mutation was constructed by replacing the 3' Bsg1-Xho1 fragment of IND2334 (proBMP-2) with a Bsg1-Xho1 fragment of IND2344, which carries the replacement cleavage sites. Two similar constructs were made sequentially: one in vector pcDNA3 (IND2340), the other in vector pcDNA5 (IND 2341). Both have the same BMP-2 sequences. These plasmids encode an S1proBMP-2 of MW 43 kD (18 kD if processed at the S2 site).

Construction of the proBMP-2 with Mutations at the S1 and S2 Sites (S1S2 ProBMP-2)

The mutation of S2 cleavage site RISR into AISR was achieved by a PCR based method using a pair of primers carrying the desired mutation that amplifies the AflIII-BamH1 fragment of IND2341 (S1proBMP-2). The full length S1S2 ProBMP-2 was constructed by combining the following 3 DNA fragments into the NotI-XhoI sites of IND2341: 1. NotI-AflIII of IND2341; 2. AflIII-BamHI of BMP-2 with the S2 mutation generated by PCR; 3. BamHI-XhoI fragment of IND2341 (S1 proBMP-2). The calculated size of the proBMP-2 encoded by this construct is 43 kD. This plasmid is designated IND2372.

Expression of the rhBMP-2 in Mammalian Cells

The synthesis and secretion of the BMP-2 and mutated furin resistant proBMP constructs were tested in mammalian cells by either transient transfection or by establishing stable cell lines to obtain larger quantities of material. Conditioned media were first characterized for the expression level, the size and integrity of the BMP-2s by western blotting and then for bioactivity using the C2C12 cell based assay as described in Example 1.

To account for possible differences due to different cell types each construct was transfected 4 different cell lines: CHO, COS-7, 293 and a modified 293 cell line that carries the engineered integration site 293FRT (Flip-In 293 cells Invitrogen).

Cleavage of Mutant BMPs by Factor Xa

To demonstrate that the mutant BMPs could be processed in vitro to produce a mature BMP similar to the wild type mature BMP conditioned medium was collected from the cells lines and was digested using the Restriction Protease Factor Xa Cleavage and Removal Kit (Roche Applied Science Cat #1 644 777).

Quantitation of Mutated S1 proBMP by Dot Blot Assay

Ten µl drops of conditioned medium or standards containing known amounts of rhBMP-2 were dotted onto nitrocellulose membranes. Once the drops were dry the membranes were prepared as described for western blots. The amount of BMP-2 in the drops was estimated by comparison of the intensity of stain in the unknown and standard dots.

Results

The wild type BMP-2 construct BC2334 was expressed in all four cell lines by transient transfection and in stable 293FRT cell lines. Expression was confirmed by Northern analysis and by western analysis. To determine the efficiency of the secretion, we analyzed the cell lysate of transiently transfected COS-7 and 293 cells. Little intracellular BMP-2 was found indicating that BMP-2 was efficiently secreted by these cells.

GC knot deleted S1proBMP-2: This mutant BMP-2 (IND2343) was not expressed in any of the cell lines, most likely due to mutation's impact on the processing of the signal peptide.

Figure 28:
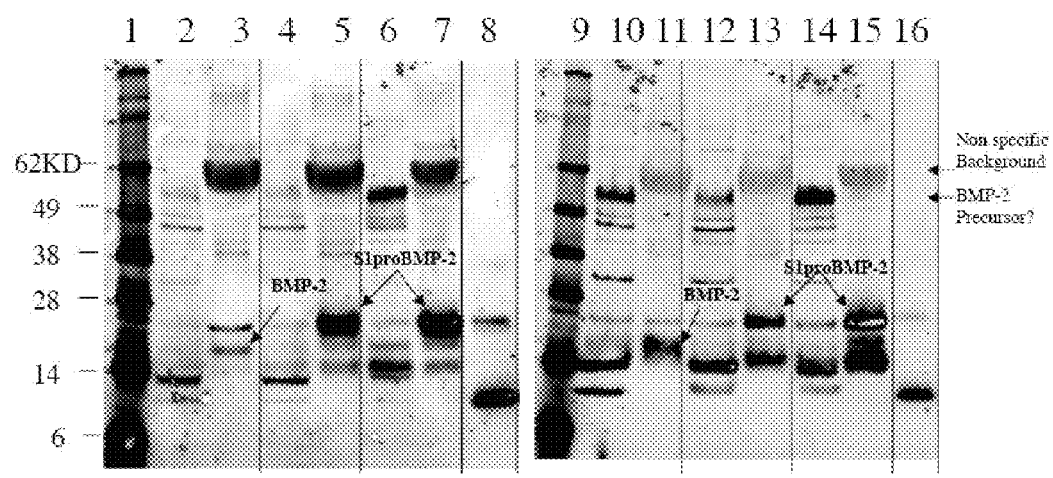
FIG. 28 depicts the results of hBMP-2 western blots of conditioned medium from cell lines transfected with wt hBMP-2 or S1prohBMP-2 transgenes.

S1proBMP-2: Replacing the S1 furin cleavage site -REKR- (which correspond to amino acid residues 279 to 282 of SEQ ID NO: 2) in BMP-2 with a synthetic linker of the amino acid sequence -TNGIEGRALDP- (SEQ ID NO: 16) (constructs IND2340 and IND2341) resulted in the expression of a 20-22 kD proBMP-2 in COS-7, CHO and 293 cell lines (FIG. 28). While the unprocessed precursor could be seen in the lysates the processed S1 proBMP-2 was efficiently secreted into the supernatant.

S2proBMP-2: Mutation of both S1 and the S2 furin site (IND2372) led to the secretion of full length S1S2proBMP-2 in 293 and in COS cells. It runs as a dimer on non-reducing gels.

Figure 29:
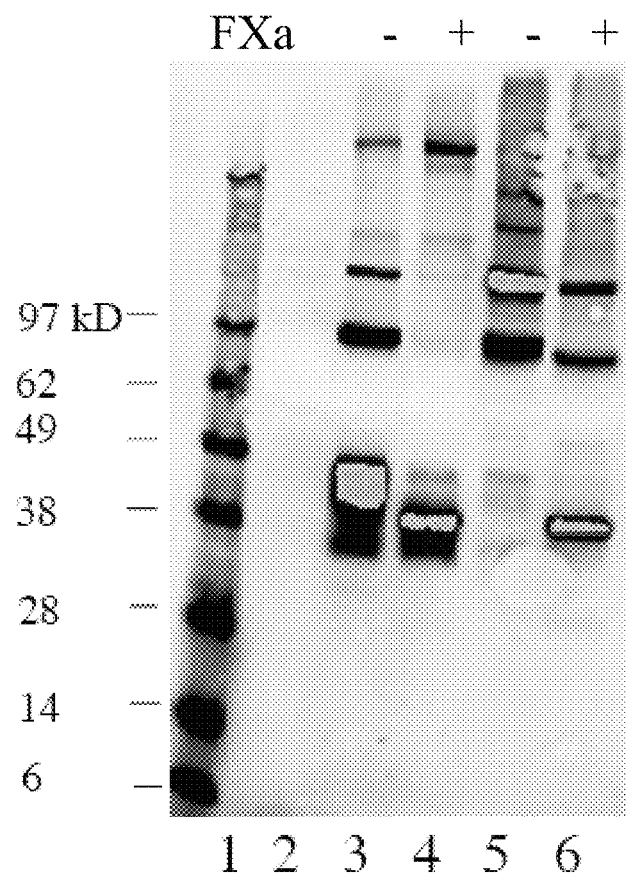
FIG. 29 depicts the results of a hBMP-2 western blot of conditioned medium from a cell lines transfected with the S1proBMP-2 and the S1S2proBMP-2 with and without treatment by Factor Xa.

Cleavage of mutant BMPs S1 proBMP and S1 S2proBMP-2 by Factor Xa produced a mature BMP-2 that remained a dimer under non-reducing conditions with an apparent molecular weight of 30-32 KD similar to wild type BMP (FIG. 29).

Figure 30:
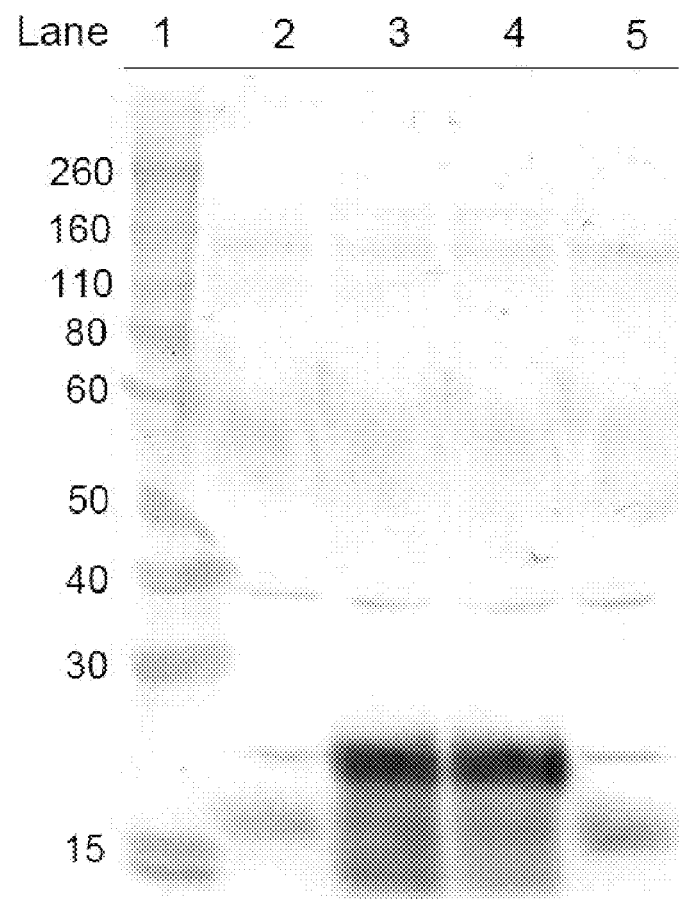
FIG. 30 depicts a hBMP-2 western blot of conditioned medium from 2 cell lines expressing wt hBMP-2 and 2 cell lines expressing S1proBMP-2 transgenes.

Comparison of the Amounts of BMP Secreted from Wild Type and Mutant BMP Expressing Cells When levels of secreted BMP-2 were compared between the mutant and wild type BMPs produced in the same cells was compared by Western blot it was repeated noted that there was significantly more BMP present in the mutated cultures (FIGS. 28 and 30).

Figure 31:
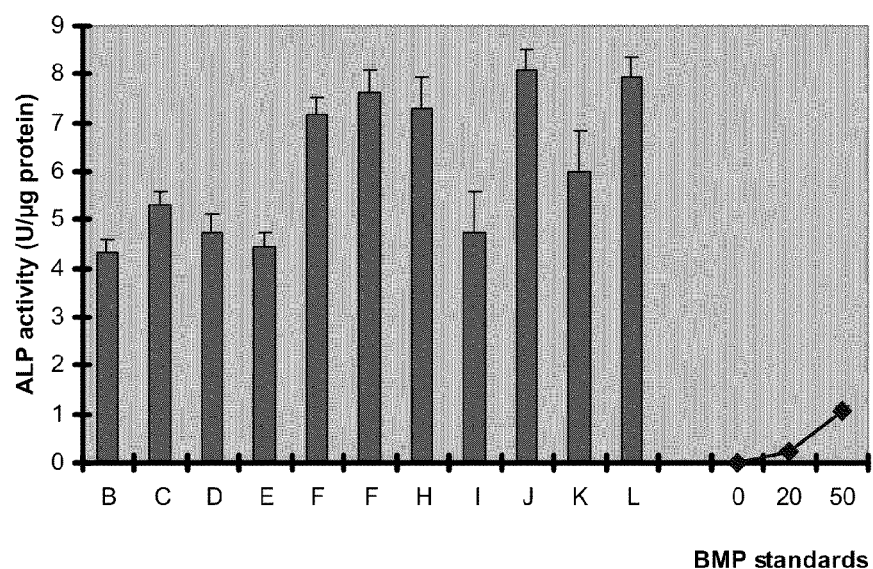
FIG. 31 depicts the results of a cell based BMP activity assay of conditioned medium from 11 S1 proBMP-2 transfected cell lines.

When attempts were made to quantitate the amount of S1 proBMP in the conditioned medium it was discovered that the ELISA did not detect S1 proBMP. Therefore the amount of BMP secreted was quantitated using a dot blot assay. This indicated that the mutated proBMP was being secreted at levels of between 0.5 and 5 µg/ml, approximately 5 to 100 times higher than in the wild type controls (FIG. 31).

Figure 32:
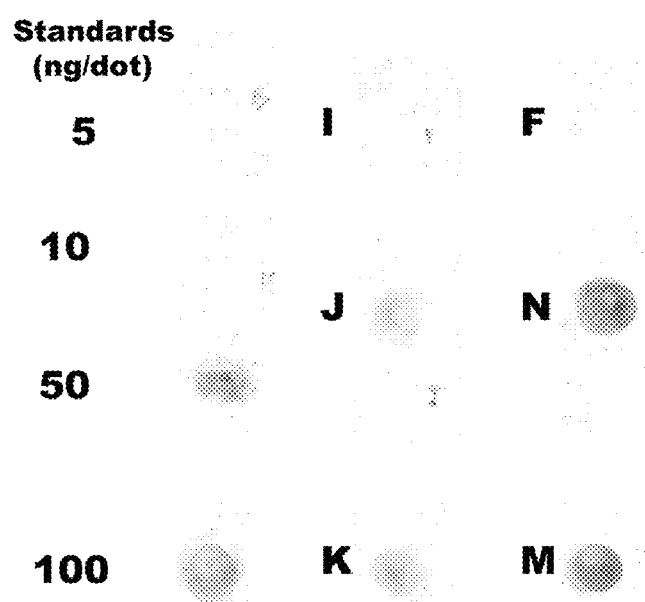
FIG. 32 depicts the dot blot assay results for hBMP-2 in conditioned medium of cells expressing a PC-resistant-hBMP-2 transgene.

The biological activity of these samples was also tested and they were found to be biologically active (FIG. 32). Estimates of the amount of BMP present based on activity were similar to those estimated by dot blot. The results are summarized in Table 2

TABLE 2

| Sample ID | Gene(s) inserted | DNA | Cell Type | mRNA expression | BMP-2 ELISA | BMP-2 Dot Blot |
|---|---|---|---|---|---|---|
| A | hBMP-2 | 2334 | 293 | yes | yes | 76.0 | ND |
| B | " | 2334 | 293 | yes | yes | 0.0 | ND |
| C | " | 2334 | COS | yes | yes | 20.8 | ND |
| D | " | 2334 | 293 | yes | yes | 207 | ND |
| E | " | 2334 | 293 | yes | yes | 55.8 | ND |
| J | S1-BMP-2 | 2340 | COS | yes | yes | 0.3 | 500+ |
| K | " | 2340 | 293 | yes | Yes, 2 bands | 1.5 | 500+ |
| L | | Plasmid only | COS | — | — | 0.0 | 0 |
| M | " | 2341 | COS | Yes | Yes | 1.3 | 5000+ |
| N | " | 2341 | 293 | Yes | Yes, 2 bands | 3.2 | 5000+ |

2334 = wt hBMP-2;
2340 = mutated proBMP-2 in pCNDA3 vector;
2341 = mutated proBMP-2 in pCNDA5 vector
ND = not done Example 5

Resistance of rhBMP Biological Activity to PreScission Digestion

To identify which enzymes could be used to process PC resistant mutant recombinant pro-protein containing an inserted enzyme cleavage site without impairing the activity of the recombinant protein the candidate enzymes could be screened by treating wild type recombinant protein with the enzymes under the recommended cleavage conditions and then be tested for activity.

For example, the resistance of recombinant human BMP-2 and BMP-7 activity to treatment with PreScission protease was investigated.

Materials and Methods

Preparation of test materials: PreScission protease was obtained from Amersham Biosciences (GE Healthcare, Buckinghamshire, U.K) and was prepared according to the manufacturer's instructions. Recombinant hBMP-2 and rhBMP-7 (both CHO cell produced) were obtained from R&D Systems. The rhBMP samples were resuspended in 4 mM HCl to a final concentration of 10 μg/ml. Bovine serum albumin (BSA) was not included so that the only substrate for the protease was BMP. The cleavage buffer was prepared (50 mM Tris-HCl, 150 mM NaCl, 1 mM EDTA, pH 7).

Assessment of activity: Samples underwent digestion at room temperature for 6 hours. Reactions were stopped by freezing at −20° C. Digestion samples were diluted in alpha MEM+15% FBS and tested for BMP activity using the C2C12 assay described in Example 1.

Results and Discussion

The results demonstrated that both rhBMP-2 and rhBMP-7 treated with PreScission remained active after digestion at room temperature for 6 hours. No loss of activity was seen in comparison to control BMP incubated in cleavage buffer alone, although there was a 30 to 30% decline in activity compared to unincubated BMP. These results indicate that the rhBMPs are resistant to PreScission cleavage, although to retain maximum activity cleavage conditions may need to be altered, i.e., by performing the reaction at 4° C.

Once the candidate enzymes have been identified then the appropriate cleavage site mutant can be generated, the yields of recombinant protein in the conditioned medium, and following processing of the purified protein with the enzyme as described in Example 4.

| Group | n | rhBMP-2 (10 μg/ml) (μl) | Precission Protease (μl) | Cleavage Buffer (μl) | ALP activity (U/μg protein) mean ± SD |
|---|---|---|---|---|---|
| 1 | 4 | — | — | — | 2.6 ± 0.5 |
| 2 | 4 | 20 | — | — | 19.0 ± 2.0 |
| 3 | 4 | 20 | 15 | 165 | 12.5 ± 1.0 |
| 4 | 4 | 20 | — | 180 | 12.0 ± 0.5 |
| 5 | 4 | — | 15 | 185 | 2.0 ± 0.5 |
| | | rhBMP-7 (10 μg/ml) (μl) | | | |
| 1 | 4 | — | — | — | 1.6 ± 0.2 |
| 2 | 4 | 20 | — | — | 7.1 ± 0.5 |
| 3 | 4 | 20 | 15 | 165 | 2.9 ± 0.2 |
| 4 | 4 | 20 | — | 180 | 4.0 ± 0.3 |
| 5 | 4 | — | 15 | 185 | 1.5 ± 0.1 |

Example 6

Conversion of Wild Type proBMP-2 to Mature BMP-2 by In Vitro Treatment with Furin Materials & Methods Conditioned medium from CHO-BMP-2 cells prepared in Example 1 was collected and fractionated in a non-reduced polyacrylamide gel. Bands corresponding to the position of the proBMP seen in western blots was excised and crushed and the protein eluted with PBS.

The amount of proBMP eluted was then estimated by dot blot as described in Example 4.

One hundred μl CHO cell produced proBMP-2 (with concentration of approximately 4 ng/ml) was incubated with 10 μl of furin (2 units/μl; Sigma cat #) in 90 μl of cleavage buffer (200 mM HEPES, 0.5% Triton X-100, 2 mM CaCl2, 2 mM mercaptoethanol; pH 7.5) at 30° C. One hundred μl proBMP-2 added to 100 μl of cleavage buffer (no furin) was used as negative control. Twenty μl aliquots of the mixture were sampled at 4, 8, 12, and 24 hr time intervals. These samples were frozen at −20° C. to stop the furin activity. ProBMP-2 from *E. coli*, (Scil Proteins) was used as a negative control.

Results

Figure 33:
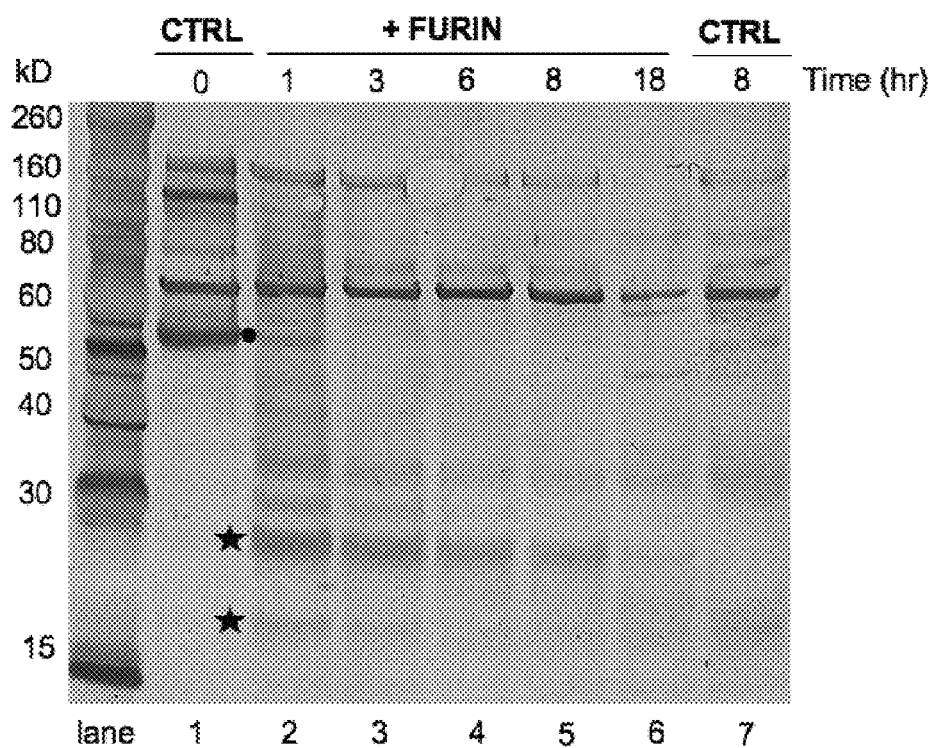
FIG. 33 depicts a hBMP-2 western blot of proBMP-2 purified from conditioned medium from CHO-BMP-2 cells following treatment with furin.

Five media samples treated with furin for 1, 3, 6, 8, and 18 hr and two samples without furin treatment (controls) were analyzed by Western blots. Incubation of the reduced blot with anti-BMP-2 antibodies (PA0025) showed an immunoreactive band throughout all media samples tested (FIG. 33). This band was estimated to be 67 kDa from the MW standard. In addition, we also observed a second band at approximately 55 kDa, particularly clear in the purified proBMP-2 sample without furin treatment at time 0 hr (lane 1). This 55 kDa band was visible although much lighter in the sample with 1 hr furin treatment (lane 2). For samples incubated with furin for more than 3 hr, the 55 kDa band was no longer observed on the blot. Furthermore, two immunoreactive bands with lower molecular weights approximately 22 kDa and 18 kDa were observed only in furin treated samples (lane 2 to 6). Both 22 kDa and 18 kDa band were darkest in the sample with 1 hr furin treatment (lane 2) and got lighter as the incubation time increased.

Western blot results showed the purified CHO proBMP-2 monomers migrated at approximately 55 kDa were cleaved after 1 hr incubation with furin. It appeared that two different forms of BMP-2 monomers, 22 kDa (majority) and 18 kDa, resulted from furin cleavage.

Example 7

An In Vivo Assay to Test the Osteoinductive Activity of BMPs

The inventors have improved the quantitation of induced heterotropic bone formation in mice by using a micro-CT scanner as compared to the evaluation of radiographs and histomorphometric analysis of light microscopic slides as was described in the art (see, e.g., Becker et al. *J Periodontol* 1996; 67:1025-1033 and Kawai and Urist. *Clin. Orthop. Relat. Res.* 1988; 233:262-267) and described below.

Materials & Methods

The osteoinductive capacity of recombinant hBMP-2 protein is measured using the mouse implantation model of osteoinduction, which has been described (see, for example, Urist et al. *Meth Enzym.* 1987;146; 294-312).

Test BMP samples include rhBMP-2 or rhBMP-7 samples with carriers. The carriers include BMP co-lyophilized with atelopeptide type I collagen carrier (Collagen Corp Paulo Alto Calif. (rhBMP-2), or OP-1 implants (rhBMP-7) Stryker Kalamazoo, Mich.); BMP in solution added to atelopepetide type I collagen carrier (Infuse implants (rhBMP-2), Medtronic, Minneapolis, Minn., or Collagen Corp rhBMP-7); BMP co-lyophilized with a collagen carrier; BMP lyophilized on an alloplast (ceramic, calcium phosphate, polymer or metal); and BMP in solution applied to an alloplast.

Swiss-Webster mice (Harlan Sprague-Dawley, Indianapolis, Ind.) are anesthetized by isoflurane gas and placed on the table in a prone position. A 1 by 2 cm site is shaved in the dorsum of the lumbar spine extending over both hips. The site is prepared with 70% alcohol solution. A 10 mm skin incision is made perpendicular to the lumbar spine and muscle pouches were created in each hind quarter. The BMP implant, placed in no. 5 gelatin capsules (Torpac Inc. Fairfield, N.J.), is implanted in the muscle pouches and the wounds closed with metal clips (Poper, Long Island, N.Y.).

Animals receive a BMP-2 capsule implant in one hind quarter muscle mass, with the contralateral muscle mass being implanted with the carrier alone.

The animals were killed 4 weeks post-implantation and the hind quarters are dissected from the torso for radiographic examinations (Faxitron, Field Emission Corporation, McMinnville, Oreg.; 25 kVp, 0.6 sec.). The specimens were then fixed in buffered neutral 10% formalin for a minimum of 24 hours prior to microCT analysis. Following microCT analysis (described below) the implants were excised and embedded in paraffin. Six micron sections were prepared and stained with hematoxylin-eosin or toludine blue.

Microradiographs of histologically valid bone deposits are analyzed by using Image Pro Plus image analysis software (Media Cybernetics, Inc., Silver Spring, Md.) as has been described (see, e.g., Becker et al. *J Periodontol* 1996; 67:1025-1033 and Kawai and Urist. *Clin. Orthop. Relat. Res.* 1988; 233:262-267). The radiopaque area of the implant is expressed as a percentage of the total area of adjacent tissues of the ipsilateral femur. Histomorphometric methods are applied by using the same image analysis software. The volume of new bone and cartilage formed is compared with the total volume of the implant and expressed as a percentage.

MicroCT Analysis of BMP Induced Bone Formation

The hind quarters are imaged using a microCT scanner (eXplore Locus, GE Healthcare, London, ON, CANADA). Micro CT is a technique that uses x-rays to generate a series of radiographs along three planes of a specimen, which are later digitized and used to create a 3D computer model that enables the evaluation of the induced bone.

Figure 34:
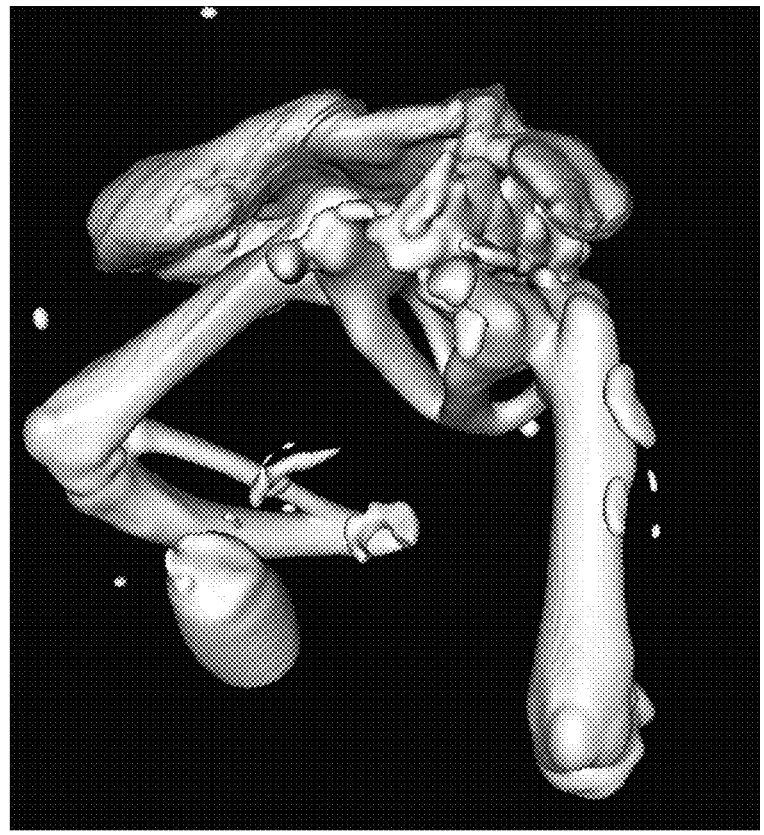
FIG. 34 depicts a microCT image of BMP induced bone ossicle formed in the in vivo mouse muscle pouch BMP assay.

Once the 3D construct has been produced the ossicle of included bone caused by the BMP implant is outlined as a region of interest (ROI). All analysis was restricted to this ROI (see FIG. 34).

This ROI however, is not pure bone, and also includes the volume occupied by blood, muscle tissue and fat. To exclude these less dense tissues from the measurement, a threshold value of 20% of the bone standard included in each micro CT scan was used as the cut off density value, giving a measurement of the bone volume. We use a percentage of the bone standard as a threshold, rather than an absolute value in order to control for the scan to scan variability that was observed.

This method is more sensitive and provides better resolution than microradiographs and provides volume measurements compared to area measurements provided by microradiographs or histological analysis. Consequently the quantitation of induced bone using microCT is more accurate than that estimated from microradiographs.

Figure 35:
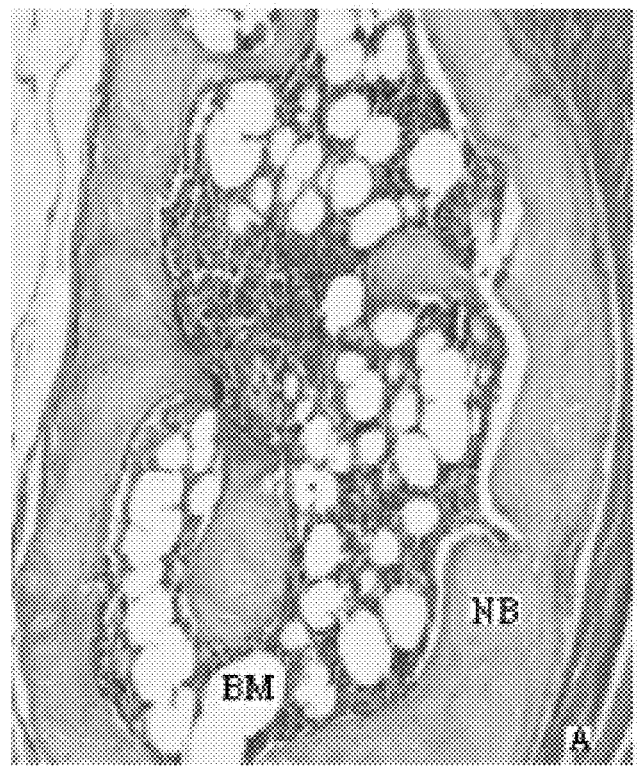
FIG. 35 depicts a histological section of a BMP induced bone ossicle formed in the in vivo mouse muscle pouch BMP assay.

Once the microCT analysis was completed the implants are excised and embedded in paraffin. Ten micron sections are prepared and stained with hematoxylin-eosin or toludine blue (FIG. 35). The amount of bone in these sections could then be determined by histomorphometry using Image ProPlus software (Media Cybernetics Bethesda Md.).

Results

The total induced bone was evaluated by micro CT using seven standard bone quantity and bone quality parameters (total volume of the ROI (TV) bone mineral content within the ROI (BMC), bone mineral density (BMD), bone volume (BV), tissue mineral content (TMC), tissue mineral density (TMD) and bone volume fraction (BVF).

The amount of bone produced by the BMP is indicated by the measurements for TV, BV, BMC and TMC. The quality of the bone is evaluated by the measurements of BMD, TMD and BVF.

Figure 36:
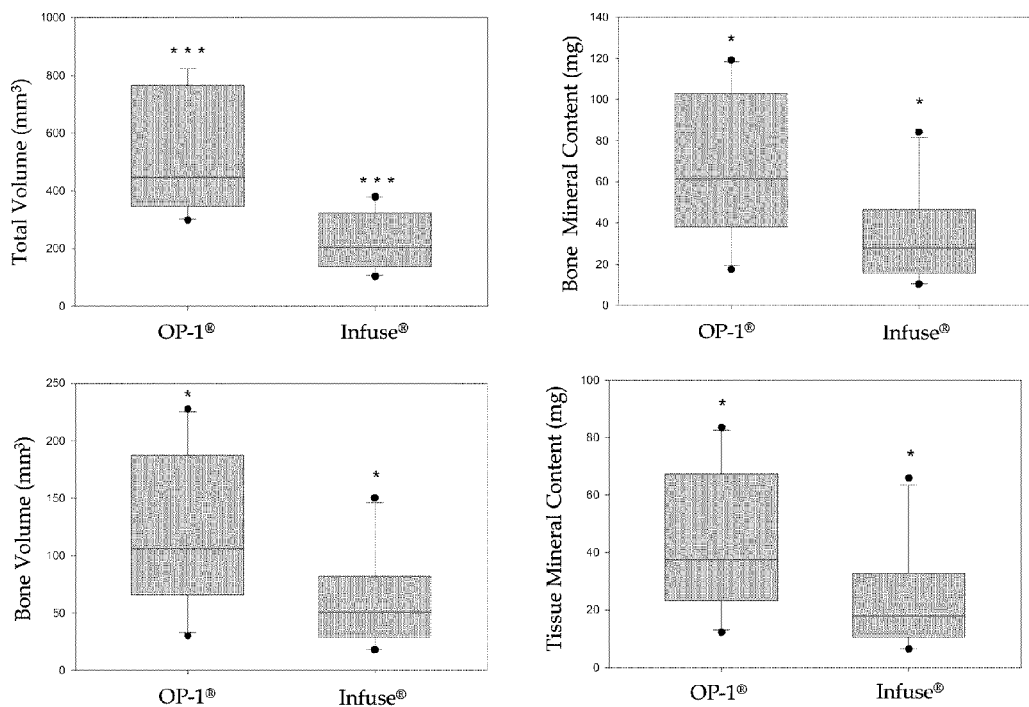
FIG. 36 depicts the microCT analysis of BMP induced bone formation caused by 2 different BMP containing bioimplants.

When comparing BMP-2 containing Infuse implants and BMP-7 containing OP-1 implants the mean values for the OP-1® treated mice were significantly higher than those treated with Infuse® with regards to total volume ($P=<0.001$), bone volume ($P=0.031$ using the Mann-Whitney Rank Sum Test, MWRST), bone mineral content ($P=0.023$), and tissue mineral content ($P=0.045$ using the MWRST) (see FIG. 36).

No significant differences were found between the mean values of OP-1® and Infuse® treated mice with regards to measures of bone quality, specifically bone mineral density ($P=0.600$), tissue mineral density ($P=0.186$ using the Mann-Whitney Rank Sum Test), and bone volume fraction ($P=0.550$) (See FIG. 36).

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

---

What is claimed is:

1. A method of increasing the production yield of a recombinant protein having a pro-domain, wherein the recombinant protein is bone morphogenetic protein 2 (BMP-2), the method comprising the step of expressing a nucleotide sequence comprising a recombinant gene encoding said recombinant protein in eukaryotic cells and wherein cleavage of the pro-domain of the protein is inhibited or eliminated by mutating the recombinant gene to make the protein resistant to cleavage by a proprotein convertase, wherein the proprotein convertase recognition site REKR, consisting of amino acid residues 279 to 282 of SEQ ID NO: 2, of the recombinant protein is replaced with the amino acid sequence of SEQ ID NO: 16, and wherein said increased production yield is in comparison to the yield obtained using a method in which the cleavage of said pro-domain is not inhibited or eliminated.

2. The method according to claim 1, wherein the bone morphogenetic 2 protein is a mammalian BMP-2.

3. The method according to claim 2, wherein the mammalian BMP-2 is human BMP-2 (hBMP-2).

4. The method according to claim 1, wherein where the eukaryotic cells are mammalian cells.

5. The method according to claim 4, wherein the mammalian cells are derived from cell lines.

6. The method according to claim 5, wherein the cell lines are CHO, HEK293, or COS cell lines.

7. The method according to claim 1, wherein the proprotein convertase is a mammalian proprotein convertase and wherein the mammalian proprotein convertase is Furin, PC1, PC2, PACE 4, PC4, PC5 or PC7.

8. The method according to claim 1, wherein the proprotein convertase is Furin.

* * * * *

SEQUENCE LISTING

```
<160> NUMBER OF SEQ ID NOS: 16

<210> SEQ ID NO 1
<211> LENGTH: 1547
<212> TYPE: DNA
<213> ORGANISM: Homo sapiens

<400> SEQUENCE: 1
ggggacttct tgaacttgca gggagaataa cttgcgcacc ccactttgcg ccggtgcctt     60 tgcccagcg gagcctgctt cgccatctcc gagcccacc gcccctccac tcctcggcct     120
tgcccgacac tgagacgctg ttcccagcgt gaaaagagag actgcgcggc cggcacccgg     180
gagaaggagg aggcaaagaa aaggaacgga cattcggtcc ttgcgccagg tcctttgacc     240
```

```
agagtttttc catgtggacg ctctttcaat ggacgtgtcc ccgcgtgctt cttagacgga      300
ctgcggtctc ctaaaggtcg accatggtgg ccgggacccg ctgtcttcta gcgttgctgc      360
ttccccaggt cctcctgggc ggcgcggctg gcctcgttcc ggagctgggc cgcaggaagt      420
tcgcggcggc gtcgtcgggc cgcccctcat cccagccctc tgacgaggtc ctgagcgagt      480
tcgagttgcg gctgctcagc atgttcggcc tgaaacagag acccaccccc agcagggacg      540
ccgtggtgcc cccctacatg ctagacctgt atcgcaggca ctcaggtcag ccgggctcac      600
ccgccccaga ccaccggttg gagagggcag ccagccgagc caacactgtg cgcagcttcc      660
accatgaaga tctttggaa gaactaccag aaacgagtgg aaaacaacc cggagattct       720 tctttaattt aagttctatc cccacggagg agtttatcac ctcagcagag cttcaggttt      780
tccgagaaca gatgcaagat gcttaggaa acaatagcag tttccatcac cgaattaata      840
tttatgaaat cataaaacct gcaacagcca actcgaaatt ccccgtgacc agacttttgg      900
acaccaggtt ggtgaatcag aatgcaagca ggtgggaaag ttttgatgtc accccccgctg    960 tgatgcggtg gactgcacag ggacacgcca accatggatt cgtggtggaa gtggcccact     1020
tggaggagaa acaaggtgtc tccaagagac atgttaggat aagcaggtct ttgcaccaag     1080
atgaacacag ctggtcacag ataaggccat tgctagtaac ttttggccat gatggaaaag     1140
ggcatcctct ccacaaaaga gaaaacgtc aagccaaaca caaacagcgg aaacgcctta      1200
agtccagctg taagagacac cctttgtacg tggacttcag tgacgtgggg tggaatgact     1260
ggattgtggc tcccccgggg tatcacgcct tttactgcca cggagaatgc ccttttcctc     1320
tggctgatca tctgaactcc actaatcatg ccattgttca gacgttggtc aactctgtta     1380
actctaagat tcctaaggca tgctgtgtcc cgacagaact cagtgctatc tcgatgctgt     1440
accttgacga gaatgaaaag gttgtattaa agaactatca ggacatggtt gtggagggtt     1500
gtgggtgtcg ctagtacagc aaaattaaat acataaatat atatata              1547
```

<210> SEQ ID NO 2
<211> LENGTH: 396
<212> TYPE: PRT
<213> ORGANISM: Homo sapiens

<400> SEQUENCE: 2

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala

```
                145                 150                 155                 160
Leu Gly Asn Asn Ser Ser Phe His His Arg Ile Asn Ile Tyr Glu Ile
                    165                 170                 175

Ile Lys Pro Ala Thr Ala Asn Ser Lys Phe Pro Val Thr Arg Leu Leu
                180                 185                 190

Asp Thr Arg Leu Val Asn Gln Asn Ala Ser Arg Trp Glu Ser Phe Asp
            195                 200                 205

Val Thr Pro Ala Val Met Arg Trp Thr Ala Gln Gly His Ala Asn His
        210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
                260                 265                 270

Gly His Pro Leu His Lys Arg Glu Lys Arg Gln Ala Lys His Lys Gln
            275                 280                 285

Arg Lys Arg Leu Lys Ser Ser Cys Lys Arg His Pro Leu Tyr Val Asp
        290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
                340                 345                 350

Asn Ser Lys Ile Pro Lys Ala Cys Cys Val Pro Thr Glu Leu Ser Ala
            355                 360                 365

Ile Ser Met Leu Tyr Leu Asp Glu Asn Glu Lys Val Val Leu Lys Asn
        370                 375                 380

Tyr Gln Asp Met Val Val Glu Gly Cys Gly Cys Arg
385                 390                 395

<210> SEQ ID NO 3
<211> LENGTH: 1878
<212> TYPE: DNA
<213> ORGANISM: Homo sapiens

<400> SEQUENCE: 3
gggcgcagcg gggcccgtct gcagcaagtg accgacggcc gggacggccg cctgcccct        60 ctgccacctg gggcggtgcg ggcccggagc ccggagcccg ggtagcgcgt agagccggcg      120
cgatgcacgt gcgctcactg cgagctgcgg cgccgcacag cttcgtggcg ctctgggcac      180
ccctgttcct gctgcgctcc gccctggccg acttcagcct ggacaacgag gtgcactcga      240
gcttcatcca ccggcgcctc cgcagccagg agcggcggga gatgcagcgc gagatcctct      300
ccatttgggg cttgccccac cgcccgcgcc cgcacctcca gggcaagcac aactcggcac      360
ccatgttcat gctggacctg tacaacgcca tggcggtgga ggagggcggc gggcccggcg      420
gccagggctt ctcctacccc tacaaggccg tcttcagtac ccagggcccc cctctggcca      480
gcctgcaaga tagccatttc ctcaccgacg ccgacatggt catgagcttc gtcaacctcg      540
tggaacatga caaggaattc ttccacccac gctaccacca tcgagagttc cggtttgatc      600
tttccaagat cccagaaggg gaagctgtca cggcagccga attccggatc tacaaggact      660
acatccggga acgcttcgac aatgagacgt tccggatcag cgtttatcag gtgctccagg      720
agcacttggg cagggaatcg gatctcttcc tgctcgacag ccgtaccctc tgggcctcgg      780
```

```
aggagggctg gctggtgttt gacatcacag ccaccagcaa ccactgggtg gtcaatccgc    840
ggcacaacct gggcctgcag ctctcggtgg agacgctgga tgggcagagc atcaacccca    900
agttggcggg cctgattggg cggcacgggc cccagaacaa gcagcccttc atggtggctt    960
tcttcaaggc cacggaggtc cacttccgca gcatccggtc cacggggagc aaacagcgca   1020
gccagaaccg ctccaagacg cccaagaacc aggaagccct gcggatggcc aacgtggcag   1080
agaacagcag cagcgaccag aggcaggcct gtaagaagca cgagctgtat gtcagcttcc   1140
gagacctggg ctggcaggac tggatcatcg cgcctgaagg ctacgccgcc tactactgtg   1200 aggggggagtg tgccttccct ctgaactcct acatgaacgc caccaaccac gccatcgtgc   1260
agacgctggt ccacttcatc aacccggaaa cggtgcccaa gccctgctgt gcgcccacgc   1320
agctcaatgc catctccgtc ctctacttcg atgcagcagctc aacgtcatc ctgaagaaat   1380 acagaaacat ggtggtccgg gcctgtggct gccactagct cctccgagaa ttcagaccct   1440
ttggggccaa gttttctgg atcctccatt gctcgccttg gccaggaacc agcagaccaa   1500
ctgccttttg tgagaccttc ccctccctat ccccaacttt aaaggtgtga gagtattagg   1560
aaacatgagc agcatatggc ttttgatcag tttttcagtg gcagcatcca atgaacaaga   1620
tcctacaagc tgtgcaggca aaacctagca ggaaaaaaaa acaacgcata agaaaaatg    1680 gccgggccag gtcattggct gggaagtctc agccatgcac ggactcgttt ccagaggtaa   1740
ttatgagcgc ctaccagcca ggccacccag ccgtgggagg aagggggcgt ggcaaggggt   1800
gggcacattg gtgtctgtgc gaaaggaaaa ttgacccgga agttcctgta ataaatgtca   1860
caataaaacg aatgaatg                                                  1878

<210> SEQ ID NO 4
<211> LENGTH: 431
<212> TYPE: PRT
<213> ORGANISM: Homo sapiens

<400> SEQUENCE: 4

Met His Val Arg Ser Leu Arg Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175
```

```
Tyr Lys Asp Tyr Ile Arg Glu Arg Phe Asp Asn Glu Thr Phe Arg Ile
            180                 185                 190
Ser Val Tyr Gln Val Leu Gln Glu His Leu Gly Arg Glu Ser Asp Leu
        195                 200                 205
Phe Leu Leu Asp Ser Arg Thr Leu Trp Ala Ser Glu Glu Gly Trp Leu
210                 215                 220
Val Phe Asp Ile Thr Ala Thr Ser Asn His Trp Val Val Asn Pro Arg
225                 230                 235                 240
His Asn Leu Gly Leu Gln Leu Ser Val Glu Thr Leu Asp Gly Gln Ser
                245                 250                 255
Ile Asn Pro Lys Leu Ala Gly Leu Ile Gly Arg His Gly Pro Gln Asn
            260                 265                 270
Lys Gln Pro Phe Met Val Ala Phe Lys Ala Thr Glu Val His Phe
        275                 280                 285
Arg Ser Ile Arg Ser Thr Gly Ser Lys Gln Arg Ser Gln Asn Arg Ser
290                 295                 300
Lys Thr Pro Lys Asn Gln Glu Ala Leu Arg Met Ala Asn Val Ala Glu
305                 310                 315                 320
Asn Ser Ser Ser Asp Gln Arg Gln Ala Cys Lys Lys His Glu Leu Tyr
                325                 330                 335
Val Ser Phe Arg Asp Leu Gly Trp Gln Asp Trp Ile Ile Ala Pro Glu
            340                 345                 350
Gly Tyr Ala Ala Tyr Tyr Cys Glu Gly Glu Cys Ala Phe Pro Leu Asn
        355                 360                 365
Ser Tyr Met Asn Ala Thr Asn His Ala Ile Val Gln Thr Leu Val His
370                 375                 380
Phe Ile Asn Pro Glu Thr Val Pro Lys Pro Cys Cys Ala Pro Thr Gln
385                 390                 395                 400
Leu Asn Ala Ile Ser Val Leu Tyr Phe Asp Asp Ser Ser Asn Val Ile
                405                 410                 415
Leu Lys Lys Tyr Arg Asn Met Val Val Arg Ala Cys Gly Cys His
            420                 425                 430

<210> SEQ ID NO 5
<211> LENGTH: 1573
<212> TYPE: DNA
<213> ORGANISM: Homo sapiens

<400> SEQUENCE: 5
tcgacccacg cgtccgggca gaggaggagg gagggaggga aggagcgcgg agcccggccc      60
ggaagctagg agccattccg tagtgccatc ccgagcaacg cactgctgca gcttccctga     120
gcctttccag caagtttgtt caagattggc tgtcaagaat catggactgt tattatatgc     180
cttgttttct gtcaagacac catgattcct ggtaaccgaa tgctgatggt cgttttatta     240
tgccaagtcc tgctaggagg cgcgagccat gctagtttga tacctgagac ggggaagaaa     300
aaagtcgccg agattcaggg ccacgcggga ggacgccgct cagggcagag ccatgagctc     360
ctgcgggact cgaggcgac  acttctgcag atgtttgggc tgcgccgccg cccgcagcct     420
agcaagagtg ccgtcattcc ggactacatg cgggatcttt accggcttca gtctggggag     480
gaggaggaag agcagatcca gcactggtt  cttgagtatc ctgagcgccc ggccagccgg     540
gccaacaccg tgaggagctt ccaccacgaa gaacatctgg agaacatccc aggaccagt      600 gaaaactctg cttttcgttt cctctttaac ctcagcagca tccctgagaa cgaggcgatc     660
tcctctgcag agcttcggct cttccgggag caggtggacc agggccctga ttgggaaagg     720
```

```
ggcttccacc gtataaacat ttatgaggtt atgaagcccc cagcagaagt ggtgcctggg    780
cacctcatca cacgactact ggacacgaga ctggtccacc acaatgtgac acggtgggaa    840
actttttgatg tgagccctgc ggtccttcgc tggacccggg agaagcagcc aaactatggg   900
ctagccattg aggtgactca cctccatcag actcggaccc accagggcca gcatgtcagg    960
attagccgat cgttacctca agggagtggg aattgggccc agctccggcc cctcctggtc   1020
acctttggcc atgatggccg gggccatgcc ttgacccgac gccggagggc caagcgtagc   1080
cctaagcatc actcacagcg ggccaggaag aagaataaga actgccggcg ccactcgctc   1140
tatgtggact tcagcgatgt gggctggaat gactggattg tggccccacc aggctaccag   1200
gccttctact gccatgggga ctgcccctt ccactggctg accacctcaa ctcaaccaac    1260
catgccattg tgcagaccct ggtcaattct gtcaattcca gtatccccaa agcctgttgt   1320
gtgcccactg aactgagtgc catctccatg ctgtacctgg atgagtatga taggtggta   1380
ctgaaaaatt atcaggagat ggtagtagag ggatgtgggt gccgctgaga tcaggcagtc   1440
cttgaggata gacagatata cacaccacac acacacacca catacaccac acacacgt    1500
tcccatccac tcacccacac actacacaga ctgcttcctt atagctggac tttatttaa    1560
aaaaaaaaaa aaa                                                      1573
```

<210> SEQ ID NO 6
<211> LENGTH: 408
<212> TYPE: PRT
<213> ORGANISM: Homo sapiens

<400> SEQUENCE: 6

```
Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
        115                 120                 125

Ile Pro Gly Thr Ser Glu Asn Ser Ala Phe Arg Phe Leu Phe Asn Leu
    130                 135                 140

Ser Ser Ile Pro Glu Asn Glu Ala Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
            180                 185                 190

Gly His Leu Ile Thr Arg Leu Leu Asp Thr Arg Leu Val His His Asn
        195                 200                 205

Val Thr Arg Trp Glu Thr Phe Asp Val Ser Pro Ala Val Leu Arg Trp
    210                 215                 220
```

```
Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
            245                 250                 255

Ser Leu Pro Gln Gly Ser Gly Asn Trp Ala Gln Leu Arg Pro Leu Leu
            260                 265                 270

Val Thr Phe Gly His Asp Gly Arg Gly His Ala Leu Thr Arg Arg Arg
        275                 280                 285

Arg Ala Lys Arg Ser Pro Lys His His Ser Gln Arg Ala Arg Lys Lys
        290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
            355                 360                 365

Pro Lys Ala Cys Cys Val Pro Thr Glu Leu Ser Ala Ile Ser Met Leu
370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405
```

<210> SEQ ID NO 7
<211> LENGTH: 1550
<212> TYPE: DNA
<213> ORGANISM: Homo sapiens

<400> SEQUENCE: 7

| | | | |
|---|---|---|---|
| ggggacttct tgaacttgca gggagaataa cttgcgcacc ccactttgcg ccggtgcctt | 60 |
| tgccccagcg gagcctgctt cgccatctcc gagccccacc gccctccac tcctcggcct | 120 |
| tgcccgacac tgagacgctg ttcccagcgt gaaaagagag actgcgcggc cggcaccccgg | 180 |
| gagaaggagg aggcaaagaa aaggaacgga cattcggtcc ttgcgccagg tcctttgacc | 240 |
| agagtttttc catgtggacg ctcttttcaat ggacgtgtcc ccgcgtgctt cttagacgga | 300 |
| ctgcggtctc ctaaaggtcg accatggtgg ccgggacccg ctgtcttcta gcgttgctgc | 360 |
| ttccccaggt cctcctgggc ggcgcggctg gcctcgttcc ggagctgggc cgcaggaagt | 420 |
| tcgcggcggc gtcgtcgggc cgcccctcat cccagccctc tgacgaggtc ctgagcgagt | 480 |
| tcgagttgcg gctgctcagc atgttcggcc tgaaacagag acccaccccc agcagggacg | 540 |
| ccgtggtgcc ccctacatg ctagacctgt atcgcaggca ctcaggtcag ccgggctcac | 600 |
| ccgccccaga ccaccggttg gagagggcag ccagccgagc caacactgtg cgcagcttcc | 660 |
| accatgaaga atctttggaa gaactaccag aaacgagtgg gaaaacaacc cggagattct | 720 |
| tctttaattt aagttctatc cccacggagg agtttatcac ctcagcagag cttcaggttt | 780 |
| tccgagaaca gatgcaagat gctttaggaa acaatagcag tttccatcac cgaattaata | 840 |
| tttatgaaat cataaaacct gcaacagcca actcgaaatt ccccgtgacc agactttttgg | 900 |
| acaccaggtt ggtgaatcag aatgcaagca ggtgggaaag ttttgatgtc accccgctg | 960 |
| tgatgcggtg gactgcacag ggacacgcca ccatggatt cgtggtggaa gtggccact | 1020 |
| tggaggagaa acaaggtgtc tccaagagac atgttaggat aagcaggtct ttgcaccaag | 1080 |

```
atgaacacag ctggtcacag ataaggccat tgctagtaac ttttggccat gatggaaaag    1140
ggcatcctct ccacctggaa gtgctgtttc agggcccgaa acataaacag cggaaacgcc    1200
ttaagtccag ctgtaagaga cacccttgt acgtggactt cagtgacgtg gggtggaatg     1260
actggattgt ggctccccg gggtatcacg ccttttactg ccacggagaa tgcccttttc     1320
ctctggctga tcatctgaac tccactaatc atgccattgt tcagacgttg gtcaactctg    1380
ttaactctaa gattcctaag gcatgctgtg tcccgacaga actcagtgct atctcgatgc    1440
tgtaccttga cgagaatgaa aaggttgtat taaagaacta tcaggacatg gttgtggagg    1500
gttgtgggtg tcgctagtac agcaaaatta aatacataaa tatatatata              1550
```

<210> SEQ ID NO 8
<211> LENGTH: 397
<212> TYPE: PRT
<213> ORGANISM: Homo sapiens

<400> SEQUENCE: 8

```
Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Ile Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Leu Glu Val Leu Phe Gln Gly Pro Lys His Lys
        275                 280                 285

Gln Arg Lys Arg Leu Lys Ser Ser Cys Lys Arg His Pro Leu Tyr Val
    290                 295                 300
```

```
Asp Phe Ser Asp Val Gly Trp Asn Asp Trp Ile Val Ala Pro Pro Gly
305                 310                 315                 320

Tyr His Ala Phe Tyr Cys His Gly Glu Cys Pro Phe Pro Leu Ala Asp
                325                 330                 335

His Leu Asn Ser Thr Asn His Ala Ile Val Gln Thr Leu Val Asn Ser
            340                 345                 350

Val Asn Ser Lys Ile Pro Lys Ala Cys Cys Val Pro Thr Glu Leu Ser
        355                 360                 365

Ala Ile Ser Met Leu Tyr Leu Asp Glu Asn Glu Lys Val Val Leu Lys
    370                 375                 380

Asn Tyr Gln Asp Met Val Val Glu Gly Cys Gly Cys Arg
385                 390                 395

<210> SEQ ID NO 9
<211> LENGTH: 1547
<212> TYPE: DNA
<213> ORGANISM: Homo sapiens

<400> SEQUENCE: 9
ggggacttct tgaacttgca gggagaataa cttgcgcacc ccactttgcg ccggtgcctt     60
tgccccagcg gagcctgctt cgccatctcc gagccccacc gcccctccac tcctcggcct    120
tgcccgacac tgagacgctg ttcccagcgt gaaaagagag actgcgcggc cggcacccgg    180
gagaaggagg aggcaaagaa aaggaacgga cattcggtcc ttgcgccagg tcctttgacc    240
agagttttc catgtggacg ctctttcaat ggacgtgtcc ccgcgtgctt cttagacgga    300
ctgcggtctc ctaaaggtcg accatggtgg ccgggacccg ctgtcttcta gcgttgctgc    360
ttcccccaggt cctcctgggc ggcgcggctg gcctcgttcc ggagctgggc cgcaggaagt    420
tcgcggcggc gtcgtcgggc cgcccctcat cccagccctc tgacgaggtc ctgagcgagt    480
tcgagttgcg gctgctcagc atgttcggcc tgaaacagag acccaccccc agcagggacg    540
ccgtggtgcc ccctacatg ctagacctgt atcgcaggca ctcaggtcag ccgggctcac    600
ccgccccaga ccaccggttg gagagggcag ccagccgagc caacactgtg cgcagcttcc    660
accatgaaga atctttggaa gaactaccag aaacgagtgg aaaacaacc cggagattct    720
tctttaattt aagttctatc cccacggagg agtttatcac ctcagcagag cttcaggttt    780
tccgagaaca gatgcaagat gctttaggaa acaatagcag tttccatcac cgaattaata    840
tttatgaaat cataaaacct gcaacagcca actcgaaatt ccccgtgacc agactttttgg    900
acaccaggtt ggtgaatcag aatgcaagca ggtgggaaag ttttgatgtc accccgctg    960
tgatgcggtg gactgcacag ggacacgcca accatggatt cgtggtggaa gtggcccact   1020
tggaggagaa acaaggtgtc tccaagagac atgttgcgat aagcaggtct ttgcaccaag   1080
atgaacacag ctggtcacag ataaggccat tgctagtaac ttttggccat gatggaaaag   1140
ggcatcctct ccacaaagca gaaaaacgtc aagccaaaca caaacagcgg aaacgcctta   1200
agtccagctg taagagacac cctttgtacg tggacttcag tgacgtgggg tggaatgact   1260
ggattgtggc tccccgggg tatcacgcct tttactgcca cggagaatgc ccttttcctc    1320
tggctgatca tctgaactcc actaatcatg ccattgttca gacgttggtc aactctgtta   1380
actctaagat tcctaaggca tgctgtgtcc cgacagaact cagtgctatc tcgatgctgt   1440
accttgacga gaatgaaaag gttgtattaa agaactatca ggacatggtt gtggagggtt   1500
gtgggtgtcg ctagtacagc aaaattaaat acataaatat atatata                 1547
```

-continued

```
<210> SEQ ID NO 10
<211> LENGTH: 396
<212> TYPE: PRT
<213> ORGANISM: Homo sapiens

<400> SEQUENCE: 10

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Ala Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Ala Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Val Leu Lys Asn
    370                 375                 380

Tyr Gln Asp Met Val Val Glu Gly Cys Gly Cys Arg
```

<210> SEQ ID NO 11
<211> LENGTH: 1881
<212> TYPE: DNA
<213> ORGANISM: Homo sapiens

<400> SEQUENCE: 11

```
gggcgcagcg gggcccgtct gcagcaagtg accgacggcc gggacggccg cctgccccct      60
ctgccacctg gggcggtgcg ggcccggagc ccggagcccg ggtagcgcgt agagccggcg     120
cgatgcacgt gcgctcactg cgagctgcgg cgccgcacag cttcgtggcg ctctgggcac     180
ccctgttcct gctgcgctcc gccctggccg acttcagcct ggacaacgag gtgcactcga     240
gcttcatcca ccgcgcctc cgcagccagg agcggcggga gatgcagcgc gagatcctct     300
ccattttggg cttgccccac cgcccgcgcc cgcacctcca gggcaagcac aactcggcac     360
ccatgttcat gctggacctg tacaacgcca tggcggtgga ggaggcggc gggcccggcg     420
gccagggctt ctcctacccc tacaaggccg tcttcagtac ccagggcccc cctctggcca     480
gcctgcaaga tagccatttc ctcaccgacg ccgacatggt catgagcttc gtcaacctcg     540
tggaacatga caaggaattc ttccacccac gctaccacca tcgagagttc cggtttgatc     600
tttccaagat cccagaaggg gaagctgtca cggcagccga attccggatc tacaaggact     660
acatccggga acgcttcgac aatgagacgt tccggatcag cgtttatcag gtgctccagg     720
agcacttggg cagggaatcg gatctcttcc tgctcgacag ccgtaccctc tgggcctcgg     780
aggagggctg gctggtgttt gacatcacag ccaccagcaa ccactgggtg gtcaatccgc     840
ggcacaacct gggcctgcag ctctcggtgg agacgctgga tgggcagagc atcaacccca     900
agttggcggg cctgattggg cggcacgggc cccagaacaa gcagcccttc atggtggctt     960
tcttcaaggc cacggaggtc cacttcctgg aagtgctgtt tcagggcccg aaacatcagc    1020
gcagccagaa ccgctccaag acgcccaaga accaggaagc cctgcggatg ccaacgtgg    1080
cagagaacag cagcagcgac cagaggcagg cctgtaagaa gcacgagctg tatgtcagct    1140
tccgagacct gggctggcag gactggatca tcgcgcctga aggctacgcc gcctactact    1200
gtgaggggga gtgtgccttc cctctgaact cctacatgaa cgccaccaac cacgccatcg    1260
tgcagacgct ggtccacttc atcaacccgg aaacggtgcc caagccctgc tgtgcgccca    1320
cgcagctcaa tgccatctcc gtcctctact tcgatgacag ctccaacgtc atcctgaaga    1380
aatacagaaa catggtggtc cgggcctgtg gctgccacta gctcctccga gaattcagac    1440
ccttggggc caagtttttc tggatcctcc attgctcgcc ttggccagga accagcagac    1500
caactgcctt ttgtgagacc ttcccctccc tatcccaac tttaaggtg tgagagtatt    1560
aggaaacatg agcagcatat ggcttttgat cagttttca gtggcagcat ccaatgaaca    1620
agatcctaca agctgtgcag gcaaaaccta gcaggaaaaa aaaacaacgc ataaagaaaa    1680
atggccgggc caggtcattg gctgggaagt ctcagccatg cacggactcg tttccagagg    1740
taattatgag cgcctaccag ccaggccacc cagccgtggg aggaaggggg cgtggcaagg    1800
ggtgggcaca ttggtgtctg tgcgaaagga aaattgaccc ggaagttcct gtaataaatg    1860
tcacaataaa acgaatgaat g                                              1881
```

<210> SEQ ID NO 12
<211> LENGTH: 433
<212> TYPE: PRT
<213> ORGANISM: Homo sapiens -continued

<400> SEQUENCE: 12

```
Met His Val Arg Ser Leu Arg Ala Ala Pro His Ser Phe Val Ala
1               5                   10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
                100                 105                 110

Thr Gln Gly Pro Pro Leu Ala Ser Leu Gln Asp Ser His Phe Leu Thr
            115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
275                 280                 285

Leu Glu Val Leu Phe Gln Gly Pro Gly Ser Lys Gln Arg Ser Gln Asn
            290                 295                 300

Arg Ser Lys Thr Pro Lys Asn Gln Glu Ala Leu Arg Met Ala Asn Val
305                 310                 315                 320

Ala Glu Asn Ser Ser Ser Asp Gln Arg Gln Ala Cys Lys Lys His Glu
                325                 330                 335

Leu Tyr Val Ser Phe Arg Asp Leu Gly Trp Gln Asp Trp Ile Ile Ala
            340                 345                 350

Pro Glu Gly Tyr Ala Ala Tyr Tyr Cys Glu Gly Glu Cys Ala Phe Pro
355                 360                 365

Leu Asn Ser Tyr Met Asn Ala Thr Asn His Ala Ile Val Gln Thr Leu
370                 375                 380

Val His Phe Ile Asn Pro Glu Thr Val Pro Lys Pro Cys Cys Ala Pro
385                 390                 395                 400

Thr Gln Leu Asn Ala Ile Ser Val Leu Tyr Phe Asp Asn Ser Ser Asn
            405                 410                 415
```

```
             Val Ile Leu Lys Lys Tyr Arg Asn Met Val Val Arg Ala Cys Gly Cys
                             420                 425                 430

His

<210> SEQ ID NO 13
<211> LENGTH: 4180
<212> TYPE: DNA
<213> ORGANISM: Homo sapiens

<400> SEQUENCE: 13
gcggggaagc agcagcggcc aggatgaatc ccaggtgctc tggagctgga tggtgaaggt      60
cggcactctt caccctcccg agccctgccc gtctcggccc catgccccca ccagtcagcc     120
ccgggccaca ggcagtgagc aggcacctgg gagccgaggc cctgtgacca ggccaaggag     180
acgggcgctc cagggtccca gccacctgtc cccccatggg agctgaggcc ctggttgcta     240
tgggtggtag cagcaacagg aaccttggtc ctgctagcag ctgatgctca gggccagaag     300
gtcttcacca acacgtgggc tgtgcgcatc cctggaggcc cagcggtggc caacagtgtg     360
gcacggaagc atgggttcct caacctgggc cagatcttcg ggactatta ccacttctgg     420 catcgaggag tgacgaagcg gtccctgtcg cctcaccgcc cgcggcacag ccggctgcag     480
agggagcctc aagtacagtg gctggaacag caggtggcaa agcgacggac taaacgggac     540
gtgtaccagg agcccacaga ccccaagttt cctcagcagt ggtacctgtc tggtgtcact     600
cagcgggacc tgaatgtgaa ggcggcctgg gcgcagggct acacagggca cggcattgtg     660
gtctccattc tggacgatgg catcgagaag aaccacccgg acttggcagg caattatgat     720
cctggggcca gttttgatgt caatgaccag gaccctgacc ccagcctcg gtacacacag     780 atgaatgaca caggcacgg cacacggtgt gcggggaag tggctgcggt ggccaacaac     840
ggtgtctgtg gtgtaggtgt ggcctacaac gcccgcattg agggtgcg catgctggat     900 ggcgaggtga cagatgcagt ggaggcacgc tcgctgggcc tgaaccccaa ccacatccac     960
atctacagtg ccagctgggg ccccgaggat gacggcaaga cagtggatgg ccagcccgc    1020 ctcgccgagg aggcctttct ccgtgggggtt agccagggcc aggggggct gggctccatc    1080 tttgtctggg cctcggggaa cggggggccgg gaacatgaca gctgcaactg cgacggctac    1140
accaacagta tctacacgct gtccatcagc agcgccacgc agtttggcaa cgtgccgtgg    1200
tacagcgagg cctgctcgtc cacactggcc acgacctaca gcagtggcaa ccagaatgag    1260
aagcagatcg tgacgactga cttgcggcag aagtgcacgg agtctcacac gggcacctca    1320
gcctctgccc ccttagcagc cggcatcatt gctctcaccc tggaggccaa taagaacctc    1380
acatggcggg acatgcaaca cctggtggta cagacctcga gccagccca cctcaatgcc    1440 aacgactggg ccaccaatgg tgtgggccgg aaagtgagcc actcatatgg ctacgggctt    1500
ttggacgcag cgccatggt ggccctggcc cagaattgga ccacagtggc ccccagcgg    1560 aagtgcatca tcgacatcct caccgagccc aaagacatcg ggaaacggct cgaggtgcgg    1620
aagaccgtga ccgcgtgcct gggcgagccc aaccacatca ctcggctgga gcacgctcag    1680
gcgcggctca ccctgtccta taatcgccgt ggcgacctgg ccatccacct ggtcagcccc    1740
atgggcaccc gctccaccct gctggcagcc aggccacatg actactccgc agatgggttt    1800
aatgactggg ccttcatgac aactcattcc tgggatgagg atcccctctgg cgagtgggtc    1860 ctagagattg aaaacaccag cgaagccaac aactatggga cgctgaccaa gttcaccctc    1920
gtactctatg gcaccgcccc tgaggggctg ccgtacctc cagaaagcag tggctgcaag    1980
accctcacgt ccagtcaggc ctgtgtggtg tgcgaggaag gcttctccct gcaccagaag    2040
```

```
agctgtgtcc agcactgccc tccagggttc gcccccaag tcctcgatac gcactatagc    2100
accgagaatg acgtggagac catccgggcc agcgtctgcg cccctgcca cgcctcatgt    2160
gccacatgcc aggggccggc cctgacagac tgcctcagct gccccagcca cgcctccttg    2220
gaccctgtgg agcagacttg ctcccggcaa agccagagca gccgagagtc cccgccacag    2280
cagcagccac ctcggctgcc cccggaggtg gaggcgggc aacggctgcg ggcagggctg    2340
ctgccctcac acctgcctga ggtggtggcc ggcctcagct gcgccttcat cgtgctggtc    2400
ttcgtcactg tcttcctggt cctgcagctg cgctctggct ttagttttcg ggggtgaag    2460
gtgtacacca tggaccgtgg cctcatctcc tacaagggc tgccccctga agcctggcag    2520
gaggagtgcc cgtctgactc agaagaggac gagggccggg gcgagaggac cgcctttatc    2580
aaagaccaga gcgccctctg atgagcccac tgcccacccc ctcaagccaa tcccctcctt    2640
gggcactttt taattcacca aagtattttt ttatcttggg actgggtttg acccccagct    2700
gggaggcaag aggggtggag actgcttccc atcctaccct cgggcccacc tggccacctg    2760
aggtgggccc aggaccagct ggggcgtggg gagggccgta ccccaccctc agcaccccctt   2820
ccatgtggag aaaggagtga aacctttagg gcagcttgcc ccggcccgg ccccagccag    2880
agttcctgcg gagtgaagag gggcagccct tgcttgttgg gattcctgac ccaggccgca    2940
gctcttgccc ttccctgtcc ctctaaagca ataatggtcc catccaggca gtcggggct    3000
ggcctaggag atatctgagg gaggaggcca cctctccaag ggcttctgca ccctccaccc    3060
tgtcccccag ctctggtgag tcttggcggc agcagccatc ataggaaggg accaaggcaa    3120
ggcaggtgcc tccaggtgtg cacgtggcat gtggcctgtg gcctgtgtcc catgacccac    3180
ccctgtgctc cgtgcctcca ccaccactgg ccaccaggct ggcgcagcca aggccgaagc    3240
tctggctgaa ccctgtgctg gtgtcctgac cacccctcccc tctcttgcac ccgcctctcc    3300
cgtcagggcc caagtccctg ttttctgagc ccgggctgcc tgggctgttg gcactcacag    3360
acctggagcc cctgggtggg tggtggggag gggcgctggc ccagccggcc tctctggcct    3420
cccacccgat gctgctttcc cctgtgggga tctcaggggc tgtttgagga tatattttca    3480
ctttgtgatt atttcacttt agatgctgat gatttgtttt tgtatttta atggggtag    3540
cagctggact acccacgttc tcacacccac cgtccgccct gctcctccct ggctgccctg    3600
gccctgaggt gtgggggctg cagcatgttg ctgaggagtg aggaatagtt gagccccaag    3660
tcctgaagag gcgggccagc caggcgggct caaggaaagg gggtcccagt gggaggggca    3720
ggctgacatc tgtgtttcaa gtggggctcg ccatgccggg ggttcatagg tcactggctc    3780
tccaagtgcc agaggtgggc aggtggtggc actgagcccc cccaacactg tgccctggtg    3840
gagaaagcac tgacctgtca tgccccctc aaacctcctc ttctgacgtg ccttttgcac    3900
ccctcccatt aggacaatca gtcccctccc atctgggagt ccccttttct tttctacccct   3960
agccattcct ggtacccagc catctgccca ggggtgccc ctcctctccc atcccctgc    4020
cctcgtggcc agcccggctg gttttgtaag atgctgggtt ggtgcacagt gattttttc    4080
ttgtaattta aacaggccca gcattgctgg ttctatttaa tggacatgag ataatgttag    4140
aggttttaaa gtgattaaac gtgcagacta tgcaaaccag                         4180
```

<210> SEQ ID NO 14
<211> LENGTH: 794
<212> TYPE: PRT
<213> ORGANISM: Homo sapiens

<400> SEQUENCE: 14

```
Met Glu Leu Arg Pro Trp Leu Leu Trp Val Ala Ala Thr Gly Thr
1               5                   10                  15

Leu Val Leu Leu Ala Ala Asp Ala Gln Gly Gln Lys Val Phe Thr Asn
        20                  25                  30

Thr Trp Ala Val Arg Ile Pro Gly Gly Pro Ala Val Ala Asn Ser Val
            35                  40                  45

Ala Arg Lys His Gly Phe Leu Asn Leu Gly Gln Ile Phe Gly Asp Tyr
    50                  55                  60

Tyr His Phe Trp His Arg Gly Val Thr Lys Arg Ser Leu Ser Pro His
65                  70                  75                  80

Arg Pro Arg His Ser Arg Leu Gln Arg Glu Pro Gln Val Gln Trp Leu
                85                  90                  95

Glu Gln Gln Val Ala Lys Arg Arg Thr Lys Arg Asp Val Tyr Gln Glu
                100                 105                 110

Pro Thr Asp Pro Lys Phe Pro Gln Gln Trp Tyr Leu Ser Gly Val Thr
                115                 120                 125

Gln Arg Asp Leu Asn Val Lys Ala Ala Trp Ala Gln Gly Tyr Thr Gly
    130                 135                 140

His Gly Ile Val Val Ser Ile Leu Asp Asn Gly Ile Glu Lys Asn His
145                 150                 155                 160

Pro Asn Leu Ala Gly Asn Tyr Asp Pro Gly Ala Ser Phe Asp Val Asn
                165                 170                 175

Asp Gln Asp Pro Asp Pro Gln Pro Arg Tyr Thr Gln Met Asn Asp Asn
                180                 185                 190

Arg His Gly Thr Arg Cys Ala Gly Glu Val Ala Ala Val Ala Asn Asn
    195                 200                 205

Gly Val Cys Gly Val Gly Val Ala Tyr Asn Ala Arg Ile Gly Gly Val
    210                 215                 220

Arg Met Leu Asp Gly Glu Val Thr Asp Ala Val Glu Ala Arg Ser Leu
225                 230                 235                 240

Gly Leu Asn Pro Asn His Ile His Ile Tyr Ser Ala Ser Trp Gly Pro
                245                 250                 255

Glu Asp Asp Gly Lys Thr Val Asp Gly Pro Ala Arg Leu Ala Glu Glu
                260                 265                 270

Ala Phe Phe Arg Gly Val Ser Gln Gly Arg Gly Gly Leu Gly Ser Ile
                275                 280                 285

Phe Val Trp Ala Ser Gly Asn Gly Gly Arg Glu His Asp Ser Cys Asn
    290                 295                 300

Cys Asp Gly Tyr Thr Asn Ser Ile Tyr Thr Leu Ser Ile Ser Ser Ala
305                 310                 315                 320

Thr Gln Phe Gly Asn Val Pro Trp Tyr Ser Glu Ala Cys Ser Ser Thr
                325                 330                 335

Leu Ala Thr Thr Tyr Ser Ser Gly Asn Gln Asn Glu Lys Gln Ile Val
                340                 345                 350

Thr Thr Asp Leu Arg Gln Lys Cys Thr Glu Ser His Thr Gly Thr Ser
    355                 360                 365

Ala Ser Ala Pro Leu Ala Ala Gly Ile Ile Ala Leu Thr Leu Glu Ala
    370                 375                 380

Asn Lys Asn Leu Thr Trp Arg Asp Met Gln His Leu Val Val Gln Thr
385                 390                 395                 400

Ser Lys Pro Ala His Leu Asn Ala Asn Asp Trp Ala Thr Asn Gly Val
                405                 410                 415

Gly Arg Lys Val Ser His Ser Tyr Gly Tyr Gly Leu Leu Asp Ala Gly
```

```
                420            425            430
Ala Met Val Ala Leu Ala Gln Asn Trp Thr Thr Val Ala Pro Gln Arg
            435                440                445
Lys Cys Ile Ile Asp Ile Leu Thr Glu Pro Lys Asp Ile Gly Lys Arg
450                455                460
Leu Glu Val Arg Lys Thr Val Thr Ala Cys Leu Gly Glu Pro Asn His
465                470                475                480
Ile Thr Arg Leu Glu His Ala Gln Ala Arg Leu Thr Leu Ser Tyr Asn
                485                490                495
Arg Arg Gly Asp Leu Ala Ile His Leu Val Ser Pro Met Gly Thr Arg
            500                505                510
Ser Thr Leu Leu Ala Ala Arg Pro His Asp Tyr Ser Ala Asp Gly Phe
            515                520                525
Asn Asp Trp Ala Phe Met Thr Thr His Ser Trp Asp Glu Asp Pro Ser
            530                535                540
Gly Glu Trp Val Leu Glu Ile Glu Asn Thr Ser Glu Ala Asn Asn Tyr
545                550                555                560
Gly Thr Leu Thr Lys Phe Thr Leu Val Leu Tyr Gly Thr Ala Pro Glu
                565                570                575
Gly Leu Pro Val Pro Pro Glu Ser Ser Gly Cys Lys Thr Leu Thr Ser
            580                585                590
Ser Gln Ala Cys Val Val Cys Glu Glu Gly Phe Ser Leu His Gln Lys
            595                600                605
Ser Cys Val Gln His Cys Pro Pro Gly Phe Ala Pro Gln Val Leu Asp
            610                615                620
Thr His Tyr Ser Thr Glu Asn Asp Val Glu Thr Ile Arg Ala Ser Val
625                630                635                640
Cys Ala Pro Cys His Ala Ser Cys Ala Thr Cys Gln Gly Pro Ala Leu
                645                650                655
Thr Asp Cys Leu Ser Cys Pro Ser His Ala Ser Leu Asp Pro Val Glu
                660                665                670
Gln Thr Cys Ser Arg Gln Ser Gln Ser Ser Arg Glu Ser Pro Pro Gln
            675                680                685
Gln Gln Pro Pro Arg Leu Pro Pro Glu Val Glu Ala Gly Gln Arg Leu
            690                695                700
Arg Ala Gly Leu Leu Pro Ser His Leu Pro Glu Val Val Ala Gly Leu
705                710                715                720
Ser Cys Ala Phe Ile Val Leu Val Phe Val Thr Val Phe Leu Val Leu
                725                730                735
Gln Leu Arg Ser Gly Phe Ser Phe Arg Gly Val Lys Val Tyr Thr Met
            740                745                750
Asp Arg Gly Leu Ile Ser Tyr Lys Gly Leu Pro Pro Glu Ala Trp Gln
            755                760                765
Glu Glu Cys Pro Ser Asp Ser Glu Glu Asp Glu Gly Arg Gly Glu Arg
            770                775                780
Thr Ala Phe Ile Lys Asp Gln Ser Ala Leu
785                790

<210> SEQ ID NO 15
<211> LENGTH: 4179
<212> TYPE: DNA
<213> ORGANISM: Homo sapiens

<400> SEQUENCE: 15
gcggggaagc agcagcggcc aggatgaatc ccaggtgctc tggagctgga tggtgaaggt      60
```

```
cggcactctt cacccctcccg agccctgccc gtctcggccc catgccccca ccagtcagcc    120
ccgggccaca ggcagtgagc aggcacctgg gagccgaggc cctgtgacca ggccaaggag    180
acgggcgctc cagggtccca gccacctgtc cccccatgg agctgaggcc ctggttgcta    240
tgggtggtag cagcaacagg aaccttggtc ctgctagcag ctgatgctca gggccagaag    300
gtcttcacca acacgtgggc tgtgcgcatc cctggaggcc cagcggtggc caacagtgtg    360
gcacggaagc atgggttcct caacctgggc cagatcttcg gggactatta ccacttctgg    420
catcgaggag tgacgaagcg gtccctgtcg cctcaccgcc cgcggcacag ccggctgcag    480
agggagcctc aagtacagtg gctggaacag caggtggcaa agcgacggac taaacgggac    540
gtgtaccagg agcccacaga ccccaagttt cctcagcagt ggtacctgtc tggtgtcact    600
cagcgggacc tgaatgtgaa ggcggcctgg gcgcagggct acacagggca cggcattgtg    660
gtctccattc tggacgatgg catcgagaag aaccacccgg acttggcagg caattatgat    720
cctggggcca gttttgatgt caatgaccag daccctgacc cccagcctcg gtacacacag    780
atgaatgaca acaggcacgg cacacggtgt gcggggaag tggctgcggt ggccaacaac    840
ggtgtctgtg gtgtaggtgt ggcctacaac gcccgcattg gaggggtgcg catgctggat    900
ggcgaggtga cagatgcagt ggaggcacgc tcgctgggcc tgaacccaa ccacatccac    960 atctacagtg ccagctgggg ccccgaggat gacggcaaga cagtggatgg gccagcccgc   1020
ctcgccgagg aggccttctt ccgtgggggtt agccagggcc gagggggggct gggctccatc   1080 tttgtctggg cctcggggaa cggggggccgg gaacatgaca gctgcaactg cgacggctac   1140
accaacagta tctacacgct gtccatcagc agcgccacgc agtttggcaa cgtgccgtgg   1200
tacagcgagg cctgctcgtc cacactggcc acgacctaca gcagtggcaa ccagaatgag   1260
aagcagatcg tgacgactga cttgcggcag aagtgcacgg agtctcacac gggcacctca   1320
gcctctgccc ccttagcagc cggcatcatt gctctcaccc tggaggccaa taagaacctc   1380
acatggcggg acatgcaaca cctggtggta cagacctcga agccagccca cctcaatgcc   1440
aacgactggg ccaccaatgg tgtgggccgg aaagtgagcc actcatatgg ctacgggctt   1500
tggacgcagg cgccatggtg gccctggccc agaattggac cacagtggcc cccagcgga   1560 agtgcatcat cgacatcctc accgagccca aagacatcgg gaaacggctc gaggtgcgga   1620
agaccgtgac cgcgtgcctg ggcgagccca accacatcac tcggctggag cacgctcagg   1680
cgcggctcac cctgtcctat aatcgccgtg gcgacctggc catccacctg gtcagcccca   1740
tgggcacccg ctccaccctg ctggcagcca ggccacatga ctactccgca gatgggttta   1800
atgactgggc cttcatgaca actcattcct gggatgagga tccctctggc gagtgggtcc   1860
tagagattga aaacaccagc gaagccaaca actatgggac gctgaccaag ttcacccctcg   1920 tactctatgg caccgcccct gaggggctgc ccgtacctcc agaaagcagt ggctgcaaga   1980
ccctcacgtc cagtcaggcc tgtgtggtgt gcgaggaagg cttctccctg caccagaaga   2040
gctgtgtcca gcactgccct ccagggttcg ccccccaagt cctcgatacg cactatagca   2100
ccgagaatga cgtggagacc atccgggcca gcgtctgcgc ccctgccac gcctcatgtg   2160 ccacatgcca ggggccggcc ctgacagact gcctcagctg ccccagccac gcctccttgg   2220
accctgtgga gcagacttgc tcccggcaaa gccagagcag ccgagagtcc ccgccacagc   2280
agcagccacc tcggctgccc ccggaggtgg aggcgggca acggctgcgg gcagggctgc   2340
tgccctcaca cctgcctgag gtggtggccg gcctcagctg cgccttcatc gtgctggtct   2400
tcgtcactgt cttcctggtc ctgcagctgc gctctggctt tagttttcgg ggggtgaagg   2460
```

-continued

```
tgtacaccat ggaccgtggc ctcatctcct acaaggggct gccccctgaa gcctggcagg    2520
aggagtgccc gtctgactca gaagaggacg agggccgggg cgagaggacc gcctttatca    2580
aagaccagag cgccctctga tgagcccact gcccaccccc tcaagccaat ccctccttg    2640 ggcactttt aattcaccaa agtatttttt tatcttggga ctgggtttgg accccagctg    2700
ggaggcaaga ggggtggaga ctgcttccca tcctaccctc gggcccacct ggccacctga    2760
ggtgggccca ggaccagctg gggcgtgggg agggccgtac cccaccctca gcacccttc    2820 catgtggaga aaggagtgaa acctttaggg cagcttgccc cggccccggc cccagccaga    2880
gttcctgcgg agtgaagagg ggcagccctt gcttgttggg attcctgacc caggccgcag    2940
ctcttgccct tccctgtccc tctaaagcaa taatggtccc atccaggcag tcggggctg    3000 gcctaggaga tatctgaggg aggaggccac ctctccaagg gcttctgcac cctccaccct    3060
gtcccccagc tctggtgagt cttggcggca gcagccatca taggaaggga ccaaggcaag    3120
gcaggtgcct ccaggtgtgc acgtggcatg tggcctgtgg cctgtgtccc atgacccacc    3180
cctgtgctcc gtgcctccac caccactggc caccaggctg gcgcagccaa ggccgaagct    3240
ctggctgaac cctgtgctgg tgtcctgacc accctcccct ctcttgcacc cgcctctccc    3300
gtcagggccc aagtccctgt tttctgagcc cgggctgcct gggctgttgg cactcacaga    3360
cctggagccc ctgggtgggt ggtgggggagg ggcgctggcc cagccggcct ctctggcctc    3420
ccacccgatg ctgctttccc ctgtggggat ctcagggggct gtttgaggat atattttcac    3480
tttgtgatta tttcacttta gatgctgatg atttgttttt gtattttaa tgggggtagc    3540 agctggacta cccacgttct cacacccacc gtccgccctg ctcctccctg gctgccctgg    3600
ccctgaggtg tgggggctgc agcatgttgc tgaggagtga ggaatagttg agccccaagt    3660
cctgaagagg cgggccagcc aggcgggctc aaggaaaggg ggtcccagtg ggaggggcag    3720
gctgacatct gtgtttcaag tggggctcgc catgccgggg gttcataggt cactggctct    3780
ccaagtgcca gaggtgggca ggtggtggca ctgagccccc ccaacactgt gccctggtgg    3840
agaaagcact gacctgtcat gccccccctca aacctcctct tctgacgtgc cttttgcacc    3900
cctcccatta ggacaatcag tcccctccca tctgggagtc ccctttttctt ttctacccta    3960 gccattcctg gtacccagcc atctgcccag gggtgccccc tcctctccca tcccctgcc    4020 ctcgtggcca gcccggctgg ttttgtaaga tgctgggttg gtgcacagtg atttttttct    4080
tgtaatttaa acaggcccag cattgctggt tctatttaat ggacatgaga taatgttaga    4140
ggttttaaag tgattaaacg tgcagactat gcaaaccag                          4179
```

```
<210> SEQ ID NO 16
<211> LENGTH: 11
<212> TYPE: PRT
<213> ORGANISM: Homo sapiens

<400> SEQUENCE: 16

Thr Asn Gly Ile Glu Gly Arg Ala Leu Asp Pro
1               5                   10
```